US008623911B2

(12) United States Patent
Jacobs et al.

(10) Patent No.: US 8,623,911 B2
(45) Date of Patent: Jan. 7, 2014

(54) BORON-CONTAINING SMALL MOLECULES AS ANTI-PROTOZOAL AGENT

(75) Inventors: Robert T. Jacobs, Wake Forest, NC (US); Daitao Chen, Raleigh, NC (US); Matthew Orr, Raleigh, NC (US); Jacob J. Plattner, Orinda, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 13/636,114

(22) PCT Filed: Mar. 18, 2011

(86) PCT No.: PCT/US2011/029088
§ 371 (c)(1),
(2), (4) Date: Jan. 24, 2013

(87) PCT Pub. No.: WO2011/116348
PCT Pub. Date: Sep. 22, 2011

(65) Prior Publication Data
US 2013/0231304 A1    Sep. 5, 2013

Related U.S. Application Data

(60) Provisional application No. 61/315,806, filed on Mar. 19, 2010.

(51) Int. Cl.
*A61K 31/69* (2006.01)
*C07F 5/02* (2006.01)

(52) U.S. Cl.
USPC .......................... 514/456; 549/213

(58) Field of Classification Search
USPC ........................... 514/456; 549/213
See application file for complete search history.

(56) References Cited

U.S. PATENT DOCUMENTS

| | | | |
|---|---|---|---|
| 2,260,336 A | 10/1941 | Prescott et al. | |
| 3,686,398 A | 8/1972 | Kohn et al. | |
| 3,873,279 A | 3/1975 | Singer | |
| 4,602,011 A | 7/1986 | West et al. | |
| 4,716,035 A | 12/1987 | Sampathkamar | |
| 4,766,113 A | 8/1988 | West et al. | |
| 4,894,220 A | 1/1990 | Nabi et al. | |
| 4,919,934 A | 4/1990 | Deckner et al. | |
| 5,348,947 A | 9/1994 | Patel et al. | |
| 5,348,948 A | 9/1994 | Patel et al. | |
| 5,591,731 A | 1/1997 | Kennedy et al. | |
| 5,668,258 A | 9/1997 | Stolowitz | |
| 5,688,928 A | 11/1997 | Stolowitz | |
| 5,831,045 A | 11/1998 | Stolowitz et al. | |
| 5,880,188 A | 3/1999 | Austin et al. | |
| 5,962,498 A | 10/1999 | Driedger et al. | |
| 6,083,903 A | 7/2000 | Adams et al. | |
| 6,221,640 B1 | 4/2001 | Tao et al. | |
| 6,306,628 B1 | 10/2001 | Rothschild et al. | |
| 6,369,098 B1 | 4/2002 | Pershadsingh et al. | |
| 6,521,619 B2 | 2/2003 | Link et al. | |
| 6,800,645 B1 | 10/2004 | Cox et al. | |
| 6,855,848 B2 | 2/2005 | Scherer et al. | |
| 7,169,603 B2 | 1/2007 | Hedley et al. | |
| 7,205,425 B2 | 4/2007 | Shibasaki et al. | |
| 7,217,701 B2 | 5/2007 | Mikoshiba et al. | |
| 7,390,806 B2 | 6/2008 | Lee et al. | |
| 7,446,236 B2 | 11/2008 | Naud et al. | |
| 7,465,836 B2 | 12/2008 | Lee et al. | |
| 7,582,621 B2 | 9/2009 | Baker et al. | |
| 7,767,657 B2 | 8/2010 | Baker et al. | |
| 7,816,344 B2 | 10/2010 | Baker et al. | |
| 8,039,450 B2 | 10/2011 | Akama et al. | |
| 8,168,614 B2 | 5/2012 | Baker et al. | |
| 2002/0028831 A1 | 3/2002 | Manley | |
| 2002/0161230 A1 | 10/2002 | Meudt et al. | |
| 2003/0032673 A1 | 2/2003 | Nagy | |
| 2004/0077601 A1 | 4/2004 | Adams et al. | |
| 2004/0224923 A1 | 11/2004 | Lee et al. | |
| 2005/0054644 A1 | 3/2005 | Lee et al. | |
| 2005/0125852 A1 | 6/2005 | Caenepeel et al. | |
| 2006/0009386 A1 | 1/2006 | Stossel et al. | |
| 2006/0222671 A1 | 10/2006 | Weidner | |
| 2006/0234981 A1 | 10/2006 | Baker et al. | |
| 2007/0155699 A1 | 7/2007 | Baker et al. | |
| 2007/0286822 A1 | 12/2007 | Sanders et al. | |
| 2007/0293457 A1 | 12/2007 | Baker et al. | |
| 2009/0227541 A1 | 9/2009 | Baker et al. | |
| 2010/0048570 A1 | 2/2010 | Kim et al. | |
| 2010/0256092 A1 | 10/2010 | Xia et al. | |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9622023 A1 | 7/1996 |
| WO | WO 9812206 A1 | 3/1998 |

(Continued)

OTHER PUBLICATIONS

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anti-inflammatory agent (AN2728) for the potential topical treatment of psoriasis and atopic dernatitis", Bioorganic & Medicinal Chemistry Letters, (2009) 19: 2129-2132.

Alley, et al., "Recent Progress on Topical Therapy of Onychomycosis", Expert Opinion Investigate Drugs(Feb. 2007) 16(2): 157-67.

(Continued)

*Primary Examiner* — Samantha Shterengarts
(74) *Attorney, Agent, or Firm* — Morgan, Lewis & Bockius LLP

(57) ABSTRACT

This invention provides, among other things, novel compounds useful for treating protozoal infections, pharmaceutical compositions containing such compounds, as well as combinations of these compounds with at least one additional therapeutically effective agent.

28 Claims, 1 Drawing Sheet

(56) References Cited

FOREIGN PATENT DOCUMENTS

| WO | WO 0027822 | 5/2000 |
|---|---|---|
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions,"Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Progress on New Therapeutics for Fungal Nail Infections", Annual Reports in Medicinal Chemistry, vol. 40: pp. 323-335, (2005).
Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Cusack, S., et al., "The 2 A Crystal Structure of leucyl-tRNA Synthetase and its Complex with a Leucyl-Adenylate Analogue." EMBO Journal, vol. 19; pp. 2351-2361, (2000).
Dale, et al., "Substituted Styrenes VIII Syntheses and some Reactions of the Vinylbenzeneboronic Acids" J. Org. Chem. vol. 27, pp. 2598-2603, (Jan. 1, 1962).

Denis, "Pharmacology 1104 Lecture: Drug Classifications & Characteristics of Antimicrobials"(2003).
Dian, "International Nomenclature of Organics", China Petrochemical Press, 1st Edition; 50-51 (Jan. 21, 2004).
Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).
Ferrer, "Targeting Aminocytl-tRNA Synthetases for the Treatment of Fungal Infections", Drug News Perspective, vol. 19, No. 6; pp. 347-348, (Jul./Aug. 2006).
Fungicide: Definition from Answer.com, (1998).
Goodman, et al., "Goodman & Gilman's Manual of Pharmacology and Therapeutics" Chapter 40;681-694 (2008).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al.; "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02: pp. 139-144, (1996) (English Abstract).
Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Arydialkkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).
Hui, et al., "In Vitro Penetration of a Novel Oxaborole Antifungal (AN2690) into the Human Nail Plate", Journal of Pharmaceutical Sciences (2007) 96(10): 2622-2631.
Lampe, et al., "Synthesis and Protien Kinase Inhibitory Activity of Balanol Analogues with Modified Benzophenone Subunits", J. Med. Chem., vol. 45(12); pp. 2624-2643, (2002).
Lee, K., et al., "Molecular Study of the Editing Active Site of Escherichia coli Leucyl-tRNA Synthetase: Two Amino Acid Binding Site in the Editing Domain", vol. 54; pp. 693-704, (2004).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Luan, et al., "Inhibition of Experimental Periodontitis by a topical boron-base antimicrobial" J Dent. Res, 87(2):148-152 (2008).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).
McMillin, et al., "Systemic Aspects of Psoriasis: An Integrative Model Based on Intestinal Etiology", Int. Med. vol. 2, Issue 2/3, (1999).
Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Mudran, "Drug Delivery to the Nail Following Topical Application", International Journal of Pharmaceutics, vol. 236: pp. 1-26, (2002).
Pateni, et al., "Bioisosterism: A Rational Approach to Drug Design", Chem. Rev., vol. 96; pp. 3147-3176 (1996).
Perola, E., et al., "Successful Virtual Screening of a Chemical Database for Farnesltransferase Inhibitor Leads." vol. 43; pp. 401-4008, (2000).
Qin, et al., "Luminescent Organoboron Quinolate Polymers," Journal of the American Chemical Society, vol. 126, No. 22; pp. 7015-7018, (Jun. 9, 2004).
Qin, Clinical Mycology, Fudan Press, Shanghai Medical University Press, pp. 92, 111, 340-341, 365, 437 and 487 (2001) With English Translation.

(56) References Cited

OTHER PUBLICATIONS

Rock, et al.,"An Antifungal Agents Inhibits Aminoacyl-tRNA Synthetase by Trapping tRNA in the Editing Site", Science, vol. 316, No. 5832; pp. 1759-1761 (Jun. 22, 2007).

Silverman, "The Organic Chemistry of Drug Design and Drug Action", 2nd Edition, Northwestern University, Department of Chemistry, Evanston, Illinois, Section 2: 29-32 (2004).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Standard Broth Macrodilution Assay: Lack of Effect of Phenol Red" Diagn. Microbiol. Infect. Dis. vol. 21; pp. 129-133; (1995).

Tabuchi, et al., "Anticoccidial Activity of some Azacyclo Organoborinates," Heterocycles, vol. 60, No. 01; pp. 177-182, (2003).

Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical, Research Communications, vol. 234; pp. 320-324, (1997).

Ye, et al., "Convenient and Versatile Syntheis of formyl-substituted Benzoxaboroles", Tetrahedron, vol. 65; pp. 8738-8744, (2009).

Williams, et al., "Foye's Principles of Medicinal Chemistry", 5th Edition, 2002, Lippincoot Williams & Wilkins, p. 59.

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.

"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.

"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.

"AN2718 Demonstrates Significant Efficacy in Three Phase Ib Psoriasis Microplague Trials" Scientific Presentation at the American Academy of Dermatology Annual Meeting, San Francisco, CA Mar. 6-10, 2009.

"AN2728 Demonstrates Significant Safety and Efficacy in Phase IIa Double Blind Trial in Plague Type Psoriasis", Scientific Presentation at the American Academy of Dermatology Annual Meeting, San Francisco, CA Mar. 6-10, 2009.

"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.

"A New Class of Benzoxaborole-based Potent Antitrypanosomal Agents: Probing Effect of Different Linkage Groups in *Trypanosome brucei* Growth Inhibition", Scientific Presentation at the American Society of Tropical Medicine and Hygiene Conference, New Orleans, LA Dec. 7-11, 2008.

"AN2920, A Novel Oxaborole, Shows in Vitro and in Vivo Activity Against *Trypanosomal brucei*", Scientific Presentation at the American Society of Tropical Medicine and Hygiene Conference, New Orleans, LA Dec. 7-11, 2008.

"A Novel Oxaborole, AN3520, Show Efficacy against Human African Trypanomiasis In Vitro and In Vivo, Including Promise in a Murine CNS Model of *T. brucei* Infection", Scientific Presentation at the American Society of Tropical Medicine and Hygiene Conference, New Orleans, LA Dec. 7-11, 2008.

"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.

"AN2728 Ointment, a Novel Oxaborole with Anti-Inflammatory Activity, Demonstrates Safety and Significant Efficacy in a Phase Ib Psoriasis Plague Test", Scientific Presentation at Montagna Symposium on Biology of Skin, Gleneden Beach, OR, Oct. 2-6, 2008.

"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.

"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.

"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.

"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.

"Preclinical Toxicology of AN2728, a Novel Borinic Acid Ester with Anti-Inflammatory Activity", Americal Academy of Dermatology, 65th Annual Meeting, Washington, DC, Feb. 2-6, 2007.

"AN2728, a Novel Oxaborole with Broad-Spectrum In Vitro Anti-Inflammatory Activity", American Academy of Dermatology, 65th Annual Meeting, Washington, DC Feb 2-6, 2007.

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of a Multi-Center Study to Evaluate the Safety and Efficacy of Topically Applied AN2690 5.0% and 7.5% Solutions for

(56) References Cited

OTHER PUBLICATIONS the Treatment of Onychomycosis of the Great Toenail", Americal Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.

"Skin Penetration and Anti-Inflammatory Activity of AN2728, a Novel Oxaborole", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

| Compound Number | T. brucei IC50 (ug/mL) | | L929 Cytotox IC50 (ug/mL) | S9 t1/2 (min) | | Solubility, pH 7.4 PBS (uM) |
|---|---|---|---|---|---|---|
| M1 | 0.175 | > | 10 | 135 | | 100 |
| M2 | 0.068 | > | 10 | 51 | | |
| M3 | 0.276 | > | 10 | | | |
| M4 | 0.224 | > | 10 | 93 | | |
| M5 | 0.024 | > | 10 | 51.1 | | 100 |
| M6 | 0.271 | > | 10 | | | |
| M7 | 0.077 | > | 10 | 72 | | 25 |
| M8 | 0.046 | > | 10 | 81 | | |
| M9 | 0.267 | > | 10 | | | |
| M10 | 0.348 | > | 10 | | | |
| M11 | 0.08 | > | 10 | | | 50 |
| M12 | 0.024 | > | 10 | 43 | | 50 |
| M13 | 0.045 | > | 10 | 37 | | 13 |
| M14 | 0.023 | | 5.18 | 29 | | 25 |
| M15 | 0.088 | > | 10 | 179 | | |
| M16 | 0.24 | > | 10 | 110 | | |
| M17 | 0.195 | > | 10 | | | |
| M18 | 0.513 | > | 10 | | | |
| M19 | 0.072 | > | 10 | 198 | | 100 |
| M20 | 0.469 | > | 10 | | | 50 |
| M21 | 0.171 | > | 10 | | | 2 |
| M22 | 0.1 | > | 10 | | | |
| M23 | 0.093 | > | 10 | | | |
| M24 | 0.83 | > | 10 | | | 100 |
| M25 | 0.047 | > | 10 | | | |
| M26 | 0.153 | > | 10 | 85 | | 100 |
| M27 | 0.032 | > | 10 | 65 | | 50 |
| M28 | 0.051 | > | 10 | 179 | | 100 |
| M29 | 0.014 | > | 10 | 56 | | 25 |
| M30 | 0.751 | > | 10 | | | |
| M31 | 0.087 | > | 10 | | | |
| M32 | 0.053 | > | 10 | 37 | | |
| M33 | 0.054 | > | 10 | 46 | | |
| M34 | 0.031 | > | 10 | | | |
| M35 | 0.107 | > | 10 | | | |
| M36 | 0.046 | > | 10 | 65 | | 13 |
| M37 | 0.131 | > | 10 | | | |
| M38 | 0.177 | > | 10 | 36 | | |
| M39 | 0.098 | > | 10 | | | |
| M40 | 0.022 | < | 0.63 | 48 | | 50 |
| M41 | 0.174 | > | 10 | 44 | > | 200 |
| M42 | 0.125 | | 4.38 | | | 50 |
| M43 | 0.735 | > | 10 | | | |
| M44 | 0.173 | | 4.22 | | | |
| M45 | 0.098 | | 6.09 | | | |
| M46 | 0.079 | > | 10 | 12.7 | | |
| M47 | 0.078 | > | 10 | 30.4 | | |
| M48 | 0.087 | | 7.23 | | | |
| M49 | 0.235 | > | 10 | | | |
| M50 | >5 | > | 10 | 102 | | |
| M51 | >5 | > | 10 | 350 | | |
| M52 | >5 | > | 10 | 108 | | |

BORON-CONTAINING SMALL MOLECULES AS ANTI-PROTOZOAL AGENT

CROSS-REFERENCE TO RELATED APPLICATIONS

This application is a national stage entry of PCT/US11/29088, filed on Mar. 18, 2011, which claims the benefit of U.S. Provisional Pat. App. No. 61/315,806, filed Mar. 19, 2010, each of which is incorporated by reference in its entirety for all purposes.

BACKGROUND OF THE INVENTION

The global rise of protozoa resistant to antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multidrug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

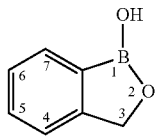

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutically effective agent.

BRIEF DESCRIPTION OF THE DRAWINGS

Biological data for exemplary compounds of the invention is provided in FIG. 1.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato) diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, is general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2$ (pddf) is 1,1'-Bis(diphenylphosphino)ferrocene]dichloropalladium(II); Pd/C is the catalyst known as palladium on carbon; $Pd_2(dba)_3$ is an organometallic catalyst known as tris(dibenzylideneacetone)dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R") =NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2 m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R") =NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term antiprotozoal or antiprotozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

In one aspect, the invention provides novel boron compounds. The novel compounds, as well as pharmaceutical compositions containing such compounds or combinations of these compounds with at least one additional therapeutically effective agent, can be used for, among other things, treating protozoal infections.

III. The Compounds

IIIa.

In one aspect, the invention provides a compound of the invention. In an exemplary embodiment, the invention is a compound described herein. In an exemplary embodiment, the invention is a compound according to a formula described herein.

In an exemplary embodiment, the compound of the invention has the following structure:

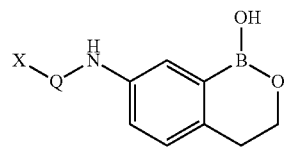

wherein X is selected from the group consisting of substituted phenyl, substituted or unsubstituted phenylalkyl, substituted or unsubstituted heteroaryl and unsubstituted cycloalkyl, Q is $SO_2$ or C=O, or a salt thereof. In an exemplary embodiment, X is substituted phenyl. In an exemplary embodiment, X is substituted phenyl which is not monosubstituted with unsubstituted alkyl. In an exemplary embodiment, X is substituted phenyl which is not monosubstituted with halosubstituted alkyl. In an exemplary embodiment, X is phenyl, substituted with at least one member selected from the group consisting of: halogen, cyano, nitro, OR, SR, NRR, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, wherein each R is independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, X is phenyl, substituted with at least one or more of the substituents described herein. In an exemplary embodiment, X is heteroaryl, optionally substituted with at least one or more of the substituents described herein: In an exemplary embodiment, X is phenyl, substituted with at least one member selected from the group consisting of halogen, cyano, nitro, OR, SR, NRR, unsubstituted alkyl, halosubstituted alkyl, unsubstituted alkoxy, alkyl substituted amidyl, substituted or unsubstituted cycloalkyl, substituted or unsubstituted heterocycloalkyl, substituted or unsubstituted aryl and substituted or unsubstituted heteroaryl, wherein each R is independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, X is not a phenyl which is monosubstituted with unsubstituted alkyl. In an exemplary embodiment, X is not a phenyl which is monosubstituted with halosubstituted alkyl. In an exemplary embodiment, X is not a phenyl which is only substituted with halogens.

In an exemplary embodiment, the compound of the invention has the following structure:

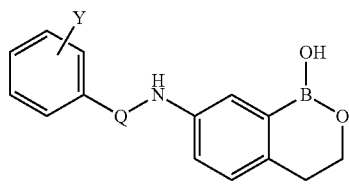

wherein Q is $SO_2$ or C=O, Y is selected from the group consisting of halogen, halo-substituted $C_1$-$C_6$ alkyl and unsubstituted $C_1$-$C_6$ alkyl; or a salt thereof. In an exemplary embodiment, Q is $SO_2$. In an exemplary embodiment, Q is C=O. In an exemplary embodiment, Y is an unsubstituted $C_3$ alkyl. In an exemplary embodiment, Y is an unsubstituted $C_4$ alkyl. In an exemplary embodiment, Y is an unsubstituted $C_5$ alkyl. In an exemplary embodiment, Y is an unsubstituted $C_6$ alkyl. In an exemplary embodiment, Y is selected from the group consisting of methyl, ethyl, propyl, butyl, pentyl and hexyl. In an exemplary embodiment, Y is selected from the group consisting of cyclopropyl, cyclobutyl, cyclopentyl and cyclohexyl. In an exemplary embodiment, Y is halo-substituted $C_1$-$C_6$ alkyl. In an exemplary embodiment, Y is $C_1$-$C_6$ alkyl, substituted with one halogen. In an exemplary embodiment, Y is $C_1$-$C_6$ alkyl, substituted with two halogens. In an exemplary embodiment, Y is $C_1$-$C_6$ alkyl, substituted with three halogens. In an exemplary embodiment, Y is $C_1$-$C_6$ alkyl, substituted with four halogens. In an exemplary embodiment, Y is $C_1$-$C_6$ alkyl, substituted with one fluorine. In an exemplary embodiment, Y is $C_1$-$C_6$ alkyl, substituted with two fluorines. In an exemplary embodiment, Y is $C_1$-$C_6$ alkyl, substituted with three fluorines. In an exemplary embodiment, Y is $C_1$-$C_6$ alkyl, substituted with four fluorines. In an exemplary embodiment, Y is $C_1$-$C_6$ alkyl, substituted with one chlorine. In an exemplary embodiment, Y is $C_1$-$C_6$ alkyl, substituted with two chlorines. In an exemplary embodiment, Y is $C_1$-$C_6$ alkyl, substituted with three chlorines. In an exemplary embodiment, Y is $C_1$-$C_6$ alkyl, substituted with four chlorines. In an exemplary embodiment, Y is $C_1$-$C_6$ alkyl, substituted with a combination of two different halogens. In an exemplary embodiment, Y is $C_1$-$C_6$ alkyl, substituted with at least one fluorine and at least one chlorine. In an exemplary embodiment, Y is $C_1$-$C_6$ alkyl, substituted with at least one fluorine and at least one bromine. In an exemplary embodiment, Y is $C_1$-$C_6$ alkyl, substituted with at least one chlorine and at least one bromine. In an exemplary embodiment, Y is fluoro-substituted $C_1$-$C_6$ alkyl. In an exemplary embodiment, Y is trifluoro-substituted $C_1$-$C_6$ alkyl. In an exemplary embodiment, the compound of the invention has a structure which is selected from the group consisting of:

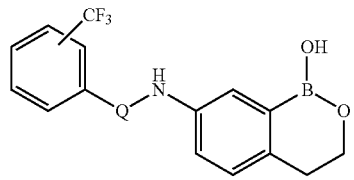

or a salt thereof.

In an exemplary embodiment, the compound of the invention has a structure which is selected from the group consisting of:

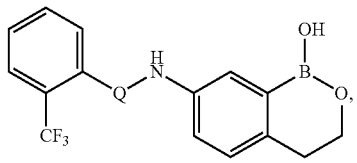

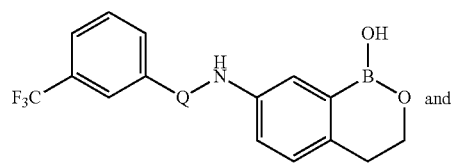

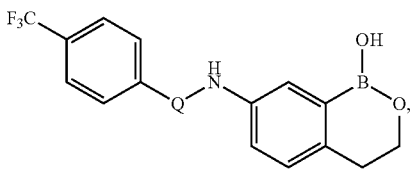

wherein Q is $SO_2$ or C=O. In an exemplary embodiment, Q is $SO_2$. In an exemplary embodiment, Q is C=O.

In an exemplary embodiment, the compound has the following structure:

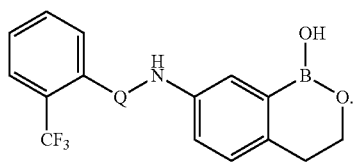

In an exemplary embodiment, the compound of the invention has a structure which is selected from the group consisting of:

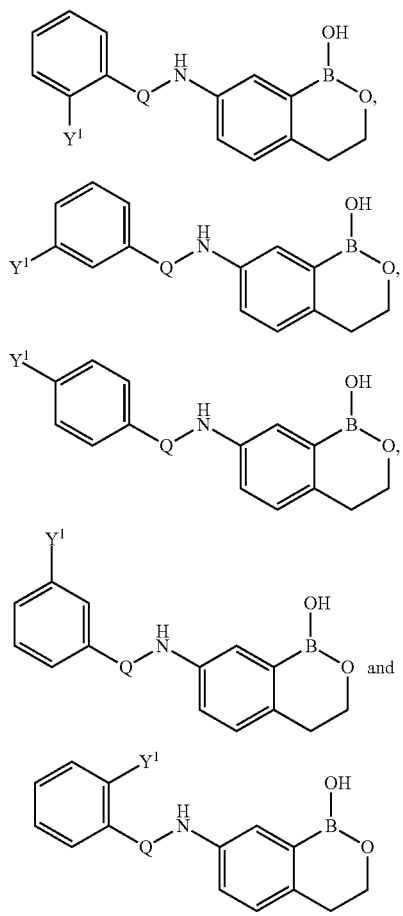

wherein $Y^1$ is a halogen, and Q is as described herein. In an exemplary embodiment, Q is $SO_2$. In an exemplary embodiment, Q is C=O.

In an exemplary embodiment, the compound of the invention has a structure which is selected from the group consisting of:

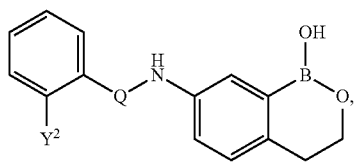

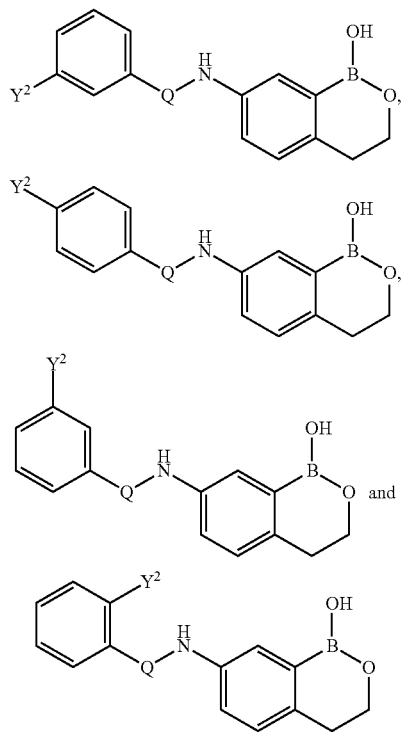

wherein $Y^2$ is unsubstituted alkyl, and Q is as described herein. In an exemplary embodiment, Q is $SO_2$. In an exemplary embodiment, Q is C=O. In an exemplary embodiment, $Y^2$ is unsubstituted $C_1$ alkyl. In an exemplary embodiment, $Y^2$ is unsubstituted $C_2$ alkyl. In an exemplary embodiment, $Y^2$ is unsubstituted $C_3$ alkyl. In an exemplary embodiment, $Y^2$ is unsubstituted n-propyl or isopropyl. In an exemplary embodiment, $Y^2$ is unsubstituted $C_4$ alkyl. In an exemplary embodiment, $Y^2$ is n-butyl or sec-butyl or iso-butyl or tert-butyl. In an exemplary embodiment, $Y^2$ is unsubstituted $C_5$ alkyl. In an exemplary embodiment, $Y^2$ is unsubstituted $C_6$ alkyl.

In an exemplary embodiment, the compound of the invention has a structure which is selected from the group consisting of:

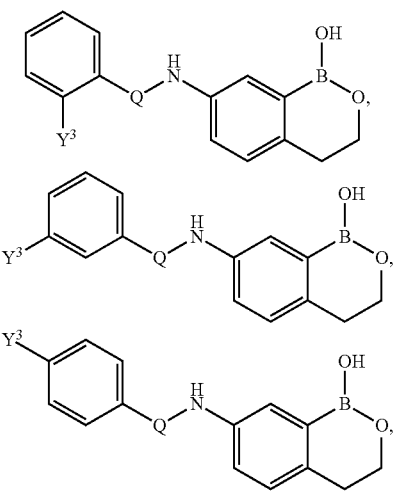

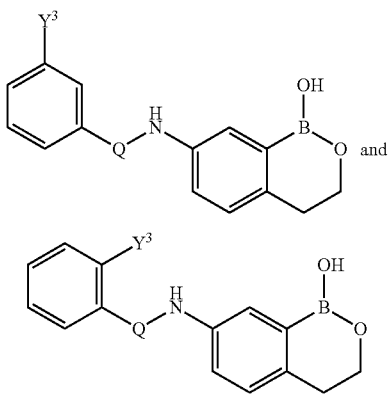

wherein $Y^3$ is unsubstituted alkoxy, and Q is as described herein. In an exemplary embodiment, Q is $SO_2$. In an exemplary embodiment, Q is C=O. In an exemplary embodiment, $Y^3$ is unsubstituted $C_1$ alkoxy. In an exemplary embodiment, $Y^3$ is unsubstituted $C_2$ alkoxy. In an exemplary embodiment, $Y^3$ is unsubstituted $C_3$ alkoxy. In an exemplary embodiment, $Y^3$ is n-propoxy. In an exemplary embodiment, $Y^3$ is isopropoxy. In an exemplary embodiment, $Y^3$ is unsubstituted $C_4$ alkoxy. In an exemplary embodiment, $Y^3$ is unsubstituted $C_5$ alkoxy. In an exemplary embodiment, $Y^3$ is unsubstituted $C_6$ alkoxy.

In an exemplary embodiment, the compound of the invention has a structure which is selected from the group consisting of:

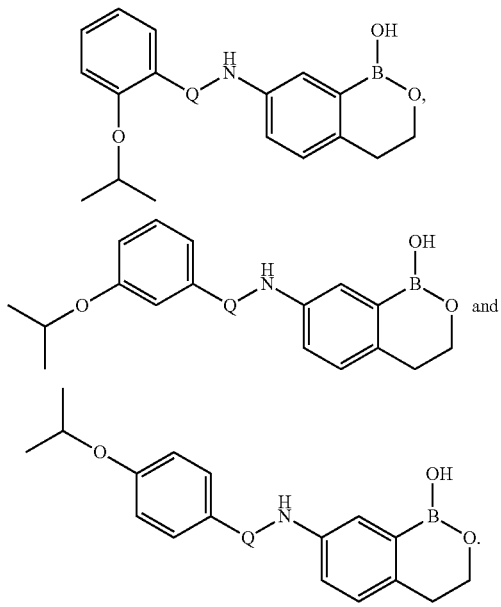

and Q is as described herein. In an exemplary embodiment, Q is $SO_2$. In an exemplary embodiment, Q is C=O.

In an exemplary embodiment, the compound of the invention has a structure which is selected from the group consisting of:

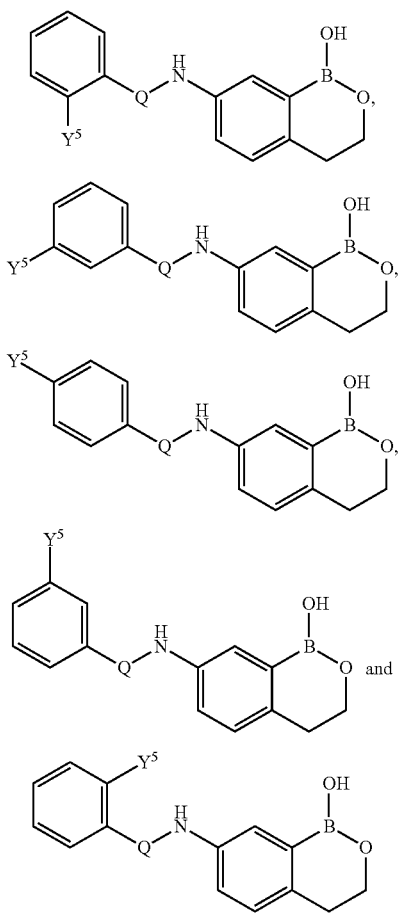

wherein $Y^5$ is halosubstituted alkoxy, and Q is as described herein. In an exemplary embodiment, Q is $SO_2$. In an exemplary embodiment, Q is C=O. In an exemplary embodiment, $Y^5$ is halosubstituted $C_1$ alkoxy. In an exemplary embodiment, $Y^5$ is halosubstituted $C_2$ alkoxy. In an exemplary embodiment, $Y^5$ is halosubstituted $C_3$ alkoxy. In an exemplary embodiment, $Y^5$ is halosubstituted $C_4$ alkoxy. In an exemplary embodiment, $Y^5$ is halosubstituted $C_5$ alkoxy. In an exemplary embodiment, $Y^5$ is halosubstituted $C_6$ alkoxy. In an exemplary embodiment, $Y^5$ is fluoro-substituted $C_1$-$C_6$ alkoxy. In an exemplary embodiment, $Y^5$ is substituted with one or two or three halogens. In an exemplary embodiment, $Y^5$ is trifluoro-substituted $C_1$-$C_6$ alkoxy. In an exemplary embodiment, $Y^5$ is trifluoromethoxy.

In an exemplary embodiment, the compound of the invention has a structure which is selected from the group consisting of:

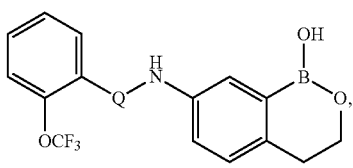

-continued

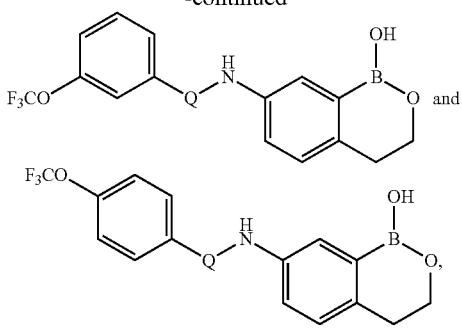

wherein Q is as described herein. In an exemplary embodiment, Q is SO₂. In an exemplary embodiment, Q is C=O.

In an exemplary embodiment, the compound of the invention has a structure which is selected from the group consisting of:

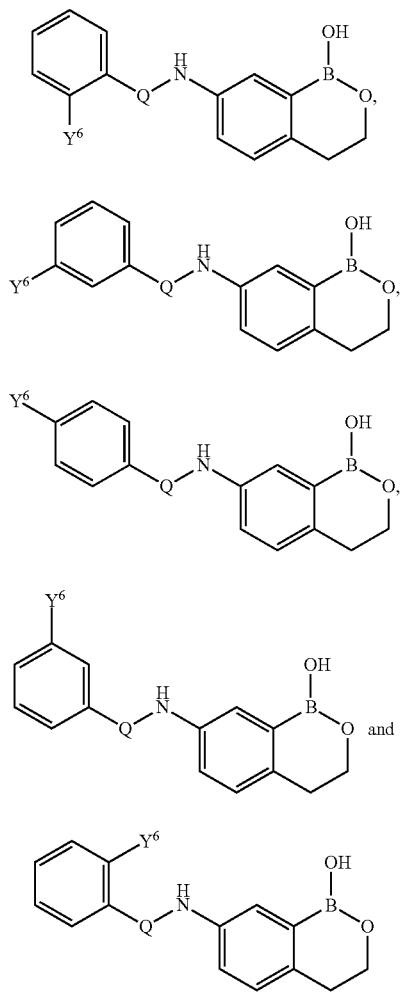

wherein $Y^6$ is halosubstituted alkylthio, and Q is as described herein. In an exemplary embodiment, Q is SO₂. In an exemplary embodiment, Q is C=O. In an exemplary embodiment, $Y^6$ is halosubstituted $C_1$ alkylthio. In an exemplary embodiment, $Y^6$ is halosubstituted $C_2$ alkylthio. In an exemplary embodiment, $Y^6$ is halosubstituted $C_3$ alkylthio. In an exemplary embodiment, $Y^6$ is halosubstituted $C_4$ alkylthio. In an exemplary embodiment, $Y^6$ is halosubstituted $C_5$ alkylthio. In an exemplary embodiment, $Y^6$ is halosubstituted $C_6$ alkylthio. In an exemplary embodiment, $Y^6$ is fluoro-substituted $C_1$-$C_6$ alkylthio. In an exemplary embodiment, $Y^6$ is substituted with one or two or three halogens. In an exemplary embodiment, $Y^6$ is trifluoro-substituted $C_1$-$C_6$ alkylthio. In an exemplary embodiment, $Y^5$ is trifluoromethylthio.

In an exemplary embodiment, the compound of the invention is selected from the group consisting of:

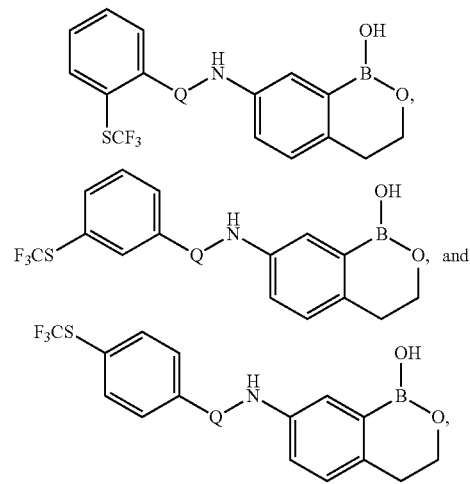

wherein Q is as described herein. In an exemplary embodiment, Q is SO₂. In an exemplary embodiment, Q is C=O. In an exemplary embodiment, the compound of the invention is:

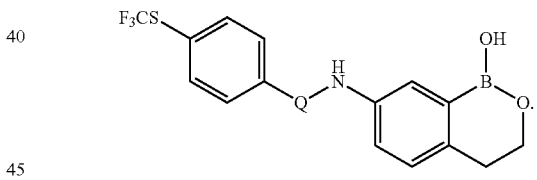

In an exemplary embodiment, the compound of the invention has a structure according to the following formula:

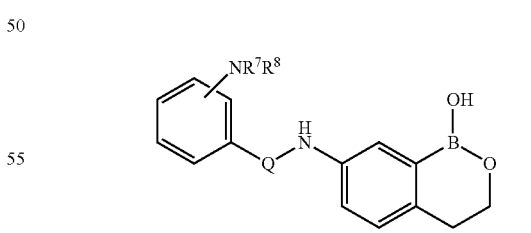

wherein $R^7$ is unsubstituted alkyl and $R^8$ is unsubstituted alkyl, Q is as described herein, or a salt thereof. In an exemplary embodiment, Q is SO₂. In an exemplary embodiment, Q is C=O.

In an exemplary embodiment, the compound of the invention has a structure which is selected from the group consisting of:

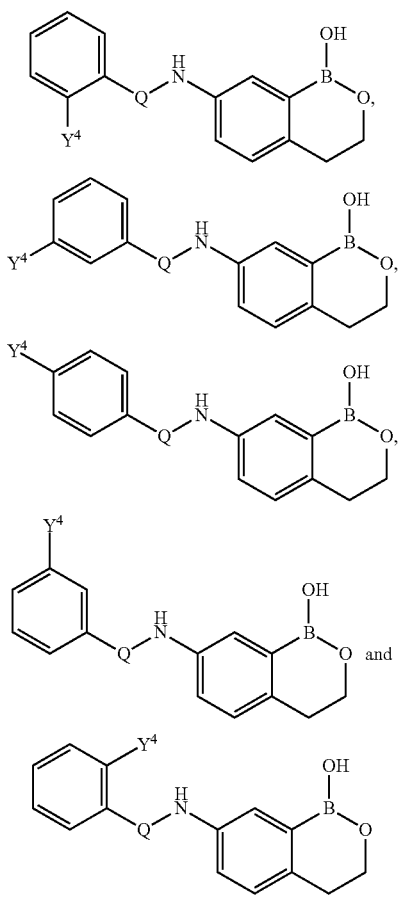

wherein $Y^4$ is —NHC(O)$R^4$, wherein $R^4$ is unsubstituted alkyl, and Q is as described herein. In an exemplary embodiment, Q is SO$_2$. In an exemplary embodiment, Q is C=O. In an exemplary embodiment, $R^4$ is unsubstituted $C_1$ alkyl. In an exemplary embodiment, $R^4$ is unsubstituted $C_2$ alkyl. In an exemplary embodiment, $R^4$ is unsubstituted $C_3$ alkyl. In an exemplary embodiment, $R^4$ is unsubstituted $C_4$ alkyl. In an exemplary embodiment, $R^4$ is unsubstituted $C_5$ alkyl. In an exemplary embodiment, $R^4$ is unsubstituted $C_6$ alkyl.

In an exemplary embodiment, the compound of the invention has a structure which is selected from the group consisting of:

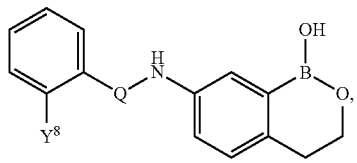

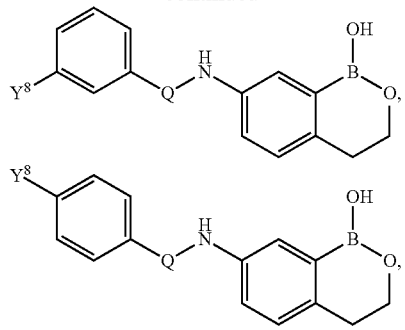

-continued

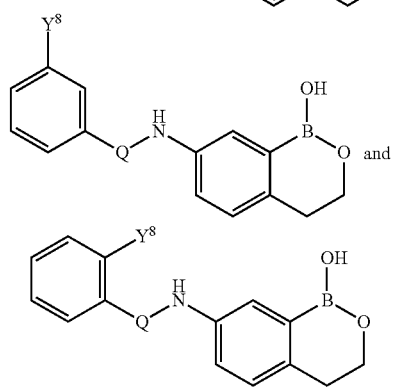

wherein $Y^8$ is —S(O)$_2$NHCHN$R^7R^8$, wherein $R^7$ is unsubstituted alkyl, $R^8$ is unsubstituted alkyl, and Q is as described herein. In an exemplary embodiment, Q is SO$_2$. In an exemplary embodiment, Q is C=O. In an exemplary embodiment, $R^7$ is unsubstituted $C_1$ alkyl and $R^8$ is unsubstituted alkyl. In an exemplary embodiment, $R^7$ is unsubstituted $C_2$ alkyl and $R^8$ is unsubstituted alkyl. In an exemplary embodiment, $R^7$ is unsubstituted $C_3$ alkyl and $R^8$ is unsubstituted alkyl. In an exemplary embodiment, $R^7$ is unsubstituted $C_4$ alkyl and $R^8$ is unsubstituted alkyl. In an exemplary embodiment, $R^7$ is unsubstituted $C_5$ alkyl and $R^8$ is unsubstituted alkyl. In an exemplary embodiment, $R^7$ is unsubstituted $C_6$ alkyl and $R^8$ is unsubstituted alkyl. In an exemplary embodiment, $Y^8$ is —S(O)$_2$NHCHN(CH$_3$)$_2$.

In an exemplary embodiment, the compound of the invention has a structure according to the following formula:

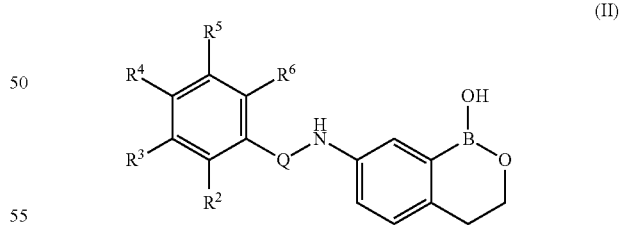

(II)

wherein $R^2$, $R^3$, $R^4$, $R^5$ and $R^6$ are according to the entries in the following table, or a salt thereof.

| | $R^2$ | $R^3$ | $R^4$ | $R^5$ | $R^6$ |
|---|---|---|---|---|---|
| 1 | F | H | H | H | H |
| 2 | H | F | H | H | H |
| 3 | H | H | F | H | H |
| 4 | H | H | H | F | H |

-continued

| | R² | R³ | R⁴ | R⁵ | R⁶ |
|---|---|---|---|---|---|
| 5 | H | H | H | H | F |
| 6 | Cl | H | H | H | H |
| 7 | H | Cl | H | H | H |
| 8 | H | H | Cl | H | H |
| 9 | H | H | H | Cl | H |
| 10 | H | H | H | H | Cl |
| 11 | Br | H | H | H | H |
| 12 | H | Br | H | H | H |
| 13 | H | H | Br | H | H |
| 14 | H | H | H | Br | H |
| 15 | H | H | H | H | Br |
| 16 | I | H | H | H | H |
| 17 | H | I | H | H | H |
| 18 | H | H | I | H | H |
| 19 | H | H | H | I | H |
| 20 | H | H | H | H | I |
| 21 | CN | H | H | H | H |
| 22 | H | CN | H | H | H |
| 23 | H | H | CN | H | H |
| 24 | H | H | H | CN | H |
| 25 | H | H | H | H | CN |
| 26 | NO₂ | H | H | H | H |
| 27 | H | NO₂ | H | H | H |
| 28 | H | H | NO₂ | H | H |
| 29 | H | H | H | NO₂ | H |
| 30 | H | H | H | H | NO₂ |
| 31 | Ph | H | H | H | H |
| 32 | H | Ph | H | H | H |
| 33 | H | H | Ph | H | H |
| 34 | H | H | H | Ph | H |
| 35 | H | H | H | H | Ph |
| 36 | —CH₃ | H | H | H | H |
| 37 | H | —CH₃ | H | H | H |
| 38 | H | H | —CH₃ | H | H |
| 39 | H | H | H | —CH₃ | H |
| 40 | H | H | H | H | —CH₃ |
| 41 | —CH₂CH₃ | H | H | H | H |
| 42 | H | —CH₂CH₃ | H | H | H |
| 43 | H | H | —CH₂CH₃ | H | H |
| 44 | H | H | H | —CH₂CH₃ | H |
| 45 | H | H | H | H | —CH₂CH₃ |
| 46 | —CF₃ | H | H | H | H |
| 47 | H | —CF₃ | H | H | H |
| 48 | H | H | —CF₃ | H | H |
| 49 | H | H | H | —CF₃ | H |
| 50 | H | H | H | H | —CF₃ |
| 51 | —OCH₃ | H | H | H | H |
| 52 | H | —OCH₃ | H | H | H |
| 53 | H | H | —OCH₃ | H | H |
| 54 | H | H | H | —OCH₃ | H |
| 55 | H | H | H | H | —OCH₃ |
| 56 | —OCH₂CH₃ | H | H | H | H |
| 57 | H | —OCH₂CH₃ | H | H | H |
| 58 | H | H | —OCH₂CH₃ | H | H |
| 59 | H | H | H | —OCH₂CH₃ | H |
| 60 | H | H | H | H | —OCH₂CH₃ |
| 61 | —OCH(CH₃)₂ | H | H | H | H |
| 62 | H | —OCH(CH₃)₂ | H | H | H |
| 63 | H | H | —OCH(CH₃)₂ | H | H |
| 64 | H | H | H | —OCH(CH₃)₂ | H |
| 65 | H | H | H | H | —OCH(CH₃)₂ |
| 66 | —NR⁷R⁸ | H | H | H | H |
| 67 | H | —NR⁷R⁸ | H | H | H |
| 68 | H | H | —NR⁷R⁸ | H | H |
| 69 | H | H | H | —NR⁷R⁸ | H |
| 70 | H | H | H | H | —NR⁷R⁸ |
| 71 | —NH₂ | H | H | H | H |
| 72 | H | —NH₂ | H | H | H |
| 73 | H | H | —NH₂ | H | H |
| 74 | H | H | H | —NH₂ | H |
| 75 | H | H | H | H | —NH₂ |
| 76 | —N(CH₃)R⁸ | H | H | H | H |
| 77 | H | —N(CH₃)R⁸ | H | H | H |
| 78 | H | H | —N(CH₃)R⁸ | H | H |
| 79 | H | H | H | —N(CH₃)R⁸ | H |
| 80 | H | H | H | H | —N(CH₃)R⁸ |
| 81 | —N(CH₃)₂ | H | H | H | H |
| 82 | H | —N(CH₃)₂ | H | H | H |

-continued

| | R² | R³ | R⁴ | R⁵ | R⁶ |
|---|---|---|---|---|---|
| 83 | H | H | —N(CH₃)₂ | H | H |
| 84 | H | H | H | —N(CH₃)₂ | H |
| 85 | H | H | H | H | —N(CH₃)₂ |
| 86 | —NHC(O)CH₃ | H | H | H | H |
| 87 | H | —NHC(O)CH₃ | H | H | H |
| 88 | H | H | —NHC(O)CH₃ | H | H |
| 89 | H | H | H | —NHC(O)CH₃ | H |
| 90 | H | H | H | H | —NHC(O)CH₃ |

For any of the entries in the above table, Q is SO₂. For any of the entries in the above table, Q is C=O.

In an exemplary embodiment, the compound of the invention has a structure which is selected from the group consisting of:

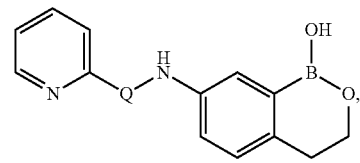

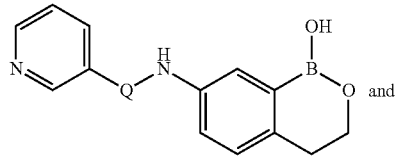

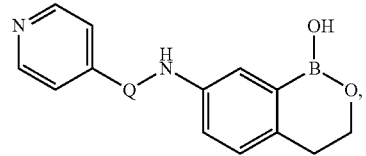

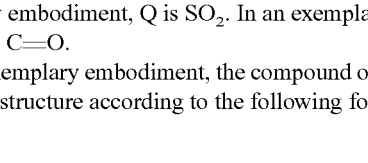

wherein Q is as described herein, or a salt thereof. In an exemplary embodiment, Q is SO₂. In an exemplary embodiment, Q is C=O.

In an exemplary embodiment, the compound of the invention has a structure according to the following formula:

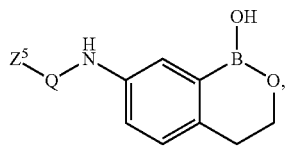

wherein Z⁵ is unsubstituted pyrimidinyl or unsubstituted pyrazinyl or unsubstituted pyridazinyl, wherein Q is as described herein, or a salt thereof. In an exemplary embodiment, Q is SO₂. In an exemplary embodiment, Q is C=O. In an exemplary embodiment, the compound of the invention has a structure which is selected from the group consisting of:

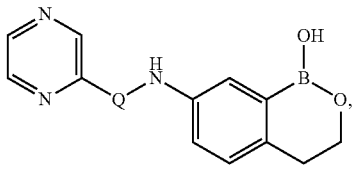

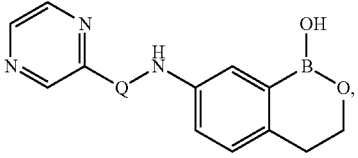

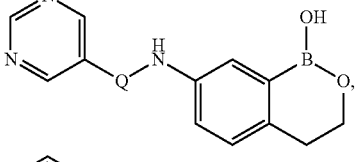

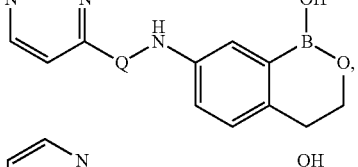

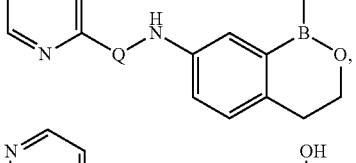

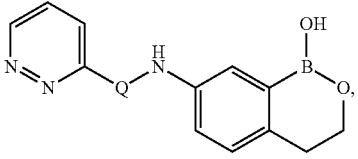

wherein Q is as described herein, or a salt thereof. In an exemplary embodiment, Q is SO₂. In an exemplary embodiment, Q is C=O.

In an exemplary embodiment, the compound of the invention has a structure according to the following formula:

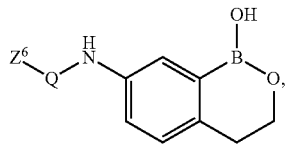

wherein Q is as described herein, $Z^6$ is halosubstituted pyridazinyl, or a salt thereof. In an exemplary embodiment, Q is $SO_2$. In an exemplary embodiment, Q is C=O. In an exemplary embodiment, $Z^6$ is pyridazinyl, substituted with one halogen. In an exemplary embodiment, $Z^6$ is pyridazinyl, substituted with two halogens. In an exemplary embodiment, $Z^6$ is pyridazinyl, substituted with two chlorines. In an exemplary embodiment, the compound of the invention has a structure which is:

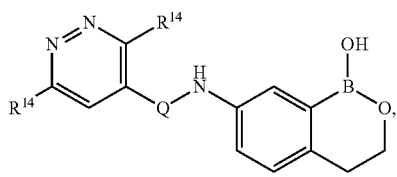

wherein each $R^{14}$ is chlorine or fluorine, wherein Q is as described herein, or a salt thereof. In an exemplary embodiment, each $R^{14}$ is chlorine. In an exemplary embodiment, Q is $SO_2$. In an exemplary embodiment, Q is C=O.

In an exemplary embodiment, the compound of the invention has a structure according to the following formula:

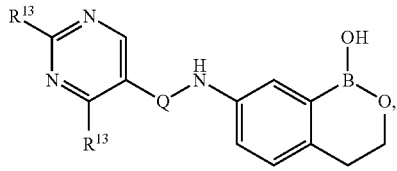

wherein each $R^{13}$ is independently selected from the group selected from H, —SH and —OH, wherein Q is as described herein, or a salt thereof. In an exemplary embodiment, each $R^{13}$ is —SH or —OH. In an exemplary embodiment, Q is $SO_2$. In an exemplary embodiment, Q is C=O.

In an exemplary embodiment, the compound of the invention has a structure according to the following formula:

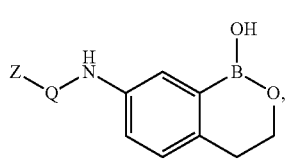

wherein Z is thiophenyl, wherein Q is as described herein, or a salt thereof. In an exemplary embodiment, Q is $SO_2$. In an exemplary embodiment, Q is C=O. In an exemplary embodiment, the compound of the invention has a structure which is:

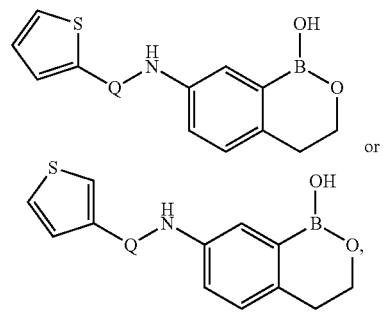

wherein Q is as described herein. In an exemplary embodiment, Q is $SO_2$. In an exemplary embodiment, Q is C=O.

In an exemplary embodiment, the compound of the invention has a structure according to the following formula:

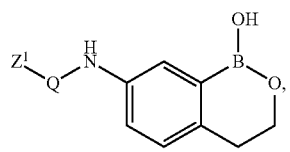

wherein $Z^1$ is unsubstituted alkylthiophenyl, Q is as described herein, or a salt thereof. In an exemplary embodiment, Q is $SO_2$. In an exemplary embodiment, Q is C=O. In an exemplary embodiment, the compound of the invention has a structure which is

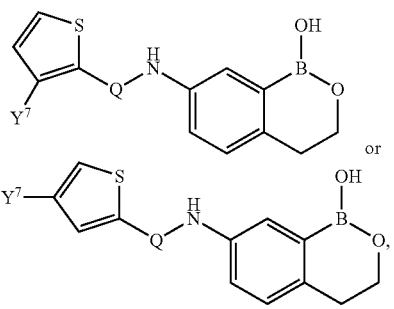

wherein $Y^7$ is unsubstituted alkyl, Q is as described herein, or a salt thereof. In an exemplary embodiment, Q is $SO_2$. In an exemplary embodiment, Q is C=O. In an exemplary embodiment, $Y^7$ is unsubstituted $C_1$ alkyl. In an exemplary embodiment, $Y^7$ is unsubstituted $C_2$ alkyl. In an exemplary embodiment, $Y^7$ is unsubstituted $C_3$ alkyl. In an exemplary embodiment, $Y^7$ is unsubstituted $C_4$ alkyl. In an exemplary embodiment, $Y^7$ is unsubstituted $C_5$ alkyl. In an exemplary embodiment, $Y^7$ is unsubstituted $C_6$ alkyl.

In an exemplary embodiment, the compound of the invention has a structure according to the following formula:

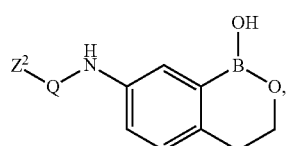

wherein $Z^2$ is unsubstituted benzothiophenyl, Q is as described herein, or a salt thereof. In an exemplary embodiment, Q is $SO_2$. In an exemplary embodiment, Q is C=O.

In an exemplary embodiment, the compound of the invention has a structure according to the following formula:

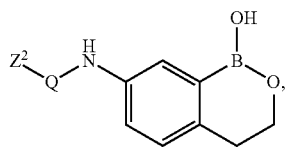

wherein $Z^2$ is halosubstituted benzothiophenyl, Q is as described herein, or a salt thereof. In an exemplary embodiment, Q is $SO_2$. In an exemplary embodiment, Q is C=O. In an exemplary embodiment, $Z^2$ is benzothiophenyl substituted with chloro. In an exemplary embodiment, $Z^2$ is benzothiophenyl substituted with fluoro. In an exemplary embodiment, $Z^2$ is benzothiophenyl substituted with one halogen. In an exemplary embodiment, $Z^2$ is benzothiophenyl substituted with two halogens. In an exemplary embodiment, $Z^2$ is benzothiophenyl substituted with two fluorines. In an exemplary embodiment, $Z^2$ is benzothiophenyl substituted with two chlorines. In an exemplary embodiment, $Z^2$ is benzothiophenyl substituted with a fluorine and a chlorine. In an exemplary embodiment, the compound of the invention is:

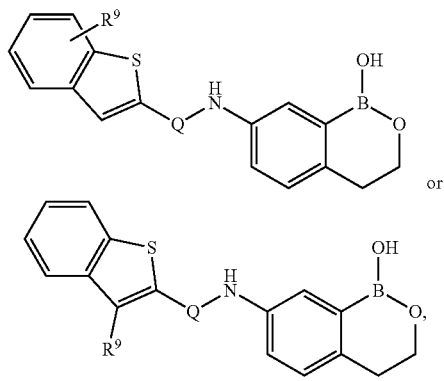

wherein $R^9$ is halogen, Q is as described herein, or a salt thereof. In an exemplary embodiment, the compound of the invention is:

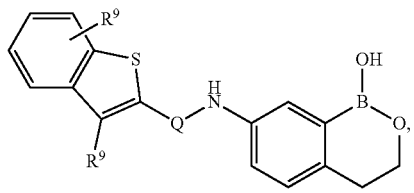

wherein each $R^9$ is an independently selected halogen, Q is as described herein, or a salt thereof. In an exemplary embodiment, Q is $SO_2$. In an exemplary embodiment, Q is C=O.

In an exemplary embodiment, the compound of the invention has a structure according to the following formula:

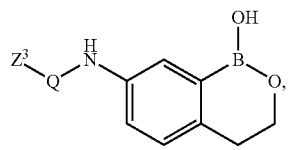

wherein $Z^3$ is unsubstituted oxazolyl, Q is as described herein, or a salt thereof. In an exemplary embodiment, Q is $SO_2$. In an exemplary embodiment, Q is C=O. In an exemplary embodiment, the compound of the invention has a structure which is

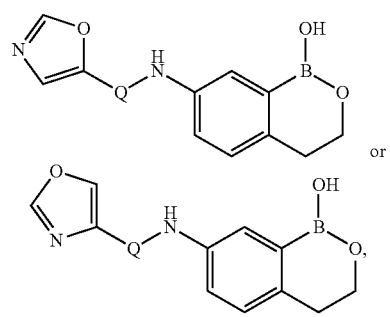

wherein Q is as described herein, or a salt thereof. In an exemplary embodiment, Q is $SO_2$. In an exemplary embodiment, Q is C=O.

In an exemplary embodiment, the compound of the invention has a structure according to the following formula:

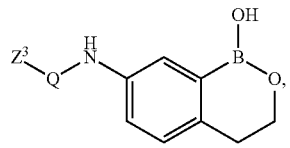

wherein $Z^3$ is unsubstituted alkyl oxazolyl, Q is as described herein, or a salt thereof. In an exemplary embodiment, Q is $SO_2$. In an exemplary embodiment, Q is C=O. In an exemplary embodiment, the compound of the invention has a structure which is

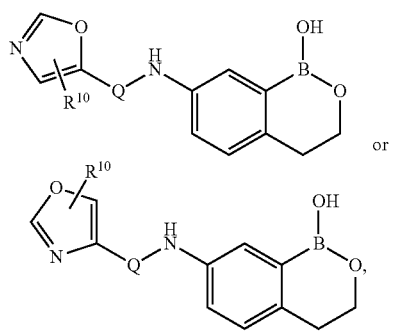

wherein $R^{10}$ is unsubstituted alkyl, Q is as described herein, or a salt thereof. In an exemplary embodiment, Q is $SO_2$. In an exemplary embodiment, Q is C=O. In an exemplary embodiment, the compound of the invention has a structure according to the following formula:

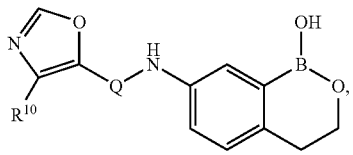

wherein $R^{10}$ is unsubstituted alkyl, Q is as described herein, or a salt thereof. In an exemplary embodiment, $R^{10}$ is $C_1$ or $C_2$ or $C_3$ or $C_4$ or $C_5$ or $C_6$ alkyl. In an exemplary embodiment, Q is $SO_2$. In an exemplary embodiment, Q is C=O.

In an exemplary embodiment, the compound of the invention has a structure according to the following formula:

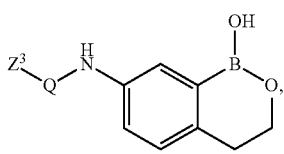

wherein $Z^3$ is unsubstituted isoxazolyl, Q is as described herein, or a salt thereof. In an exemplary embodiment, Q is $SO_2$. In an exemplary embodiment, Q is C=O. In an exemplary embodiment, the compound of the invention has a structure which is

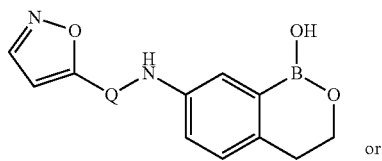

wherein Q is as described herein, or a salt thereof.

In an exemplary embodiment, the compound of the invention has a structure according to the following formula:

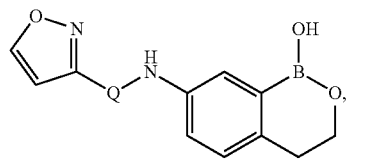

wherein $Z^3$ is unsubstituted alkyl isoxazolyl, Q is as described herein, or a salt thereof. In an exemplary embodiment, Q is $SO_2$. In an exemplary embodiment, Q is C=O. In an exemplary embodiment, the compound of the invention has a structure which is

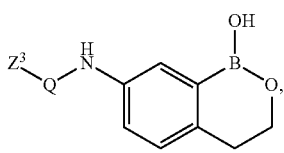

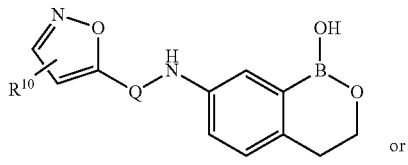

wherein $R^{10}$ is unsubstituted $C_1$-$C_6$ alkyl, Q is as described herein, or a salt thereof. In an exemplary embodiment, Q is $SO_2$. In an exemplary embodiment, Q is C=O. In an exemplary embodiment, the compound of the invention has a structure according to the following formula:

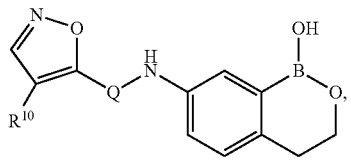

wherein $R^{10}$ is unsubstituted alkyl, Q is as described herein, or a salt thereof. In an exemplary embodiment, $R^{10}$ is unsubstituted $C_1$ alkyl. In an exemplary embodiment, $R^{10}$ is unsubstituted $C_2$ alkyl. In an exemplary embodiment, $R^{10}$ is unsubstituted $C_3$ alkyl. In an exemplary embodiment, $R^{10}$ is unsubstituted $C_4$ alkyl. In an exemplary embodiment, $R^{10}$ is unsubstituted $C_5$ alkyl. In an exemplary embodiment, $R^{10}$ is unsubstituted $C_6$ alkyl.

In an exemplary embodiment, the compound of the invention has a structure according to the following formula:

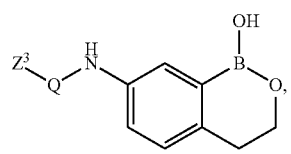

wherein $Z^3$ is unsubstituted thiazolyl, Q is as described herein, or a salt thereof. In an exemplary embodiment, Q is $SO_2$. In an exemplary embodiment, Q is C=O. In an exemplary embodiment, the compound of the invention has a structure which is

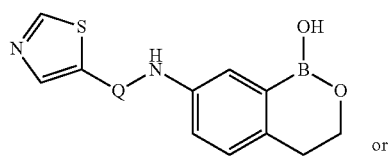

-continued

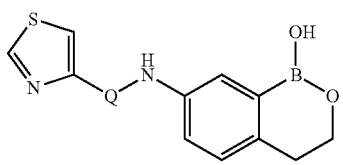

wherein Q is as described herein, or a salt thereof.

In an exemplary embodiment, the compound of the invention has a structure according to the following formula:

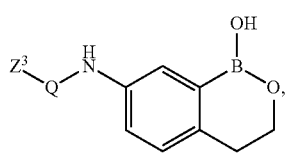

wherein $Z^3$ is unsubstituted alkyl thiazolyl, Q is as described herein, or a salt thereof. In an exemplary embodiment, Q is $SO_2$. In an exemplary embodiment, Q is C=O. In an exemplary embodiment, the compound of the invention has a structure which is:

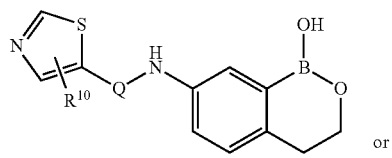

wherein $R^{10}$ is unsubstituted alkyl, Q is as described herein, or a salt thereof. In an exemplary embodiment, Q is $SO_2$. In an exemplary embodiment, Q is C=O. In an exemplary embodiment, the compound of the invention has a structure which is:

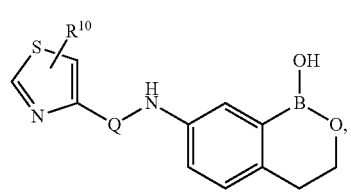

wherein $R^{10}$ is unsubstituted alkyl, Q is as described herein, or a salt thereof. In an exemplary embodiment, $R^{10}$ is $C_1$ or $C_2$ or $C_3$ or $C_4$ or $C_5$ or $C_6$ alkyl. In an exemplary embodiment, Q is $SO_2$. In an exemplary embodiment, Q is C=O.

In an exemplary embodiment, the compound of the invention has a structure according to the following formula:

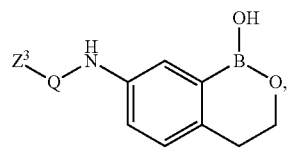

wherein $Z^3$ is unsubstituted pyrazolyl, Q is as described herein, or a salt thereof. In an exemplary embodiment, Q is $SO_2$. In an exemplary embodiment, Q is C=O. In an exemplary embodiment, the compound of the invention has a structure which is

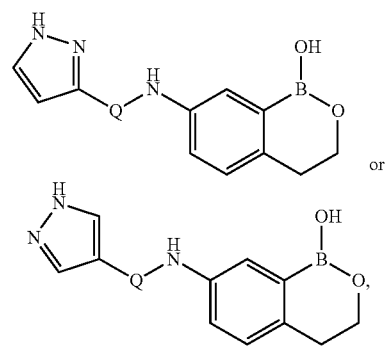

In an exemplary embodiment, the compound of the invention has a structure according to the following formula:

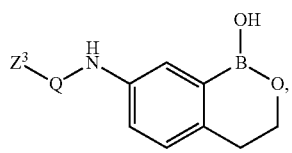

wherein $Z^3$ is selected from the group consisting of unsubstituted alkyl pyrrolyl, unsubstituted phenyl pyrrolyl and unsubstituted phenyl (unsubstituted alkyl) pyrrolyl, Q is as described herein, or a salt thereof. In an exemplary embodiment, Q is $SO_2$. In an exemplary embodiment, Q is C=O. In an exemplary embodiment, the compound of the invention has a structure which is:

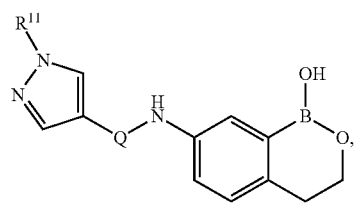

wherein each $R^{11}$ is independently selected from unsubstituted $C_1$-$C_6$ alkyl or phenyl, Q is as described herein, or a salt thereof. In an exemplary embodiment, Q is $SO_2$. In an exemplary embodiment, Q is C=O. In an exemplary embodiment, the compound of the invention has a structure which is

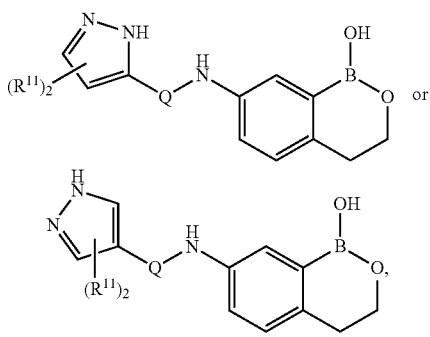

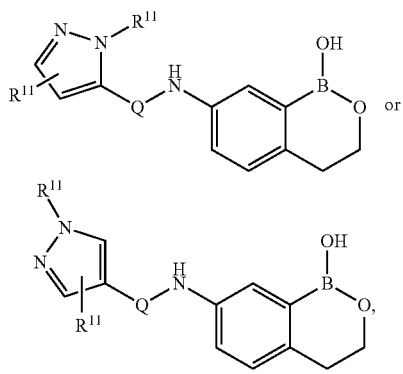

wherein each $R^{11}$ is independently selected from unsubstituted $C_1$-$C_6$ alkyl or phenyl, Q is as described herein, or a salt thereof. In an exemplary embodiment, Q is $SO_2$. In an exemplary embodiment, Q is C=O. In an exemplary embodiment, the compound of the invention has a structure which is

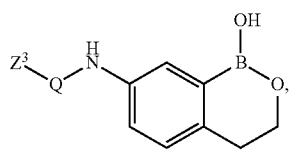

wherein $Z^3$ is unsubstituted furanyl, Q is as described herein, or a salt thereof. In an exemplary embodiment, Q is $SO_2$. In an exemplary embodiment, Q is C=O. In an exemplary embodiment, the compound is:

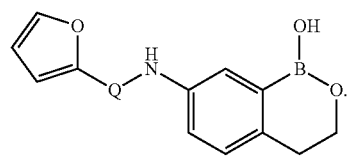

In an exemplary embodiment, the compound of the invention has a structure according to the following formula:

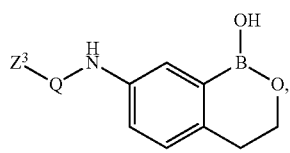

wherein Q is as described herein, or a salt thereof. In an exemplary embodiment, Q is $SO_2$. In an exemplary embodiment, Q is C=O. In an exemplary embodiment, $R^{11}$ is unsubstituted $C_1$ alkyl. In an exemplary embodiment, $R^{11}$ is unsubstituted $C_2$ alkyl. In an exemplary embodiment, $R^{11}$ is unsubstituted $C_3$ alkyl. In an exemplary embodiment, $R^{11}$ is unsubstituted $C_4$ alkyl. In an exemplary embodiment, $R^{11}$ is unsubstituted $C_5$ alkyl. In an exemplary embodiment, $R^{11}$ is unsubstituted $C_6$ alkyl. In an exemplary embodiment, $R^{11}$ is unsubstituted phenyl. In an exemplary embodiment, the compound of the invention has a structure according to the following formula:

wherein $Z^3$ is unsubstituted alkylfuranyl, Q is as described herein, or a salt thereof. In an exemplary embodiment, Q is $SO_2$. In an exemplary embodiment, Q is C=O. In an exemplary embodiment, the compound of the invention is:

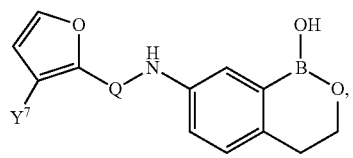

wherein $Y^7$ is unsubstituted alkyl, Q is as described herein, or a salt thereof. In an exemplary embodiment, Q is $SO_2$. In an exemplary embodiment, Q is C=O. In an exemplary embodiment, $Y^7$ is unsubstituted $C_1$ alkyl. In an exemplary embodiment, $Y^7$ is unsubstituted $C_2$ alkyl. In an exemplary embodiment, $Y^7$ is unsubstituted $C_3$ alkyl. In an exemplary embodiment, $Y^7$ is unsubstituted $C_4$ alkyl. In an exemplary embodiment, $Y^7$ is unsubstituted $C_5$ alkyl. In an exemplary embodiment, $Y^7$ is unsubstituted $C_6$ alkyl.

In an exemplary embodiment, the compound of the invention has a structure according to the following formula:

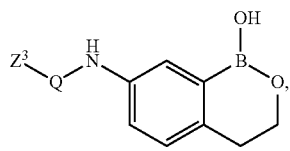

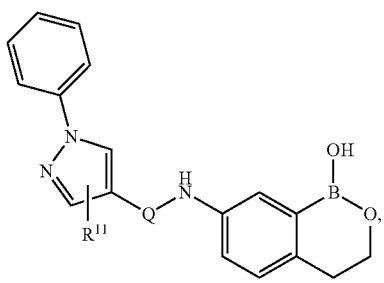

Q is as described herein, or a salt thereof. In an exemplary embodiment, Q is $SO_2$. In an exemplary embodiment, Q is C=O.

In an exemplary embodiment, the compound of the invention has a structure according to the following formula:

wherein $Z^3$ is unsubstituted pyrrole, Q is as described herein, or a salt thereof. In an exemplary embodiment, Q is SO$_2$. In an exemplary embodiment, Q is C=O. In an exemplary embodiment, the compound is:

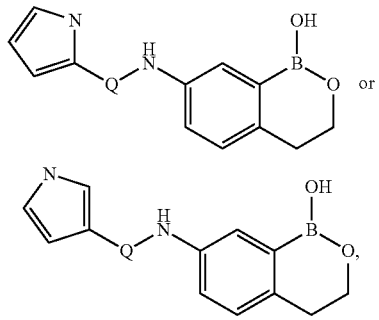

or a salt thereof.

In an exemplary embodiment, the compound of the invention has a structure according to the following formula:

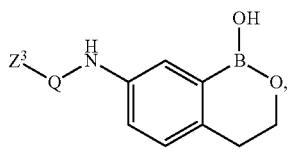

wherein $Z^3$ is unsubstituted alkyl pyrrole, Q is as described herein, or a salt thereof. In an exemplary embodiment, Q is SO$_2$. In an exemplary embodiment, Q is C=O. In an exemplary embodiment, the compound is:

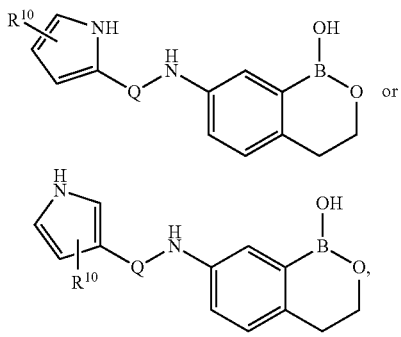

wherein $R^{10}$ is unsubstituted alkyl, Q is as described herein, or a salt thereof. In an exemplary embodiment, Q is SO$_2$. In an exemplary embodiment, Q is C=O. In an exemplary embodiment, the compound is:

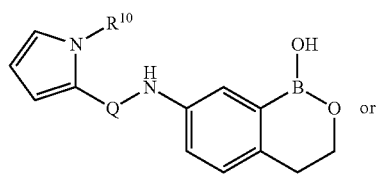

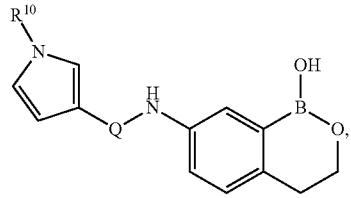

wherein $R^{10}$ is unsubstituted alkyl, Q is as described herein, or a salt thereof. In an exemplary embodiment, Q is SO$_2$. In an exemplary embodiment, Q is C=O. In an exemplary embodiment, $R^{10}$ is unsubstituted $C_1$ alkyl. In an exemplary embodiment, $R^{10}$ is unsubstituted $C_2$ alkyl. In an exemplary embodiment, $R^{10}$ is unsubstituted $C_3$ alkyl. In an exemplary embodiment, $R^{10}$ is unsubstituted $C_4$ alkyl. In an exemplary embodiment, $R^{10}$ is unsubstituted $C_5$ alkyl. In an exemplary embodiment, $R^{10}$ is unsubstituted $C_6$ alkyl.

In an exemplary embodiment, the compound of the invention has a structure which is selected from the group consisting of

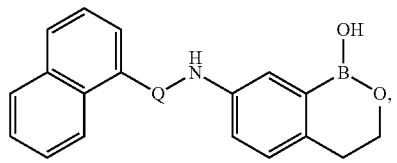

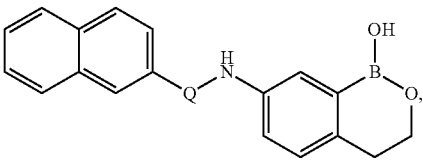

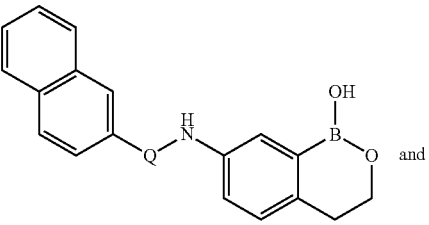

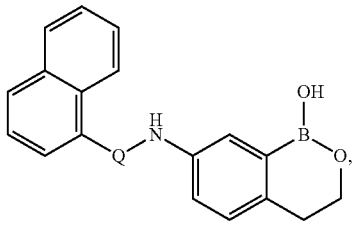

Q is as described herein, or a salt thereof. In an exemplary embodiment, Q is SO$_2$. In an exemplary embodiment, Q is C=O.

In an exemplary embodiment, the compound of the invention has a structure which is selected from the group consisting of

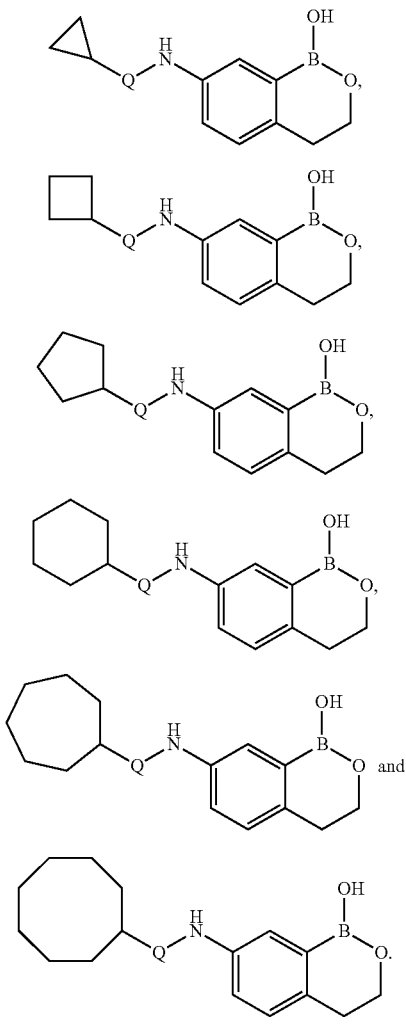

wherein Q is as described herein, or a salt thereof or a salt thereof. In an exemplary embodiment, Q is SO$_2$. In an exemplary embodiment, Q is C=O.

In an exemplary embodiment, the compound of the invention has a structure according to the following formula:

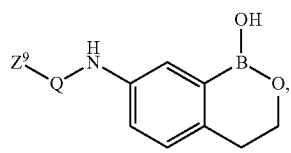

wherein Z$^9$ is unsubstituted alkyl, Q is as described herein, or a salt thereof. In an exemplary embodiment, Q is SO$_2$. In an exemplary embodiment, Q is C=O. In an exemplary embodiment, Z$^9$ is unsubstituted C$_1$ or C$_2$ or C$_3$ or C$_4$ or C$_5$ or C$_6$ alkyl. In an exemplary embodiment, Z$^9$ is methyl. In an exemplary embodiment, Z$^9$ is unsubstituted C$_4$ alkyl. In an exemplary embodiment, Z$^9$ is n-butyl or sec-butyl or isobutyl or tert-butyl. In an exemplary embodiment, Z$^9$ is tert-butyl.

In an exemplary embodiment, the compound of the invention has a structure according to the following formula:

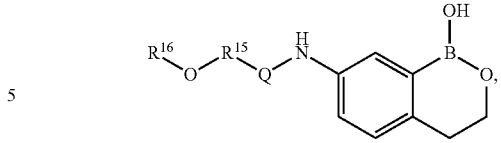

wherein R$^{15}$ is unsubstituted alkyl and R$^{16}$ is H or phenyl substituted alkyl, Q is as described herein, or a salt thereof. In an exemplary embodiment, Q is SO$_2$. In an exemplary embodiment, Q is C=O. In an exemplary embodiment, R$^{15}$ is unsubstituted C$_1$ or C$_2$ or C$_3$ or C$_4$ or C$_5$ or C$_6$ alkyl. In an exemplary embodiment, R$^{15}$ is unsubstituted C$_3$ alkyl. In an exemplary embodiment, R$^{16}$ is benzyl.

In an exemplary embodiment, the compound of the invention has a structure according to the following formula:

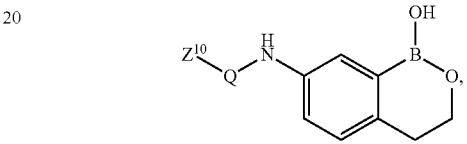

wherein Z$^{10}$ is hydroxy-substituted alkyl, Q is as described herein, or a salt thereof. In an exemplary embodiment, Q is SO$_2$. In an exemplary embodiment, Q is C=O. In an exemplary embodiment, Z$^{10}$ is hydroxy substituted C$_1$ or C$_2$ or C$_3$ or C$_4$ or C$_5$ or C$_6$ alkyl.

In an exemplary embodiment, the compound of the invention has a structure according to the following formula:

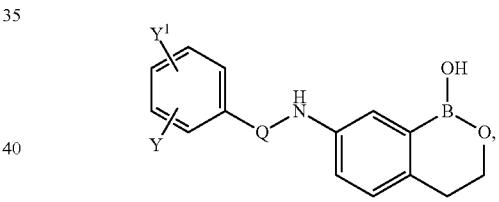

wherein Y$^1$ is a halogen, Y is halo-substituted alkyl, Q is as described herein, or a salt thereof. In an exemplary embodiment, Q is SO$_2$. In an exemplary embodiment, Q is C=O. In an exemplary embodiment, Y is halo-substituted C$_1$-C$_6$ alkyl. In an exemplary embodiment, Y is fluoro-substituted C$_1$-C$_6$ alkyl, and Y$^1$ is as described herein. In an exemplary embodiment, Y is trifluoro-substituted C$_1$-C$_6$ alkyl, Y$^1$ is as described herein. In an exemplary embodiment, Y is C$_1$-C$_6$ alkyl, substituted with one halogen, Y$^1$ is as described herein. In an exemplary embodiment, Y is C$_1$-C$_6$ alkyl, substituted with two halogens, Y$^1$ is as described herein. In an exemplary embodiment, Y is C$_1$-C$_6$ alkyl, substituted with three halogens, Y$^1$ is as described herein. In an exemplary embodiment, Y is C$_1$-C$_6$ alkyl, substituted with four halogens, Y$^1$ is as described herein. In an exemplary embodiment, Y is C$_1$-C$_6$ alkyl, substituted with one fluorine, Y$^1$ is as described herein. In an exemplary embodiment, Y is C$_1$-C$_6$ alkyl, substituted with two fluorines, Y$^1$ is as described herein. In an exemplary embodiment, Y is C$_1$-C$_6$ alkyl, substituted with three fluorines, Y$^1$ is as described herein. In an exemplary embodiment, Y is C$_1$-C$_6$ alkyl, substituted with four fluorines, Y$^1$ is as described herein. In an exemplary embodiment, Y is C$_1$-C$_6$ alkyl, substituted with one chlorine, Y$^1$ is as described herein. In an exemplary embodiment, Y is C$_1$-C$_6$ alkyl, substituted with two chlorines, $Y^1$ is as described herein. In an exemplary embodiment, Y is $C_1$-$C_6$ alkyl, substituted with three chlorines, $Y^1$ is as described herein. In an exemplary embodiment, Y is $C_1$-$C_6$ alkyl, substituted with four chlorines, $Y^1$ is as described herein. In an exemplary embodiment, Y is $C_1$-$C_6$ alkyl, substituted with a combination of two different halogens, $Y^1$ is as described herein. In an exemplary embodiment, Y is $C_1$-$C_6$ alkyl, substituted with at least one fluorine and at least one chlorine, $Y^1$ is as described herein. In an exemplary embodiment, Y is $C_1$-$C_6$ alkyl, substituted with at least one fluorine and at least one bromine, $Y^1$ is as described herein. In an exemplary embodiment, Y is $C_1$-$C_6$ alkyl, substituted with at least one chlorine and at least one bromine, $Y^1$ is as described herein. In an exemplary embodiment, Y is fluoro-substituted $C_1$-$C_6$ alkyl, and $Y^1$ is chloro. In an exemplary embodiment, Y is trifluoro-substituted $C_1$-$C_6$ alkyl, $Y^1$ is chloro. In an exemplary embodiment, Y is fluoro-substituted $C_1$-$C_6$ alkyl, and $Y^1$ is fluoro. In an exemplary embodiment, Y is trifluoro-substituted $C_1$-$C_6$ alkyl, $Y^1$ is fluoro. In an exemplary embodiment, Y is fluoro-substituted $C_1$-$C_6$ alkyl, and $Y^1$ is bromo. In an exemplary embodiment, the compound of the invention has a structure which is:

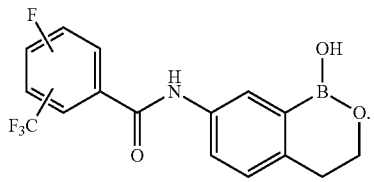

In an exemplary embodiment, the compound of the invention has a structure which is:

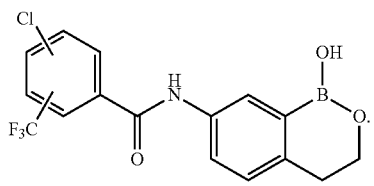

In an exemplary embodiment, the compound of the invention has a structure which is:

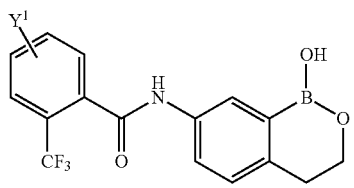

wherein $Y^1$ is as described herein.
In an exemplary embodiment, the compound of the invention has a structure which is:

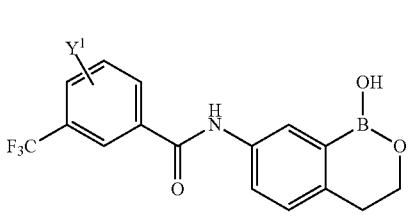

wherein $Y^1$ is as described herein.
In an exemplary embodiment, the compound of the invention has a structure which is:

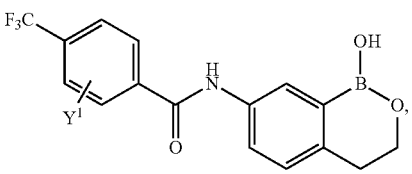

wherein $Y^1$ is as described herein.
In an exemplary embodiment, the compound of the invention has a structure which is:

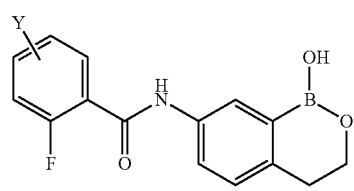

wherein Y is as described herein.
In an exemplary embodiment, the compound of the invention has a structure which is:

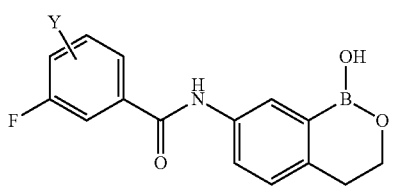

wherein Y is as described herein.
In an exemplary embodiment, the compound of the invention has a structure which is:

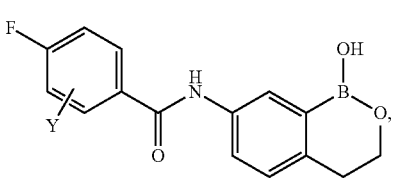

wherein Y is as described herein.
In an exemplary embodiment, the compound of the invention has a structure which is:

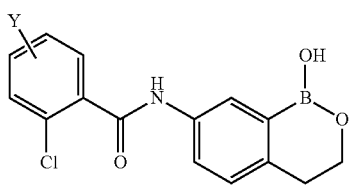

wherein Y is as described herein.
In an exemplary embodiment, the compound of the invention has a structure which is:

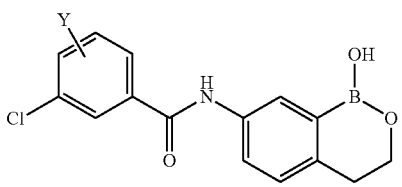

wherein Y is as described herein.
In an exemplary embodiment, the compound of the invention has a structure which is:

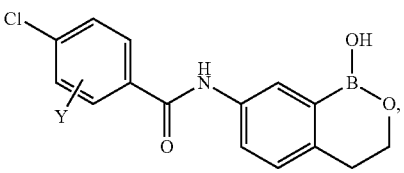

wherein Y is as described herein.
In an exemplary embodiment, the compound has a structure according to the following formula:

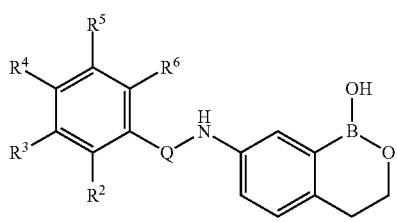

wherein $R^2$, $R^3$, $R^4$, $R^5$ and $R^6$ are according to the entries in the following table, or a salt thereof.

|  | $R^2$ | $R^3$ | $R^4$ | $R^5$ | $R^6$ |
|---|---|---|---|---|---|
| 182 | $CF_3$ | F | H | H | H |
| 183 | $CF_3$ | H | F | H | H |
| 184 | $CF_3$ | H | H | F | H |
| 185 | $CF_3$ | H | H | H | F |
| 186 | F | $CF_3$ | H | H | H |
| 187 | H | $CF_3$ | F | H | H |
| 188 | H | $CF_3$ | H | F | H |
| 189 | H | $CF_3$ | H | H | F |
| 190 | F | H | $CF_3$ | H | H |
| 191 | H | F | $CF_3$ | H | H |
| 192 | H | H | $CF_3$ | F | H |
| 193 | H | H | $CF_3$ | H | F |
| 194 | F | H | H | $CF_3$ | H |
| 195 | H | F | H | $CF_3$ | H |
| 196 | H | H | F | $CF_3$ | H |
| 197 | H | H | H | $CF_3$ | F |
| 198 | F | H | H | H | $CF_3$ |
| 199 | H | F | H | H | $CF_3$ |
| 200 | H | H | F | H | $CF_3$ |
| 201 | H | H | H | F | $CF_3$ |
| 202 | $CF_3$ | Cl | H | H | H |
| 203 | $CF_3$ | H | Cl | H | H |
| 204 | $CF_3$ | H | H | Cl | H |
| 205 | $CF_3$ | H | H | H | Cl |
| 206 | Cl | $CF_3$ | H | H | H |
| 207 | H | $CF_3$ | Cl | H | H |
| 208 | H | $CF_3$ | H | Cl | H |
| 209 | H | $CF_3$ | H | H | Cl |
| 210 | Cl | H | $CF_3$ | H | H |
| 211 | H | Cl | $CF_3$ | H | H |
| 212 | H | H | $CF_3$ | Cl | H |
| 213 | H | H | $CF_3$ | H | Cl |
| 214 | Cl | H | H | $CF_3$ | H |
| 215 | H | Cl | H | $CF_3$ | H |
| 216 | H | H | Cl | $CF_3$ | H |
| 217 | H | H | H | $CF_3$ | Cl |
| 218 | Cl | H | H | H | $CF_3$ |
| 219 | H | Cl | H | H | $CF_3$ |
| 220 | H | H | Cl | H | $CF_3$ |
| 221 | H | H | H | Cl | $CF_3$ |
| 222 | $CF_3$ | $CF_3$ | H | H | H |
| 223 | $CF_3$ | H | $CF_3$ | H | H |
| 224 | $CF_3$ | H | H | $CF_3$ | H |
| 225 | $CF_3$ | H | H | H | $CF_3$ |
| 226 | H | $CF_3$ | $CF_3$ | H | H |
| 227 | H | $CF_3$ | H | $CF_3$ | H |
| 228 | H | $CF_3$ | H | H | $CF_3$ |
| 229 | H | H | $CF_3$ | $CF_3$ | H |
| 230 | H | H | $CF_3$ | H | $CF_3$ |
| 231 | H | H | H | $CF_3$ | $CF_3$ |
| 232 | F | F | H | H | H |
| 233 | F | H | F | H | H |
| 234 | F | H | H | F | H |
| 235 | F | H | H | H | F |
| 236 | H | F | F | H | H |
| 237 | H | F | H | F | H |
| 238 | H | F | H | H | F |
| 239 | H | H | F | F | H |
| 240 | H | H | F | H | F |
| 241 | H | H | H | F | F |
| 242 | Cl | Cl | H | H | H |
| 243 | Cl | H | Cl | H | H |
| 244 | Cl | H | H | Cl | H |
| 245 | Cl | H | H | H | Cl |
| 246 | H | Cl | Cl | H | H |
| 247 | H | Cl | H | Cl | H |
| 248 | H | Cl | H | H | Cl |
| 249 | H | H | Cl | Cl | H |
| 250 | H | H | Cl | H | Cl |
| 251 | H | H | H | Cl | Cl |
| 252 | F | Cl | H | H | H |
| 253 | F | H | Cl | H | H |
| 254 | F | H | H | Cl | H |
| 255 | F | H | H | H | Cl |
| 256 | H | F | Cl | H | H |
| 257 | H | F | H | Cl | H |
| 258 | H | F | H | H | Cl |
| 259 | H | H | F | Cl | H |
| 260 | H | H | F | H | Cl |
| 261 | H | H | H | F | Cl |
| 262 | Cl | F | H | H | H |
| 263 | Cl | H | F | H | H |
| 264 | Cl | H | H | F | H |
| 265 | Cl | H | H | H | F |
| 266 | H | Cl | F | H | H |
| 267 | H | Cl | H | F | H |
| 268 | H | Cl | H | H | F |
| 269 | H | H | Cl | F | H |
| 270 | H | H | Cl | H | F |
| 271 | H | H | H | Cl | F |
| 272 | —$CH_3$ | —$CH_3$ | H | H | H |

-continued

|     | R² | R³ | R⁴ | R⁵ | R⁶ |
|---|---|---|---|---|---|
| 273 | —CH₃ | H | —CH₃ | H | H |
| 274 | —CH₃ | H | H | —CH₃ | H |
| 275 | —CH₃ | H | H | H | —CH₃ |
| 276 | H | —CH₃ | —CH₃ | H | H |
| 277 | H | —CH₃ | H | —CH₃ | H |
| 278 | H | —CH₃ | H | H | —CH₃ |
| 279 | H | H | —CH₃ | —CH₃ | H |
| 280 | H | H | —CH₃ | H | —CH₃ |
| 281 | H | H | H | —CH₃ | —CH₃ |
| 282 | —Y³ | —CH₃ | H | H | H |
| 283 | —Y³ | H | —CH₃ | H | H |
| 284 | —Y³ | H | H | —CH₃ | H |
| 285 | —Y³ | H | H | H | —CH₃ |
| 286 | H | —Y³ | —CH₃ | H | H |
| 287 | H | —Y³ | H | —CH₃ | H |
| 288 | H | —Y³ | H | H | —CH₃ |
| 289 | H | H | —Y³ | —CH₃ | H |
| 290 | H | H | —Y³ | H | —CH₃ |
| 291 | H | H | H | —Y³ | —CH₃ |
| 292 | —CH₃ | —Y³ | H | H | H |
| 293 | —CH₃ | H | —Y³ | H | H |
| 294 | —CH₃ | H | H | —Y³ | H |
| 295 | —CH₃ | H | H | H | —Y³ |
| 296 | H | —CH₃ | —Y³ | H | H |
| 297 | H | —CH₃ | H | —Y³ | H |
| 298 | H | —CH₃ | H | H | —Y³ |
| 299 | H | H | —CH₃ | —Y³ | H |
| 300 | H | H | —CH₃ | H | —Y³ |
| 301 | H | H | H | —CH₃ | —Y³ |
| 302 | —Y² | —OCH₃ | H | H | H |
| 303 | —Y² | H | —OCH₃ | H | H |
| 304 | —Y² | H | H | —OCH₃ | H |
| 305 | —Y² | H | H | H | —OCH₃ |
| 306 | H | —Y² | —OCH₃ | H | H |
| 307 | H | —Y² | H | —OCH₃ | H |
| 308 | H | —Y² | H | H | —OCH₃ |
| 309 | H | H | —Y² | —OCH₃ | H |
| 310 | H | H | —Y² | H | —OCH₃ |
| 311 | H | H | H | —Y² | —OCH₃ |
| 312 | —OCH₃ | —Y² | H | H | H |
| 313 | —OCH₃ | H | —Y² | H | H |
| 314 | —OCH₃ | H | H | —Y² | H |
| 315 | —OCH₃ | H | H | H | —Y² |
| 316 | H | —OCH₃ | —Y² | H | H |
| 317 | H | —OCH₃ | H | —Y² | H |
| 318 | H | —OCH₃ | H | H | —Y² |
| 319 | H | H | —OCH₃ | —Y² | H |
| 320 | H | H | —OCH₃ | H | —Y² |
| 321 | H | H | H | —OCH₃ | —Y² |
| 322 | —OCH₃ | —OCH₃ | H | H | H |
| 323 | —OCH₃ | H | —OCH₃ | H | H |
| 324 | —OCH₃ | H | H | —OCH₃ | H |
| 325 | —OCH₃ | H | H | H | —OCH₃ |
| 326 | H | —OCH₃ | —OCH₃ | H | H |
| 327 | H | —OCH₃ | H | —OCH₃ | H |
| 328 | H | —OCH₃ | H | H | —OCH₃ |
| 329 | H | H | —OCH₃ | —OCH₃ | H |
| 330 | H | H | —OCH₃ | H | —OCH₃ |
| 331 | H | H | H | —OCH₃ | —OCH₃ |
| 332 | —CH₃ | —OCH₃ | H | H | H |
| 333 | —CH₃ | H | —OCH₃ | H | H |
| 334 | —CH₃ | H | H | —OCH₃ | H |
| 335 | —CH₃ | H | H | H | —OCH₃ |
| 336 | H | —CH₃ | —OCH₃ | H | H |
| 337 | H | —CH₃ | H | —OCH₃ | H |
| 338 | H | —CH₃ | H | H | —OCH₃ |
| 339 | H | H | —CH₃ | —OCH₃ | H |
| 340 | H | H | —CH₃ | H | —OCH₃ |
| 341 | H | H | H | —CH₃ | —OCH₃ |
| 342 | —OCH₃ | —CH₃ | H | H | H |
| 343 | —OCH₃ | H | —CH₃ | H | H |
| 344 | —OCH₃ | H | H | —CH₃ | H |
| 345 | —OCH₃ | H | H | H | —CH₃ |
| 346 | H | —OCH₃ | —CH₃ | H | H |
| 347 | H | —OCH₃ | H | —CH₃ | H |
| 348 | H | —OCH₃ | H | H | —CH₃ |
| 349 | H | H | —OCH₃ | —CH₃ | H |
| 350 | H | H | —OCH₃ | H | —CH₃ |
| 351 | H | H | H | —OCH₃ | —CH₃ |
| 352 | —Y² | —Y² | H | H | H |
| 353 | —Y² | H | —Y² | H | H |
| 354 | —Y² | H | H | —Y² | H |
| 355 | —Y² | H | H | H | —Y² |
| 356 | H | —Y² | —Y² | H | H |
| 357 | H | —Y² | H | —Y² | H |
| 358 | H | —Y² | H | H | —Y² |
| 359 | H | H | —Y² | H | —Y² |
| 360 | —Y³ | —Y³ | H | H | H |
| 361 | —Y³ | H | —Y³ | H | H |
| 362 | —Y³ | H | H | —Y³ | H |
| 363 | —Y³ | H | H | H | —Y³ |
| 364 | H | —Y³ | —Y³ | H | H |
| 365 | H | —Y³ | H | —Y³ | H |
| 366 | H | —Y³ | H | H | —Y³ |
| 367 | H | H | —Y³ | H | —Y³ |
| 368 | —Y² | —Y³ | H | H | H |
| 369 | —Y² | H | —Y³ | H | H |
| 370 | —Y² | H | H | —Y³ | H |
| 371 | —Y² | H | H | H | —Y³ |
| 372 | H | —Y² | —Y³ | H | H |
| 373 | H | —Y² | H | —Y³ | H |
| 374 | H | —Y² | H | H | —Y³ |
| 375 | H | H | —Y² | H | —Y³ |
| 376 | —Y³ | —Y² | H | H | H |
| 377 | —Y³ | H | —Y² | H | H |
| 378 | —Y³ | H | H | —Y² | H |
| 379 | —Y³ | H | H | H | —Y² |
| 380 | H | —Y³ | —Y² | H | H |
| 381 | H | —Y³ | H | —Y² | H |
| 382 | H | —Y³ | H | H | —Y² |
| 383 | H | H | —Y³ | H | —Y² |

For any of the entries in the above table, Q is SO₂. For any of the entries in the above table, Q is C=O.

In an exemplary embodiment, the compound of the invention has a structure according to the following formula:

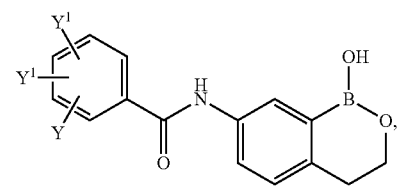

wherein each Y¹ is independently selected halogen, Y is halo-substituted $C_1$-$C_6$ alkyl. In an exemplary embodiment, Q is SO₂. In an exemplary embodiment, Q is C=O. In an exemplary embodiment, Y is fluoro-substituted $C_1$-$C_6$ alkyl, and each Y¹ is as described herein. In an exemplary embodiment, Y is trifluoro-substituted $C_1$-$C_6$ alkyl, and each Y¹ is as described herein. In an exemplary embodiment, Y is as described herein, and each Y¹ is as described herein. In an exemplary embodiment, Y is fluoro-substituted $C_1$-$C_6$ alkyl, and each Y¹ is chloro. In an exemplary embodiment, Y is fluoro-substituted $C_1$-$C_6$ alkyl, and each Y¹ is fluoro. In an exemplary embodiment, Y is fluoro-substituted $C_1$-$C_6$ alkyl, a Y¹ is fluoro, and another Y¹ is chloro. In an exemplary embodiment, Y is trifluoro-substituted $C_1$-$C_6$ alkyl, and each Y¹ is chloro. In an exemplary embodiment, Y is trifluoro-substituted $C_1$-$C_6$ alkyl, and each Y¹ is fluoro. In an exemplary embodiment, Y is trifluoro-substituted $C_1$-$C_6$ alkyl, a Y¹ is fluoro, and another Y¹ is chloro. In an exemplary embodiment, the compound of the invention has a structure which is selected from the group consisting of

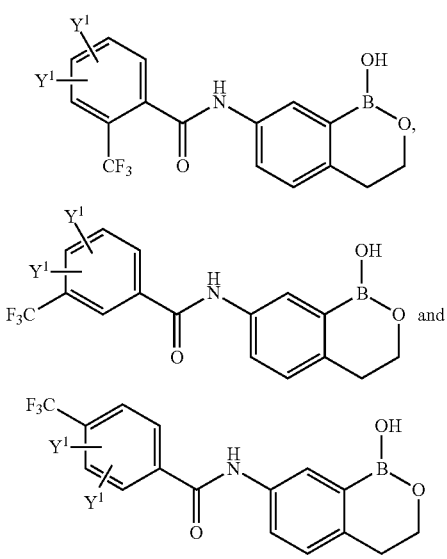

wherein each Y¹ is as described herein.

In an exemplary embodiment, the compound of the invention has a structure which is selected from the group consisting of

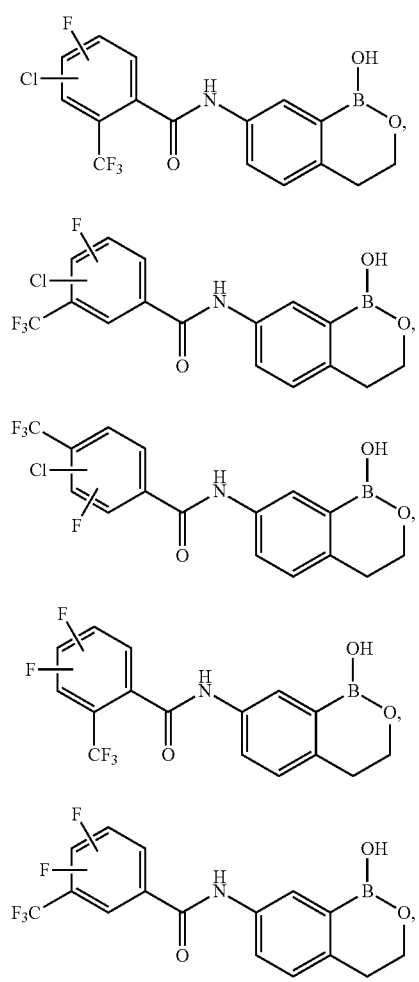

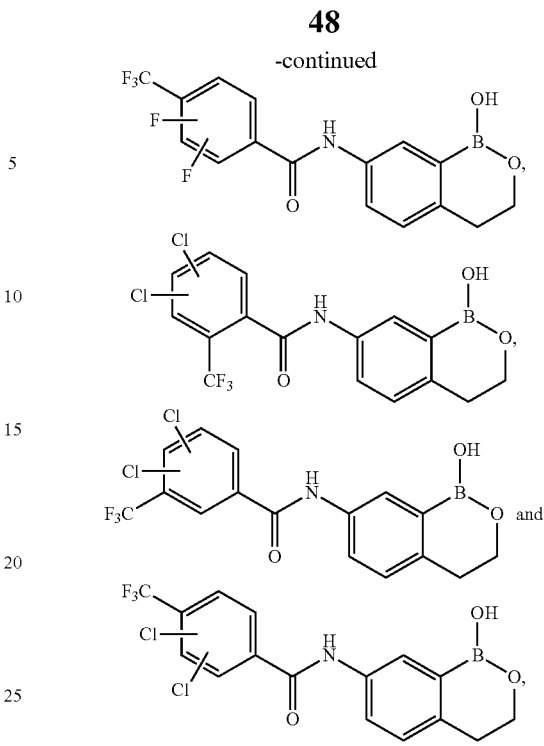

or a salt thereof.

In an exemplary embodiment, the compound of the invention has a structure according to the following formula:

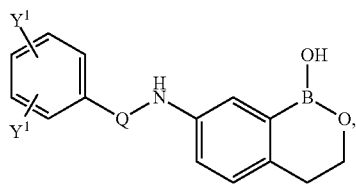

wherein Q is as described herein, and each Y¹ is a halogen. In an exemplary embodiment, Q is $SO_2$. In an exemplary embodiment, Q is C=O. In an exemplary embodiment, each Y¹ is as described herein. In an exemplary embodiment, each Y¹ is fluoro. In an exemplary embodiment, each Y¹ is chloro. In an exemplary embodiment, one Y¹ is fluoro and another is Y¹ is chloro.

In an exemplary embodiment, the compound of the invention has a structure according to the following formula:

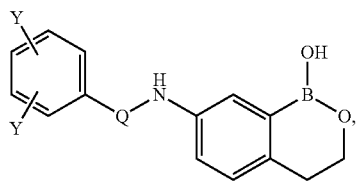

wherein Q is as described herein, and each Y is an independently selected halo-substituted $C_1$-$C_6$ alkyl. In an exemplary embodiment, Q is $SO_2$. In an exemplary embodiment, Q is C=O. In an exemplary embodiment, each Y is as described herein. In an exemplary embodiment, one Y is fluoro-substituted $C_1$-$C_6$ alkyl, and the other Y is as described herein. In an exemplary embodiment, one Y is trifluoro-substituted $C_1$-$C_6$ alkyl and the other Y is as described herein. In an exemplary embodiment, each Y is fluoro-substituted $C_1$-$C_6$ alkyl. In an exemplary embodiment, each Y is trifluoro-substituted $C_1$-$C_6$ alkyl.

In an exemplary embodiment, the compound of the invention has a structure according to the following formula:

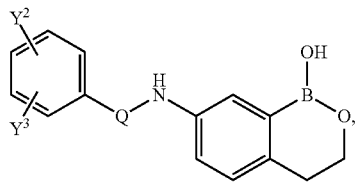

wherein $Y^2$ is unsubstituted alkyl and $Y^3$ is unsubstituted alkoxy, and Q is as described herein. In an exemplary embodiment, Q is $SO_2$. In an exemplary embodiment, Q is C=O. In an exemplary embodiment, $Y^2$ is as described herein, and $Y^3$ is as described herein. In an exemplary embodiment, $Y^2$ is unsubstituted $C_1$-$C_6$ alkyl, and $Y^3$ is unsubstituted $C_1$-$C_6$ alkoxy. In an exemplary embodiment, $Y^2$ is methyl, $Y^3$ is as described herein. In an exemplary embodiment, $Y^2$ is as described herein, $Y^3$ is methoxy.

In an exemplary embodiment, the compound of the invention has a structure according to the following formula:

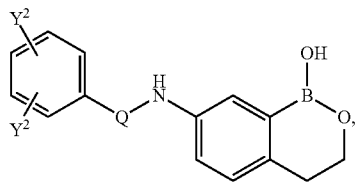

wherein each $Y^2$ is unsubstituted alkyl and Q is as described herein. In an exemplary embodiment, Q is $SO_2$. In an exemplary embodiment, Q is C=O. In an exemplary embodiment, each $Y^2$ is as described herein. In an exemplary embodiment, $Y^2$ is unsubstituted $C_1$-$C_6$ alkyl. In an exemplary embodiment, one $Y^2$ is methyl, and the other $Y^2$ is an unsubstituted alkyl aside from methyl. In an exemplary embodiment, both $Y^2$ are methyl.

In an exemplary embodiment, the compound of the invention has a structure according to the following formula:

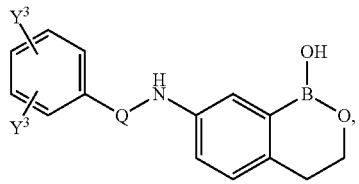

wherein each $Y^3$ is independently selected unsubstituted alkoxy and Q is as described herein. In an exemplary embodiment, Q is $SO_2$. In an exemplary embodiment, Q is C=O. In an exemplary embodiment, each $Y^3$ is as described herein. In an exemplary embodiment, $Y^3$ is unsubstituted $C_1$-$C_6$ alkoxy, and $Y^3$ is unsubstituted $C_1$-$C_6$ alkoxy. In an exemplary embodiment, a $Y^3$ is methoxy, and another $Y^3$ is as described herein.

In an exemplary embodiment, the compound has a structure according to the following formula:

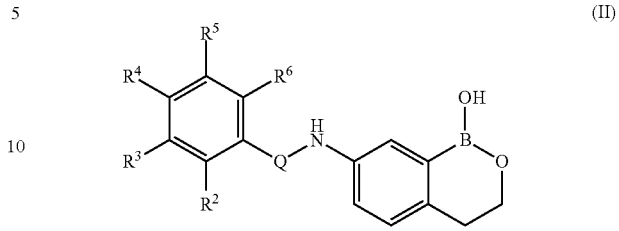

wherein $R^2$, $R^3$, $R^4$, $R^5$ and $R^6$ are according to the entries in the following table, or a salt thereof.

| | $R^2$ | $R^3$ | $R^4$ | $R^5$ | $R^6$ |
|---|---|---|---|---|---|
| 384 | —OCH$_3$ | —OCH$_3$ | —OCH$_3$ | H | H |
| 385 | —OCH$_3$ | —OCH$_3$ | H | —OCH$_3$ | H |
| 386 | —OCH$_3$ | —OCH$_3$ | H | H | —OCH$_3$ |
| 387 | —OCH$_3$ | H | —OCH$_3$ | H | —OCH$_3$ |
| 388 | —OCH$_3$ | H | —OCH$_3$ | —OCH$_3$ | H |
| 389 | H | —OCH$_3$ | —OCH$_3$ | —OCH$_3$ | H |
| 390 | H | —OCH$_3$ | H | —OCH$_3$ | —OCH$_3$ |
| 391 | H | H | —OCH$_3$ | —OCH$_3$ | —OCH$_3$ |
| 392 | —CF$_3$ | —Y$^1$ | —Y$^1$ | H | H |
| 393 | —CF$_3$ | —Y$^1$ | H | —Y$^1$ | H |
| 394 | —CF$_3$ | —Y$^1$ | H | H | —Y$^1$ |
| 395 | —CF$_3$ | H | —Y$^1$ | H | —Y$^1$ |
| 396 | —CF$_3$ | H | —Y$^1$ | —Y$^1$ | H |
| 397 | H | —CF$_3$ | —Y$^1$ | —Y$^1$ | H |
| 398 | H | —CF$_3$ | H | —Y$^1$ | —Y$^1$ |
| 399 | H | H | —CF$_3$ | —Y$^1$ | —Y$^1$ |
| 400 | —Y$^1$ | —CF$_3$ | —Y$^1$ | H | H |
| 401 | —Y$^1$ | —CF$_3$ | H | —Y$^1$ | H |
| 402 | —Y$^1$ | —CF$_3$ | H | H | —Y$^1$ |
| 403 | —Y$^1$ | H | —CF$_3$ | H | —Y$^1$ |
| 404 | —Y$^1$ | H | —CF$_3$ | —Y$^1$ | H |
| 405 | H | —Y$^1$ | —CF$_3$ | —Y$^1$ | H |
| 406 | H | —Y$^1$ | H | —CF$_3$ | —Y$^1$ |
| 407 | H | H | —Y$^1$ | —CF$_3$ | —Y$^1$ |
| 408 | —Y$^1$ | —Y$^1$ | —CF$_3$ | H | H |
| 409 | —Y$^1$ | —Y$^1$ | H | —CF$_3$ | H |
| 410 | —Y$^1$ | —Y$^1$ | H | H | —CF$_3$ |
| 411 | —Y$^1$ | H | —Y$^1$ | H | —CF$_3$ |
| 412 | —Y$^1$ | H | —Y$^1$ | —CF$_3$ | H |
| 413 | H | —Y$^1$ | —Y$^1$ | —CF$_3$ | H |
| 414 | H | —Y$^1$ | H | —Y$^1$ | —CF$_3$ |
| 415 | H | H | —Y$^1$ | —Y$^1$ | —CF$_3$ |
| 416 | —Y$^1$ | —Y$^1$ | —CF$_3$ | H | H |
| 417 | —Y$^1$ | —Y$^1$ | H | —CF$_3$ | H |
| 418 | —Y$^1$ | —Y$^1$ | H | H | —CF$_3$ |
| 419 | —Y$^1$ | H | —Y$^1$ | H | —CF$_3$ |
| 420 | —Y$^1$ | H | —Y$^1$ | —CF$_3$ | H |
| 421 | H | —Y$^1$ | —Y$^1$ | —CF$_3$ | H |
| 422 | H | —Y$^1$ | H | —Y$^1$ | —CF$_3$ |
| 423 | H | H | —Y$^1$ | —Y$^1$ | —CF$_3$ |

For any of the entries in the above table, Q is $SO_2$. For any of the entries in the above table, Q is C=O.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof.

In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III.b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{conc.\ of\ z - conc.\ of\ y}{conc.\ of\ z + conc.\ of\ y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analogously to enantiomeric excess. Thus:

$$de_w = \left(\frac{conc.\ of\ major\ diastereomer - conc.\ of\ min\ or\ diastereomer(s)}{conc.\ of\ major\ diastereomer + conc.\ of\ min\ or\ diastereomer(s)}\right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diasteromer of the first compound of the invention. In another embodiment, the invention provides a composition including a first compound of the invention, wherein the first compound of the invention has two stereocenters, and only one diasteromer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the (R) enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

In an exemplary embodiment, the invention provides a composition comprising a) first compound described herein; and b) the enantiomer of the first compound, wherein the first compound described herein is present in an enantiomeric excess of at least 80%. In an exemplary embodiment, the enantiomeric excess is at least 92%.

III.c) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is berenil. In an exemplary embodiment, the additional therapeutic agent is diminazene. In an exemplary embodiment, the additional therapeutic agent is an antiprotozoa. In an exemplary embodiment, the additional therapeutic agent is selected from the group consisting of benznidazole, buparvaquone, carbarsone, clioquinol, disulfuram, eflornithine, emetine, etofamide, furazolidone, meglumine antimoniate, melarsoprol, metronidazole, miltefosine, nifurtimox, nimorazole, nitazoxanide, ornidazole, paromomycin sulfate, pentamidine, pyrimethamine, secnidazole and timidazole. In an exemplary embodiment, the additional therapeutic agent is pentamidine. In an exemplary embodiment, the additional therapeutic agent is suramin. In an exemplary embodiment, the additional therapeutic agent is eflornithine. In an exemplary embodiment, the additional therapeutic agent is melarsoprol. In an exemplary embodiment, the additional therapeutic agent is nifurtimox. In an exemplary embodiment, the additional therapeutic agent contains a 5-nitrofuran moiety. In an exemplary embodiment, the additional therapeutic agent contains a 5-nitroimidazolyl moiety. In an exemplary embodiment, the additional therapeutic agent is fexinidazole. In an exemplary embodiment, the additional therapeutic agent is an antiparasitic. In an exemplary embodiment, the additional therapeutic agent is selected from the group consisting of amitraz, avermectin, carbadox, diethylcarbamazine, dimetridazole, diminazene, ivermectin, macrofilaricide, malathion, mitaban, organophosphate, oxamniquine, permethrin, praziquantel, pyrantel pamoate, selamectin, sodium stibogluconate and thiabendazole. In an exemplary embodiment, the additional therapeutic agent is selected from the group consisting of antimony, meglumine antimoniate, sodium stibogluconate, amphotericin, miltefosine and paromomycin.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRONT™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

III.d) Preparation of Boron-Containing Compounds

Compounds of use in the invention can be prepared using commercially available starting materials, known intermediates, or by using the synthetic methods described herein, or published in references described and incorporated by reference herein, such as U.S. patent application Ser. No. 12/142,692 and U.S. Pat. Pubs. US20060234981, US20070155699 and US20070293457.

In one embodiment, the compound of the invention can be synthesized according to the following scheme:

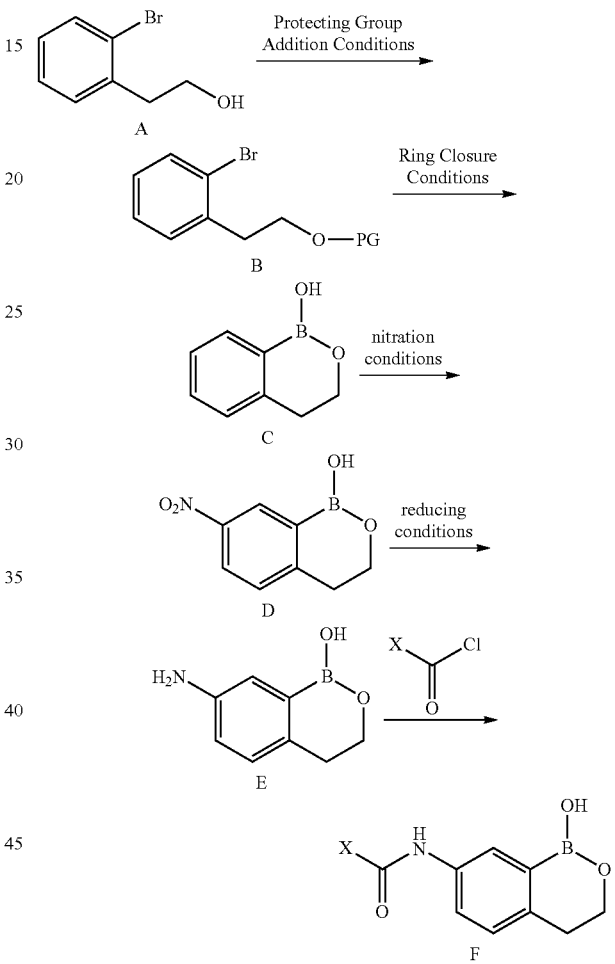

wherein A is commercially available from, for example, Sigma-Aldrich. A can be converted to B by subjecting it to protection conditions, such as those involving dihydropyran and an acid catalyst. B can be converted to C by in situ metalation using, for example, n-butyllithium, followed by boronation conditions such as with tri-isopropyl borate and hydrolysis conditions such as those involving aqueous hydrochloric acid. C can be converted to D through subjecting it to nitration conditions, such as those involving fuming nitric acid. D can be converted to E by subjecting it to reducing conditions, such as those involving catalytic hydrogenation. E can be converted to F through subjecting it to acid chloride addition conditions.

In one embodiment, the compound of the invention can be synthesized according to the following scheme:

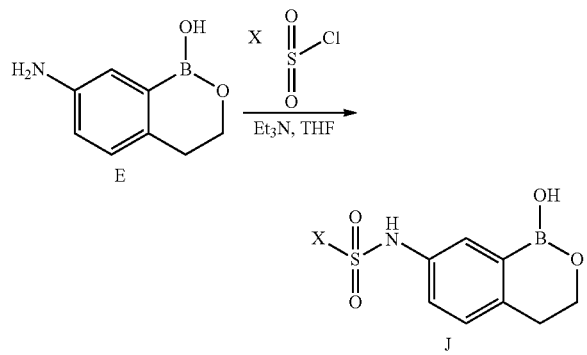

wherein E can be converted to J through subjecting it to sulfonyl chloride addition conditions.

Compounds described herein can be converted into hydrates and solvates by methods similar to those described herein.

IV. Methods of Inhibiting Microorganism Growth or Killing Microorganisms

The compounds of the invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In another exemplary embodiment, the protozoa is a *Trypanosoma brucei*. In another exemplary embodiment, the protozoa is *Trypanosoma brucei brucei*. In another exemplary embodiment, the protozoa is *Trypanosoma brucei rhodesiense*. In another exemplary embodiment, the protozoa is *Trypanosoma brucei gambiense*. In another exemplary embodiment, the protozoa is *Trypanosoma cruzi*. In another exemplary embodiment, the protozoa is a member of the genus *Leishmania*. In another exemplary embodiment, the protozoa is a member of *Leishmania Viannia*. In an exemplary embodiment, the protozoa is selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the protozoa is *L. donovani*. In an exemplary embodiment, the protozoa is *L. infantum*. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Methods of Treating and/or Preventing Disease

The compounds of the invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In an exemplary embodiment, the disease is associated with a *Trypanosoma brucei*. In an exemplary embodiment, the disease is associated with a member selected from the group consisting of *Trypanosoma brucei brucei, Trypanosoma brucei rhodesiense* and *Trypanosoma brucei gambiense*. In an exemplary embodiment, the disease is associated with *Trypanosoma brucei rhodesiense*. In an exemplary embodiment, the disease is associated with *Trypanosoma brucei gambiense*. In an exemplary embodiment, the disease is associated with *Trypanosoma cruzi*. In an exemplary embodiment, the disease is a trypanosomiasis. In an exemplary embodiment, the disease is a human trypanosomiasis. In an exemplary embodiment, the disease is an animal trypanosomiasis. In an exemplary embodiment, the disease is selected from the group consisting of nagana, surra, mal de caderas, murrina de caderas, dourine, cachexial fevers, Gambian horse sickness, baleri, kaodzera, tahaga, galziekte or galzietzke and peste-boba. In an exemplary embodiment, the disease is selected from the group consisting of Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is sleeping sickness (or African sleeping sickness). In an exemplary embodiment, the disease is acute phase sleeping sickness. In an exemplary embodiment, the disease is chronic phase sleeping sickness. In an exemplary embodiment, the disease is an acute phase of a trypanosomiasis. In an exemplary embodiment, the disease is a chronic phase of a trypanosomiasis. In an exemplary embodiment, the disease is the non-CNS form of a trypanosomiasis. In an exemplary embodiment, the disease is the CNS form of a trypanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania Vianmia*. In an exemplary embodiment, the disease is associated with a member selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the disease is associated with *L. donovani*. In an exemplary embodiment, the disease is associated with *L. infantum*. In an exemplary embodiment, the disease is leishmaniasis. In an exemplary embodiment, the disease is visceral leishmaniasis. In an exemplary embodiment, the disease is cutaneous leishmaniasis. In an exemplary embodiment, the disease is diffuse cutaneous leishmaniasis and/or mucocutaneous leishmaniasis. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the animal is a human.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure according to the following formula:

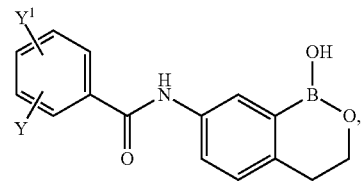

wherein $Y^1$ is a halogen, Y is halosubstituted alkyl, or a salt thereof.

In an exemplary embodiment, according to the above paragraph, wherein $Y^1$ is fluoro.

In an exemplary embodiment, according to any of the above paragraphs, wherein Y is trifluoromethyl.

In an exemplary embodiment, according to any of the above paragraphs, the compound has a structure according to the following formula:

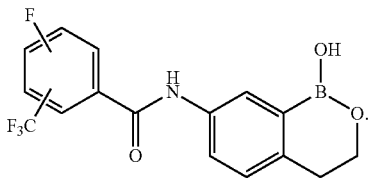

In an exemplary embodiment, according to any of the above paragraphs, the compound has a structure according to the following formula:

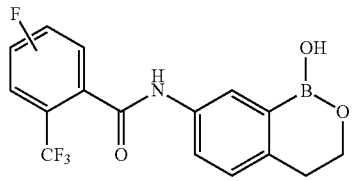

In an exemplary embodiment, according to any of the above paragraphs, the compound has a structure according to the following formula:

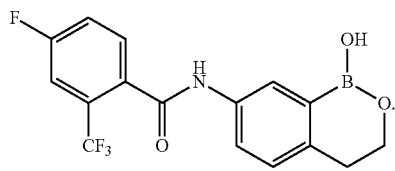 [SMILES: O=C(Nc1ccc2c(c1)B(O)OCC2)c1ccc(F)cc1C(F)(F)F]

In an exemplary embodiment, the invention provides a combination comprising the compound according to any of the above paragraphs, together with at least one other therapeutically active agent.

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with a compound of the invention, thereby killing and/or preventing the growth of the protozoa.

In an exemplary embodiment, according to any of the above paragraphs, wherein an effective amount of the compound of the invention contacts the protozoa.

In an exemplary embodiment, according to any of the above paragraphs, the compound has a structure described herein.

In an exemplary embodiment, according to any of the above paragraphs, the protozoa is a member of the trypanosome genus.

In an exemplary embodiment, according to any of the above paragraphs, the protozoa is a member of the *leishmania* genus.

In an exemplary embodiment, according to any of the above paragraphs, the protozoa is *Trypanosoma brucei*.

In an exemplary embodiment, according to any of the above paragraphs, the *Trypanosoma brucei* is selected from the group consisting of *Trypanosoma brucei brucei*, *Trypanosoma brucei gambiense* and *Trypanosoma brucei rhodesiense*.

In an exemplary embodiment, according to any of the above paragraphs, the protozoa is selected from the group consisting of *Leishmania donovani, Leishmania infantum, Leishmania chagasi, Leishmania mexicana, Leishmania amazonensis, Leishmania venezuelensis, Leishmania tropica, Leishmania major* and *Leishmania aethiopica*.

In an exemplary embodiment, according to any of the above paragraphs, the protozoa is *Leishmania donovani*.

In an exemplary embodiment, the invention provides a method of treating and/or preventing a disease in an animal, comprising: administering to the animal a therapeutically effective amount of the compound of the invention, thereby treating and/or preventing the disease.

In an exemplary embodiment, according to any of the above paragraphs, the compound has a structure described herein.

In an exemplary embodiment, according to any of the above paragraphs, the disease is African sleeping sickness.

In an exemplary embodiment, according to any of the above paragraphs, the disease is leishmaniasis.

In an exemplary embodiment, according to any of the above paragraphs, the leishmaniasis is selected from the group consisting of visceral leishmaniasis, cutaneous leishmaniasis, diffuse cutaneous leishmaniasis and mucocutaneous leishmaniasis.

In an exemplary embodiment, according to any of the above paragraphs, the leishmaniasis is visceral leishmaniasis.

In an exemplary embodiment, according to any of the above paragraphs, the leishmaniasis is cutaneous leishmaniasis.

In an exemplary embodiment, according to any of the above paragraphs, the animal is a human.

In an exemplary embodiment, according to any of the above paragraphs, the invention is a use of a compound of the invention or a combination of the invention in the manufacture of a medicament for the treatment and/or prophylaxis of protozoal infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with fits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 $C_{18}$ column, Dyonex Chromeleon operating system coupled with a Varian Prostar 320 UV-vis detector (254 nm) and a Sedex55 ELS detector. Conditions: Solvent A: $H_2O$/1% acetonitrile/0.1% $HCO_2H$; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

Example 1

M1. 4-Fluoro-N-(1-hydroxy-3,4-dihydro-1H-benzo[c][1,2]oxaborinin-7-yl)-2-trifluoromethyl-benzamide

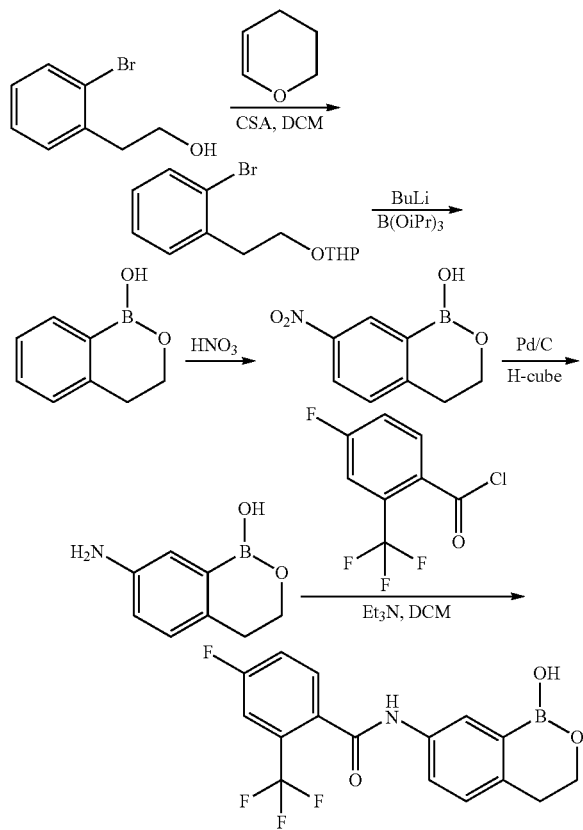

To a solution of 2-(2-bromo-phenyl)-ethanol (5.0 g, 24.9 mmol, 1.0 eq) in DCM (100 mL) was added 3,4-dihydro-2H-pyran (3.4 mL, 37.3 mmol, 1.5 eq.), followed by camphorsulfonic acid (2100 mg). The mixture was stirred at room temperature for 2 h. After adding K$_2$CO$_3$ (300 mg), the mixture was filtered to remove the precipitate, the filtrate was washed with H$_2$O (100 mL), brine (100 mL). The organic phase was dried over MgSO$_4$, filtered and the filtrate was concentrated under reduced pressure. The oily residue was applied to silica chromatography eluting with EtOAc/Heptanes (0:100 to 50:50) to give 2-[2-(2-bromo-phenyl)-ethoxy]-tetrahydro-pyran as a colorless oil. $^1$H NMR (chloroform-d) δ: 7.48-7.54 (m, 1H), 7.25-7.30 (m, 1H), 7.17-7.23 (m, 1H), 7.01-7.09 (m, 1H), 4.56-4.61 (m, 1H), 3.88-3.97 (m, 1H), 3.58-3.67 (m, 1H), 3.04 (t, J=7.2 Hz, 2H), 1.62-1.67 (m, 1H), 1.41-1.60 (m, 5H), 0.85-0.90 (m, 1H). Amount obtained: 6.9 g, 97.1% yield.

To a solution of 2-[2-(2-bromo-phenyl)-ethoxy]-tetrahydro-pyran (1.0 g, 3.5 mmol, 1.0 eq.) in THF (20 mL) at −78° C. was slowly added BuLi (2.4 mL, 2.5 M solution in THF, 3.8 mmol, 1.1 eq.) under nitrogen atmosphere. Triisopropyl borate (1.2 mL, 5.25 mmol, 1.5 eq.) was then added and the mixture was allowed to warm to room temperature gradually and stirred overnight. After carefully adding HCl (10 mL, 6N), the yellowish solution was stirred at room temperature for another 1 h and then poured into a mixture of EtOAc (30 mL) and H$_2$O (20 mL). The layers were separated and the aqueous phase was extracted with EtOAc (3×30 mL). Combined organic extracts was washed with H$_2$O (50 mL), brine (50 mL), dried over MgSO$_4$, filtered and the filtrate was concentrated under reduced pressure. The oily residue was applied to silica chromatography eluting with EtOAc/Heptanes (0:100 to 100:0) to give 3,4-dihydro-benzo[c][1,2]oxaborinin-1-ol as a light yellow solid. $^1$H NMR (acetone) δ: 7.73 (d, J=7.2 Hz, 1H), 7.33-7.39 (m, 1H), 7.15-7.26 (m, 3H), 4.10 (t, J=6.0 Hz, 2H), 2.88 (t, J=6.0 Hz, 2H). Amount obtained 497 mg, 95.9% yield.

To 4.0 mL fuming HNO$_3$ at −45° C. was added 3,4-dihydro-benzo[c][1,2]oxaborinin-1-ol (497 mg, 3.4 mmol) in small portions while maintaining the reaction temperature between −40 to −45° C. Once the addition was complete the resulting solution was allowed to stir at −45° C. for an additional 10 min before poured into crushed ice (20 g). The ice mixture was allowed to warm up to room temperature gradually and the precipitate was collected by filtration and washed with H$_2$O to give 7-nitro-3,4-dihydro-benzo[c][1,2]oxaborinin-1-ol as a white powder. $^1$H NMR (acetone) δ: 8.51 (d, J=2.5 Hz, 1H), 8.24 (dd, J=8.3, 2.6 Hz, 1H), 7.75 (s, 1H), 7.50 (d, J=8.4 Hz, 1H), 4.19 (t, J=6.0 Hz, 2H), 3.07 (t, J=6.0 Hz, 2H). Amount obtained: 286 mg, 44% yield.

A solution of 7-nitro-3,4-dihydro-benzo[c][1,2]oxaborinin-1-ol (100 mg, 0.52 mmol) in THF (10 mL) was passed through H-cube equipped with a 10% Pd/C cartridge. The collected light yellow solution was immediately treated with Et$_3$N (144 µL, 2.0 mmol, 2.0 eq.), followed by 4-fluoro-2-trifluoromethyl-benzoyl chloride (94 µL, 0.62 mmol, 1.2 eq.). The resulting mixture was stirred at room temperature overnight. The reaction solution was diluted with EtOAc (20 mL), washed with 1N HCl (10 mL), H$_2$O (10 mL), brine (10 mL) and then dried over Na$_2$SO$_4$, filtered and the filtrate was concentrated under reduced pressure and the crude material was applied to silica chromatography eluting with MeOH/DCM (0:100 to 10:90) to give the title compound as a white solid. LCMS (M/Z): 354 (M+H); $^1$H NMR (DMSO-d$_6$) δ: 10.43 (s, 1H), 8.40 (s, 1H), 7.89 (d, J=2.3 Hz, 1H), 7.75 (dt, J=5.9, 2.9 Hz, 2H), 7.58-7.67 (m, 2H), 7.15 (d, J=8.2 Hz, 1H), 4.03 (t, J=5.9 Hz, 2H), 2.80 (t, J=5.8 Hz, 2H).

M2. 2-Fluoro-N-(1-hydroxy-3,4-dihydro-1H-benzo[c][1,2]oxaborinin-7-yl)-benzamide

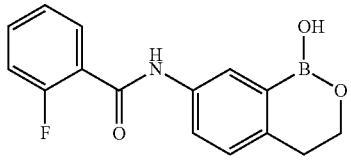

M2 was prepared using a procedure similar to that of M1 with 2-fluorobenzoyl chloride replacing 4-fluoro-2-trifluoromethyl-benzoyl chloride. Data for M2: LCMS (M/Z): 286 (M+H); $^1$H NMR (DMSO-d$_6$) δ: 10.27 (s, 1H), 8.39 (s, 1H), 7.93 (d, J=2.1 Hz, 1H), 7.69 (dd, J=8.2, 2.2 Hz, 1H), 7.62 (td, J=7.5, 1.7 Hz, 1H), 7.50-7.57 (m, 1H), 7.26-7.33 (m, 2H), 7.15 (d, J=8.2 Hz, 1H), 4.03 (t, J=5.9 Hz, 2H), 2.80 (t, J=5.8 Hz, 2H).

M3. 3-Fluoro-N-(1-hydroxy-3,4-dihydro-1H-benzo[c][1,2]oxaborinin-7-yl)-benzamide

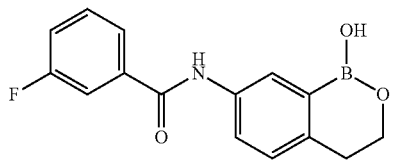 [SMILES: O=C(Nc1ccc2c(c1)B(O)OCC2)c1cccc(F)c1]

M3 was prepared using a procedure similar to that of M1 with 3-fluorobenzoyl chloride replacing 4-fluoro-2-trifluoromethyl-benzoyl chloride. Data for M3: LCMS (M/Z): 286 (M+H); $^1$H NMR (DMSO-d$_6$) δ: 10.21 (s, 1H), 8.38 (s, 1H), 7.95 (d, J=2.3 Hz, 1H), 7.77-7.81 (m, 1H), 7.71-7.77 (m, 2H), 7.54 (td, J=8.0, 6.0 Hz, 1H), 7.39 (td, J=8.5, 2.6 Hz, 1H), 7.16 (d, J=8.2 Hz, 1H), 4.03 (t, J=5.9 Hz, 2H), 2.80 (t, J=5.9 Hz, 2H).

M4. 4-Fluoro-N-(1-hydroxy-3,4-dihydro-1H-benzo[c][1,2]oxaborinin-7-yl)-benzamide

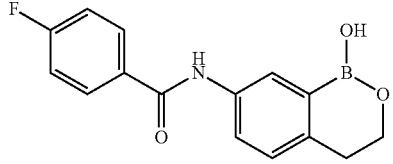 [SMILES: O=C(Nc1ccc2c(c1)B(O)OCC2)c1ccc(F)cc1]

M4 was prepared using a procedure similar to that of M1 with 4-fluorobenzoyl chloride replacing 4-fluoro-2-trifluoromethyl-benzoyl chloride. Data for M4:: LCMS (M/Z): 286 (M+H); $^1$H NMR (DMSO-d$_6$) δ: 10.16 (s, 1H), 8.37 (s, 1H), 7.98-8.03 (m, 2H), 7.94 (d, J=2.2 Hz, 1H), 7.74 (dd, J=8.2, 2.3 Hz, 1H), 7.31 (t, J=8.9 Hz, 2H), 7.15 (d, J=8.2 Hz, 1H), 4.03 (t, J=5.9 Hz, 2H), 2.80 (t, J=5.9 Hz, 2H).

M5. 2-Chloro-N-(1-hydroxy-3,4-dihydro-1H-benzo[c][1,2]oxaborinin-7-yl)-benzamide

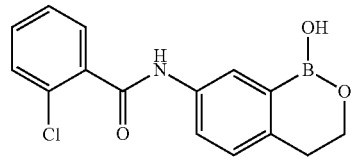

M5 was prepared using a procedure similar to that of M1 with 2-chlorobenzoyl chloride replacing 4-fluoro-2-trifluoromethyl-benzoyl chloride. Data for M5: LCMS (M/Z): 302 (M+H); $^1$H NMR (DMSO-d$_6$) δ: 10.36 (s, 1H), 8.39 (s, 1H), 7.94 (d, J=2.2 Hz, 1H), 7.66 (dd, J=8.2, 2.3 Hz, 1H), 7.50-7.53 (m, 2H), 7.39-7.49 (m, 2H), 7.15 (d, J=8.2 Hz, 1H), 4.03 (t, J=5.9 Hz, 2H), 2.80 (t, J=5.8 Hz, 2H).

M6. 3-Chloro-N-(1-hydroxy-3,4-dihydro-1H-benzo[c][1,2]oxaborinin-7-yl)-benzamide

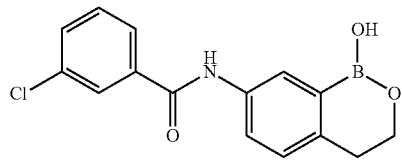 [SMILES: O=C(Nc1ccc2c(c1)B(O)OCC2)c1cccc(Cl)c1]

M6 was prepared using a procedure similar to that of M1 with 3-chlorobenzoyl chloride replacing 4-fluoro-2-trifluoromethyl-benzoyl chloride. Data for M6: LCMS (M/Z): 302 (M+H); $^1$H NMR (DMSO-d$_6$) δ: 10.25 (s, 1H), 8.39 (s, 1H), 7.99 (t, J=1.8 Hz, 1H), 7.95 (d, J=2.2 Hz, 1H), 7.89 (ddd, J=8.0, 1.3, 1.1 Hz, 1H), 7.76 (dd, J=8.2, 2.3 Hz, 1H), 7.62 (ddd, J=8.0, 2.1, 1.0 Hz, 1H), 7.53 (t, J=7.9 Hz, 1H), 7.16 (d, J=8.2 Hz, 1H), 4.04 (t, J=5.9 Hz, 2H), 2.81 (t, J=5.9 Hz, 2H).

M7. 4-Chloro-N-(1-hydroxy-3,4-dihydro-1H-benzo[c][1,2]oxaborinin-7-yl)-benzamide

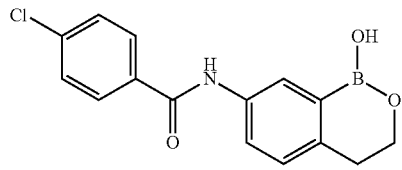 [SMILES: O=C(Nc1ccc2c(c1)B(O)OCC2)c1ccc(Cl)cc1]

M7 was prepared using a procedure similar to that of M1 with 4-chlorobenzoyl chloride replacing 4-fluoro-2-trifluoromethyl-benzoyl chloride. Data for M7: LCMS (M/Z): 302 (M+H); $^1$H NMR (DMSO-d$_6$) δ: 10.21 (s, 1H), 8.38 (s, 1H), 7.92-8.00 (m, 3H), 7.75 (dd, J=8.2, 2.3 Hz, 1H), 7.52-7.60 (m, 2H), 7.16 (d, J=8.2 Hz, 1H), 4.04 (t, J=5.9 Hz, 2H), 2.80 (t, J=5.9 Hz, 2H).

M8. 2-Bromo-N-(1-hydroxy-3,4-dihydro-1H-benzo[c][1,2]oxaborinin-7-yl)-benzamide

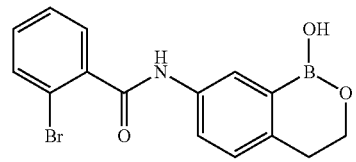 [SMILES: O=C(Nc1ccc2c(c1)B(O)OCC2)c1ccccc1Br]

M8 was prepared using a procedure similar to that of M1 with 2-bromobenzoyl chloride replacing 4-fluoro-2-trifluoromethyl-benzoyl chloride. Data for M8: LCMS (M/Z): 346 (M+H); $^1$H NMR (DMSO-d$_6$) δ: 10.34 (s, 1H), 8.38 (s, 1H), 7.93 (d, J=2.2 Hz, 1H), 7.66 (td, J=8.0, 1.6 Hz, 2H), 7.47-7.51

(m, 1H), 7.45 (td, J=7.4, 1.1 Hz, 1H), 7.38 (dd, J=7.9, 1.9 Hz, 1H), 7.14 (d, J=8.2 Hz, 1H), 4.02 (t, J=5.9 Hz, 2H), 2.79 (t, J=5.9 Hz, 2H).

M9. N-(1-Hydroxy-3,4-dihydro-1H-benzo[c][1,2]oxaborinin-7-yl)-2-methylbenzamide

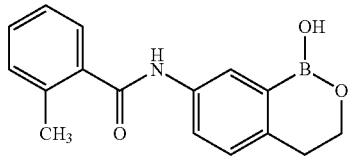

M9 was prepared using a procedure similar to that of M1 with 2-methylbenzoyl chloride replacing 4-fluoro-2-trifluoromethyl-benzoyl chloride. Data for M9: LCMS (M/Z): 282 (M+H); $^1$H NMR (DMSO-$d_6$) δ: 10.15 (s, 1H), 8.36 (s, 1H), 7.97 (d, J=2.0 Hz, 1H), 7.67 (dd, J=8.2, 2.2 Hz, 1H), 7.40 (d, J=7.5 Hz, 1H), 7.31-7.37 (m, 1H), 7.26 (d, J=7.5 Hz, 2H), 7.13 (d, J=8.2 Hz, 1H), 4.03 (t, J=5.9 Hz, 2H), 2.79 (t, J=5.9 Hz, 2H), 2.35 (s, 3H).

M10. N-(1-Hydroxy-3,4-dihydro-1H-benzo[c][1,2]oxaborinin-7-yl)-3-methylbenzamide

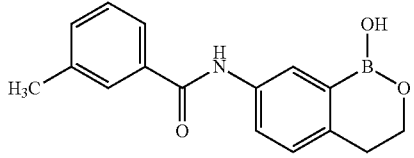

M10 was prepared using a procedure similar to that of M1 with 3-methylbenzoyl chloride replacing 4-fluoro-2-trifluoromethyl-benzoyl chloride. Data for M10: LCMS (M/Z): 282 (M+H); $^1$H NMR (DMSO-$d_6$) δ: 10.09 (s, 1H), 8.37 (s, 1H), 7.96 (d, J=2.3 Hz, 1H), 7.74-7.78 (m, 2H), 7.72 (dd, J=3.8, 2.2 Hz, 1H), 7.36 (d, J=5.7 Hz, 2H), 7.15 (d, J=8.2 Hz, 1H), 4.04 (t, J=5.9 Hz, 2H), 2.80 (t, J=5.9 Hz, 2H), 2.36 (s, 3H).

M11. N-(1-Hydroxy-3,4-dihydro-1H-benzo[c][1,2]oxaborinin-7-yl)-4-methylbenzamide

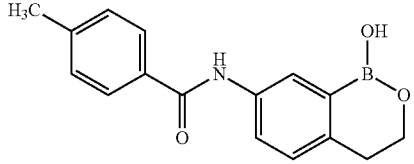

M11 was prepared using a procedure similar to that of M1 with 4-methylbenzoyl chloride replacing 4-fluoro-2-trifluoromethyl-benzoyl chloride. Data for M11: LCMS (M/Z): 282 (M+H); $^1$H NMR (DMSO-$d_6$) δ: 10.05 (s, 1H), 8.36 (s, 1H), 7.96 (d, J=2.3 Hz, 1H), 7.82-7.88 (m, J=8.2 Hz, 2H), 7.75 (dd, J=8.2, 2.3 Hz, 1H), 7.26-7.32 (m, J=7.9 Hz, 2H), 7.14 (d, J=8.2 Hz, 1H), 4.03 (t, J=5.9 Hz, 2H), 2.80 (t, J=5.9 Hz, 2H), 2.35 (s, 3H).

M12. 4-Ethyl-N-(1-hydroxy-3,4-dihydro-1H-benzo[c][1,2]oxaborinin-7-yl)-benzamide

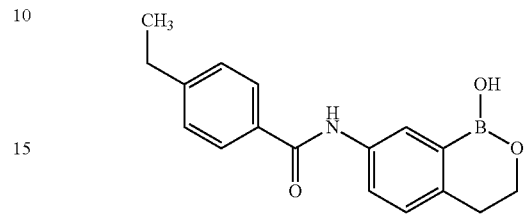

M12 was prepared using a procedure similar to that of M1 with 4-ethylbenzoyl chloride replacing 4-fluoro-2-trifluoromethyl-benzoyl chloride. Data for M12: LCMS (M/Z): 296 (M+H); $^1$H NMR (DMSO-$d_6$) δ: 10.05 (s, 1H), 8.36 (s, 1H), 7.95 (d, J=2.3 Hz, 1H), 7.83-7.89 (m, J=8.2 Hz, 2H), 7.75 (dd, J=8.2, 2.3 Hz, 1H), 7.29-7.34 (m, J=8.2 Hz, 2H), 7.14 (d, J=8.2 Hz, 1H), 4.03 (t, J=5.9 Hz, 2H), 2.79 (t, J=5.8 Hz, 2H), 2.64 (q, J=7.6 Hz, 2H), 1.17 (t, J=7.6 Hz, 3H).

M13. N-(1-Hydroxy-3,4-dihydro-1H-benzo[c][1,2]oxaborinin-7-yl)-4-propylbenzamide

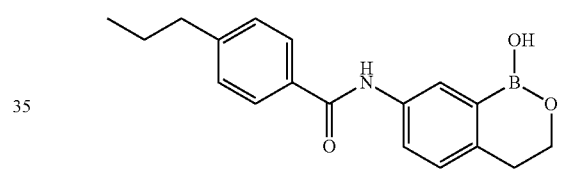

M13 was prepared using a procedure similar to that of M1 with 4-propylbenzoyl chloride replacing 4-fluoro-2-trifluoromethyl-benzoyl chloride. Data for M13: LCMS (M/Z): 310 (M+H); $^1$H NMR (DMSO-$d_6$) δ: 10.06 (s, 1H), 8.36 (s, 1H), 7.96 (d, J=2.3 Hz, 1H), 7.82-7.88 (m, J=8.2 Hz, 2H), 7.74 (dd, J=8.2, 2.3 Hz, 1H), 7.26-7.32 (m, J=8.2 Hz, 2H), 7.14 (d, J=8.2 Hz, 1H), 4.03 (t, J=5.9 Hz, 2H), 2.79 (t, J=5.8 Hz, 2H), 2.59 (t, J=7.5 Hz, 2H), 1.58 (sxt, J=7.4 Hz, 2H), 0.86 (t, J=7.3 Hz, 3H).

M14. 4-tert-Butyl-N-(1-hydroxy-3,4-dihydro-1H-benzo[c][1,2]oxaborinin-7-yl)-benzamide

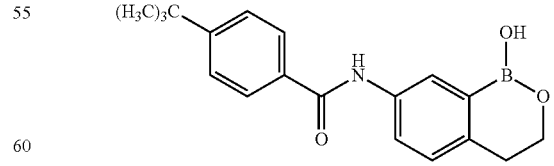

M14 was prepared using a procedure similar to that of M1 with 4-tert-butylbenzoyl chloride replacing 4-fluoro-2-trifluoromethyl-benzoyl chloride. Data for M14: LCMS (M/Z): 324 (M+H); $^1$H NMR (DMSO-$d_6$) δ: 10.07 (s, 1H), 8.37 (s, 1H), 7.96 (d, J=2.3 Hz, 1H), 7.83-7.90 (m, J=8.5 Hz, 2H), 7.75 (dd, J=8.2, 2.3 Hz, 1H), 7.47-7.53 (m, J=8.5 Hz, 2H), 7.14 (d, J=8.2 Hz, 1H), 4.03 (t, J=5.9 Hz, 2H), 2.80 (t, J=5.9 Hz, 2H), 1.28 (s, 9H).

M15. N-(1-Hydroxy-3,4-dihydro-1H-benzo[c][1,2]oxaborinin-7-yl)-2-trifluoromethyl-benzamide

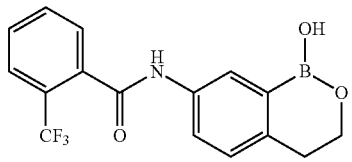

M15 was prepared using a procedure similar to that of M1 with 2-trifluoromethylbenzoyl chloride replacing 4-fluoro-2-trifluoromethyl-benzoyl chloride. Data for M15: LCMS (M/Z): 336 (M+H); $^1$H NMR (DMSO-$d_6$) δ: 10.42 (s, 1H), 8.39 (s, 1H), 7.91 (d, J=2.2 Hz, 1H), 7.80 (d, J=7.8 Hz, 1H), 7.74 (d, J=7.5 Hz, 1H), 7.60-7.69 (m, 3H), 7.15 (d, J=8.2 Hz, 1H), 4.03 (t, J=5.9 Hz, 2H), 2.80 (t, J=5.9 Hz, 2H).

M16. N-(1-Hydroxy-3,4-dihydro-1H-benzo[c][1,2]oxaborinin-7-yl)-4-trifluoromethyl-benzamide

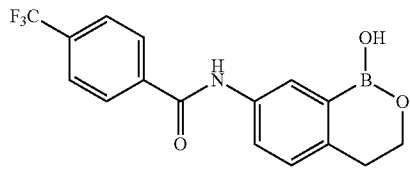

M16 was prepared using a procedure similar to that of M1 with 4-trifluoromethylbenzoyl chloride replacing 4-fluoro-2-trifluoromethyl-benzoyl chloride. Data for M16: LCMS (M/Z): 336 (M+H); $^1$H NMR (DMSO-$d_6$) δ: 10.37 (s, 1H), 8.39 (s, 1H), 8.08-8.16 (m, J=8.1 Hz, 2H), 7.96 (d, J=2.2 Hz, 1H), 7.84-7.90 (m, J=8.2 Hz, 2H), 7.76 (dd, J=8.2, 2.3 Hz, 1H), 7.17 (d, J=8.2 Hz, 1H), 4.04 (t, J=5.9 Hz, 2H), 2.81 (t, J=5.8 Hz, 2H).

M17. N-(1-Hydroxy-3,4-dihydro-1H-benzo[c][1,2]oxaborinin-7-yl)-2-methoxybenzamide

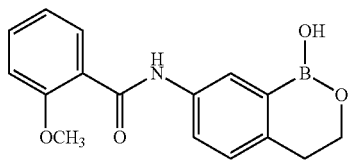 [SMILES: COc1ccccc1C(=O)Nc1ccc2c(c1)B(O)OCC2]

M17 was prepared using a procedure similar to that of M1 with 2-methoxybenzoyl chloride replacing 4-fluoro-2-trifluoromethyl-benzoyl chloride. Data for M17: LCMS (M/Z): 298 (M+H); $^1$H NMR (DMSO-$d_6$) δ: 9.98 (s, 1H), 8.38 (s, 1H), 7.91 (d, J=2.2 Hz, 1H), 7.70 (dd, J=8.1, 2.3 Hz, 1H), 7.61 (dd, J=7.6, 1.7 Hz, 1H), 7.41-7.49 (m, 1H), 7.13 (d, J=8.6 Hz, 2H), 7.02 (t, J=7.5 Hz, 1H), 4.02 (t, J=5.9 Hz, 2H), 3.86 (s, 3H), 2.75-2.82 (m, 2H).

M18. N-(1-Hydroxy-3,4-dihydro-1H-benzo[c][1,2]oxaborinin-7-yl)-3-methoxybenzamide

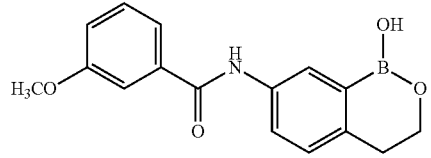 [SMILES: COc1cccc(C(=O)Nc2ccc3c(c2)B(O)OCC3)c1]

M18 was prepared using a procedure similar to that of M1 with 3-methoxybenzoyl chloride replacing 4-fluoro-2-trifluoromethyl-benzoyl chloride. Data for M18: LCMS (M/Z): 298 (M+H); $^1$H NMR (DMSO-$d_6$) δ: 10.11 (s, 1H), 8.37 (s, 1H), 7.95 (d, J=2.2 Hz, 1H), 7.75 (dd, J=8.2, 2.3 Hz, 1H), 7.51-7.54 (m, 1H), 7.47 (t, J=2.4 Hz, 1H), 7.39 (t, J=7.9 Hz, 1H), 7.15 (d, J=8.2 Hz, 1H), 7.10 (ddd, J=8.2, 2.6, 0.8 Hz, 1H), 4.03 (t, J=5.9 Hz, 2H), 3.80 (s, 3H), 2.80 (t, J=5.8 Hz, 2H).

M19. N-(1-Hydroxy-3,4-dihydro-1H-benzo[c][1,2]oxaborinin-7-yl)-4-methoxybenzamide

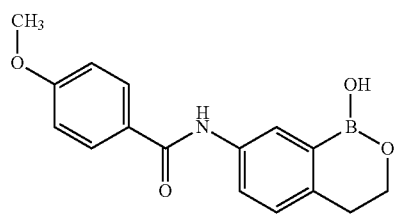

M19 was prepared using a procedure similar to that of M1 with 4-methoxybenzoyl chloride replacing 4-fluoro-2-trifluoromethyl-benzoyl chloride. Data for M19: LCMS (M/Z): 298 (M+H); $^1$H NMR (DMSO-$d_6$) δ: 9.99 (s, 1H), 8.36 (s, 1H), 7.90-7.97 (m, 3H), 7.75 (dd, J=8.2, 2.3 Hz, 1H), 7.14 (d, J=8.2 Hz, 1H), 7.01 (d, J=8.9 Hz, 2H), 4.03 (t, J=5.9 Hz, 2H), 3.80 (s, 3H), 2.80 (t, J=5.8 Hz, 2H).

M20. 2-Ethoxy-N-(1-hydroxy-3,4-dihydro-1H-benzo[c][1,2]oxaborinin-7-yl)-benzamide

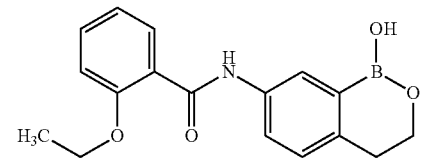 [SMILES: CCOc1ccccc1C(=O)Nc1ccc2c(c1)B(O)OCC2]

M20 was prepared using a procedure similar to that of M1 with 2-ethoxybenzoyl chloride replacing 4-fluoro-2-trifluoromethyl-benzoyl chloride. Data for M20: LCMS (M/Z): 312 (M+H); $^1$H NMR (DMSO-$d_6$) δ: 10.02 (s, 1H), 8.39 (s, 1H), 7.92 (d, J=2.2 Hz, 1H), 7.69 (dd, J=7.8, 1.9 Hz, 2H), 7.41-7.49 (m, 1H), 7.14 (dd, J=8.0, 6.3 Hz, 2H), 7.03 (t, J=7.5 Hz, 1H), 4.16 (q, J=6.9 Hz, 2H), 4.03 (t, J=5.9 Hz, 2H), 2.80 (t, J=5.8 Hz, 2H), 1.38 (t, J=6.9 Hz, 3H).

M21. N-(1-Hydroxy-3,4-dihydro-1H-benzo[c][1,2]oxaborinin-7-yl)-4-pentyloxy-benzamide

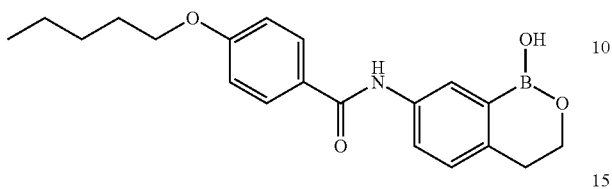

M21 was prepared using a procedure similar to that of M1 with 4-pentyloxybenzoyl chloride replacing 4-fluoro-2-trifluoromethyl-benzoyl chloride. Data for M21: LCMS (M/Z): 354 (M+H); $^1$H NMR (DMSO-$d_6$) δ: 9.97 (s, 1H), 8.35 (s, 1H), 7.94 (d, J=2.2 Hz, 1H), 7.91 (d, J=8.8 Hz, 2H), 7.74 (dd, J=8.2, 2.3 Hz, 1H), 7.13 (d, J=8.2 Hz, 1H), 6.99 (d, J=8.8 Hz, 2H), 3.97-4.06 (m, 4H), 2.79 (t, J=5.8 Hz, 2H), 1.65-1.74 (m, 2H), 1.28-1.40 (m, 4H), 0.86 (t, J=6.0 Hz, 3H).

M22. N-(1-Hydroxy-3,4-dihydro-1H-benzo[c][1,2]oxaborinin-7-yl)-4-trifluoromethoxy-benzamide

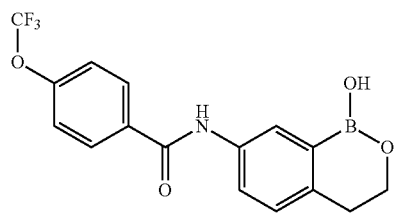 [SMILES: O=C(Nc1ccc2c(c1)B(O)OCC2)c1ccc(SC(F)(F)F)cc1]

M22 was prepared using a procedure similar to that of M1 with 4-trifluoromethoxybenzoyl chloride replacing 4-fluoro-2-trifluoromethyl-benzoyl chloride. Data for M22: LCMS (M/Z): 352 (M+H); $^1$H NMR (DMSO-$d_6$) δ: 10.25 (s, 1H), 8.39 (s, 1H), 8.02-8.09 (m, 2H), 7.95 (d, J=2.3 Hz, 1H), 7.75 (dd, J=8.2, 2.4 Hz, 1H), 7.49 (d, J=8.0 Hz, 2H), 7.16 (d, J=8.2 Hz, 1H), 4.04 (t, J=5.9 Hz, 2H), 2.81 (t, J=5.8 Hz, 2H).

M23. 4-Trifluoromethylsulfanyl-N-(1-hydroxy-3,4-dihydro-1H-benzo[c][1,2]oxaborinin-7-yl)-benzamide

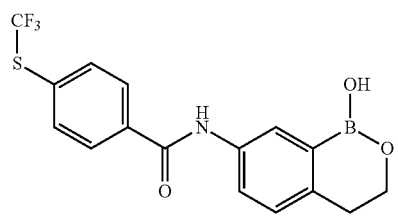

M23 was prepared using a procedure similar to that of M1 with 4-trifluoromethylbenzoyl chloride replacing 4-fluoro-2-trifluoromethyl-benzoyl chloride. Data for M23: LCMS (M/Z): 268 (M+H); $^1$H NMR (DMSO-$d_6$) δ: 10.33 (s, 1H), 8.38 (s, 1H), 8.01-8.05 (m, 2H), 7.96 (d, J=2.2 Hz, 1H), 7.81-7.86 (m, J=8.2 Hz, 2H), 7.74 (dd, J=8.2, 2.3 Hz, 1H), 7.16 (d, J=8.2 Hz, 1H), 4.03 (t, J=5.9 Hz, 2H), 2.80 (t, J=5.9 Hz, 2H).

M24. 4-Cyano-N-(1-hydroxy-3,4-dihydro-1H-benzo[c][1,2]oxaborinin-7-yl)-benzamide

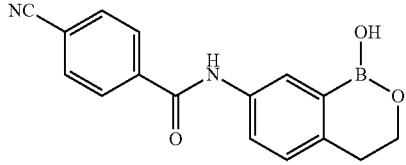 [SMILES: N#Cc1ccc(C(=O)Nc2ccc3c(c2)B(O)OCC3)cc1]

M24 was prepared using a procedure similar to that of M1 with 4-cyanobenzoyl chloride replacing 4-fluoro-2-trifluoromethyl-benzoyl chloride. Data for M24: LCMS (M/Z): 293 (M+H); $^1$H NMR (DMSO-$d_6$) δ: 10.38 (s, 1H), 8.39 (s, 1H), 8.05-8.11 (m, 2H), 7.94-8.01 (m, 3H), 7.75 (dd, J=8.2, 2.4 Hz, 1H), 7.17 (d, J=8.2 Hz, 1H), 4.03 (t, J=5.8 Hz, 2H), 2.80 (t, J=5.8 Hz, 2H).

M25. N-(1-Hydroxy-3,4-dihydro-1H-benzo[c][1,2]oxaborinin-7-yl)-2-nitrobenzamide

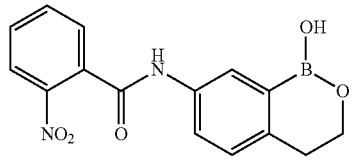 [SMILES: O=C(Nc1ccc2c(c1)B(O)OCC2)c1ccccc1[N+](=O)[O-]]

M25 was prepared using a procedure similar to that of M1 with 2-nitrobenzoyl chloride replacing 4-fluoro-2-trifluoromethyl-benzoyl chloride. Data for M25: LCMS (M/Z): 313 (M+H); $^1$H NMR (DMSO-$d_6$) δ: 10.53 (s, 1H), 8.40 (s, 1H), 8.10 (d, J=8.2 Hz, 1H), 7.88 (d, J=2.2 Hz, 1H), 7.80-7.84 (m, 1H), 7.72 (d, J=7.2 Hz, 2H), 7.63 (dd, J=8.2, 2.3 Hz, 1H), 7.16 (d, J=8.2 Hz, 1H), 4.03 (t, J=5.9 Hz, 2H), 2.81 (t, J=5.9 Hz, 2H).

M26. 2,4-Difluoro-N-(1-hydroxy-3,4-dihydro-1H-benzo[c][1,2]oxaborinin-7-yl)-benzamide

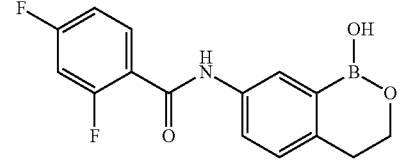 [SMILES: O=C(Nc1ccc2c(c1)B(O)OCC2)c1ccc(F)cc1F]

M26 was prepared using a procedure similar to that of M1 with 2,4-difluorobenzoyl chloride replacing 4-fluoro-2-trifluoromethyl-benzoyl chloride. Data for M26: LCMS (M/Z): 629 (2M+23); $^1$H NMR (DMSO-$d_6$) δ: 10.28 (s, 1H), 8.39 (s, 1H), 7.89-7.94 (m, 1H), 7.65-7.75 (m, 2H), 7.32-7.41 (m, 1H), 7.13-7.21 (m, 2H), 4.03 (t, J=5.9 Hz, 2H), 2.80 (t, J=5.9 Hz, 2H).

M27. 2,4-Dichloro-N-(1-hydroxy-3,4-dihydro-1H-benzo[c][1,2]oxaborinin-7-yl)-benzamide

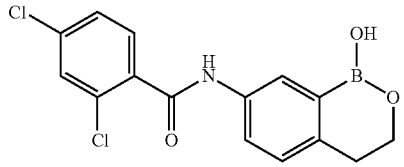

M27 was prepared using a procedure similar to that of M1 with 2,4-dichlorobenzoyl chloride replacing 4-fluoro-2-trifluoromethyl-benzoyl chloride. Data for M27: LCMS (M/Z): 336 (M+H); $^1$H NMR (DMSO-$d_6$) δ: 10.40 (s, 1H), 8.40 (s, 1H), 7.91 (d, J=2.2 Hz, 1H), 7.72 (d, J=2.0 Hz, 1H), 7.65 (dd, J=8.2, 2.3 Hz, 1H), 7.56-7.60 (m, 1H), 7.52 (d, J=2.0 Hz, 1H), 7.15 (d, J=8.2 Hz, 1H), 4.03 (t, J=5.8 Hz, 2H), 2.80 (t, J=5.8 Hz, 2H).

M28. 2-Chloro-4-fluoro-N-(1-hydroxy-3,4-dihydro-1H-benzo[c][1,2]oxaborinin-7-yl)-benzamide

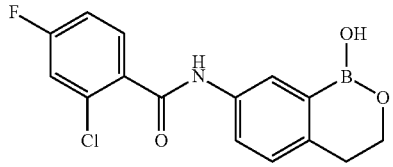 [SMILES: O=C(Nc1ccc2c(c1)B(O)OCC2)c1ccc(F)cc1Cl]

M28 was prepared using a procedure similar to that of M1 with 2-chloro-4-fluorobenzoyl chloride replacing 4-fluoro-2-trifluoromethyl-benzoyl chloride. Data for M28: LCMS (M/Z): 320 (M+H); $^1$H NMR (DMSO-$d_6$) δ: 10.37 (s, 1H), 8.39 (s, 1H), 7.92 (d, J=2.3 Hz, 1H), 7.64 (ddd, J=10.4, 8.2, 2.4 Hz, 2H), 7.54 (dd, J=9.1, 2.5 Hz, 1H), 7.30 (td, J=8.5, 2.5 Hz, 1H), 7.15 (d, J=8.2 Hz, 1H), 4.03 (t, J=5.9 Hz, 2H), 2.80 (t, J=5.8 Hz, 2H).

M29. 4-Chloro-2-fluoro-N-(1-hydroxy-3,4-dihydro-1H-benzo[c][1,2]oxaborinin-7-yl)-benzamide

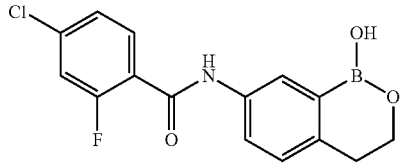 [SMILES: O=C(Nc1ccc2c(c1)B(O)OCC2)c1ccc(Cl)cc1F]

M29 was prepared using a procedure similar to that of M1 with 4-chloro-2-fluorobenzoyl chloride replacing 4-fluoro-2-trifluoromethyl-benzoyl chloride. Data for M29: LCMS (M/Z): 320 (M+H); $^1$H NMR (DMSO-$d_6$) δ: 10.32 (s, 1H), 8.40 (s, 1H), 7.90 (d, J=2.1 Hz, 1H), 7.63-7.70 (m, 2H), 7.57 (dd, J=10.0, 1.9 Hz, 1H), 7.39 (dd, J=8.3, 1.9 Hz, 1H), 7.16 (d, J=8.2 Hz, 1H), 4.03 (t, J=5.9 Hz, 2H), 2.80 (t, J=5.9 Hz, 2H).

M30. 3-Chloro-4-fluoro-N-(1-hydroxy-3,4-dihydro-1H-benzo[c][1,2]oxaborinin-7-yl)-benzamide

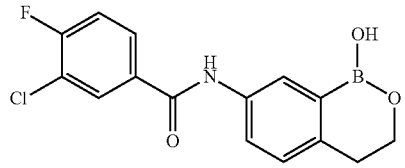 [SMILES: O=C(Nc1ccc2c(c1)B(O)OCC2)c1ccc(F)c(Cl)c1]

M30 was prepared using a procedure similar to that of M1 with 3-chloro-4-fluorobenzoyl chloride replacing 4-fluoro-2-trifluoromethyl-benzoyl chloride. Data for M30: LCMS (M/Z): 320 (M+H); $^1$H NMR (DMSO-$d_6$) δ: 10.25 (s, 1H), 8.39 (s, 1H), 8.18 (dd, J=7.2, 2.2 Hz, 1H), 7.97 (ddd, J=8.7, 4.8, 2.2 Hz, 1H), 7.94 (d, J=2.3 Hz, 1H), 7.76 (dd, J=8.2, 2.3 Hz, 1H), 7.55 (t, J=8.9 Hz, 1H), 7.16 (d, J=8.2 Hz, 1H), 4.04 (t, J=5.9 Hz, 2H), 2.81 (t, J=5.9 Hz, 2H).

M31. 2-Chloro-6-fluoro-N-(1-hydroxy-3,4-dihydro-1H-benzo[c][1,2]oxaborinin-7-yl)-benzamide

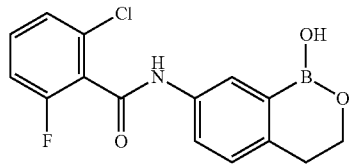 [SMILES: O=C(Nc1ccc2c(c1)B(O)OCC2)c1c(F)cccc1Cl]

M31 was prepared using a procedure similar to that of M1 with 2-chloro-6-fluorobenzoyl chloride replacing 4-fluoro-2-trifluoromethyl-benzoyl chloride. Data for M31: LCMS (M/Z): 320 (M+H); $^1$H NMR (DMSO-$d_6$) δ: 10.64 (s, 1H), 8.42 (s, 1H), 7.91 (d, J=2.2 Hz, 1H), 7.63 (dd, J=8.2, 2.3 Hz, 1H), 7.50 (td, J=8.2, 6.2 Hz, 1H), 7.40 (d, J=8.0 Hz, 1H), 7.30-7.36 (m, 1H), 7.17 (d, J=8.2 Hz, 1H), 4.03 (t, J=5.9 Hz, 2H), 2.80 (t, J=5.8 Hz, 2H).

M32. 5-Chloro-2-fluoro-N-(1-hydroxy-3,4-dihydro-1H-benzo[c][1,2]oxaborinin-7-yl)-benzamide

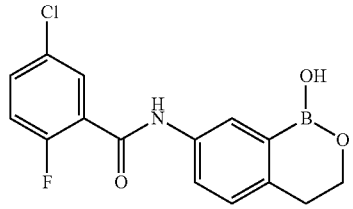 [SMILES: O=C(Nc1ccc2c(c1)B(O)OCC2)c1cc(Cl)ccc1F]

M32 was prepared using a procedure similar to that of M1 with 5-chloro-2-fluorobenzoyl chloride replacing 4-fluoro-2-trifluoromethyl-benzoyl chloride. Data for M32: LCMS (M/Z): 320 (M+H); $^1$H NMR (DMSO-$d_6$) δ: 10.38 (s, 1H), 8.39 (s, 1H), 7.90 (d, J=2.2 Hz, 1H), 7.67-7.71 (m, 1H), 7.66

(d, J=2.3 Hz, 1H), 7.59 (ddd, J=8.9, 4.3, 2.8 Hz, 1H), 7.37 (t, J=9.2 Hz, 1H), 7.15 (d, J=8.2 Hz, 1H), 4.02 (t, J=5.9 Hz, 2H), 2.80 (t, J=5.9 Hz, 2H).

M33. 3-Chloro-2-fluoro-N-(1-hydroxy-3,4-dihydro-1H-benzo[c][1,2]oxaborinin-7-yl)-benzamide

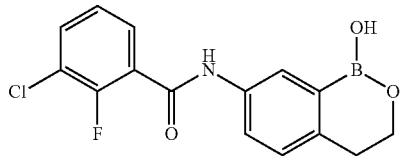 [SMILES: O=C(Nc1ccc2c(c1)B(O)OCC2)c1cccc(Cl)c1F]

M33 was prepared using a procedure similar to that of M1 with 3-chloro-2-fluorobenzoyl chloride replacing 4-fluoro-2-trifluoromethyl-benzoyl chloride. Data for M33: LCMS (M/Z): 320 (M+H); $^1$H NMR (DMSO-$d_6$) δ: 10.42 (s, 1H), 8.40 (s, 1H), 7.91 (d, J=2.2 Hz, 1H), 7.69-7.74 (m, 1H), 7.67 (dd, J=8.2, 2.3 Hz, 1H), 7.58 (td, J=7.0, 1.6 Hz, 1H), 7.31 (t, J=7.9 Hz, 1H), 7.16 (d, J=8.2 Hz, 1H), 4.03 (t, J=5.9 Hz, 2H), 2.80 (t, J=5.9 Hz, 2H).

M34. 2-Chloro-N-(1-hydroxy-3,4-dihydro-1H-benzo[c][1,2]oxaborinin-7-yl)-4-nitro-benzamide

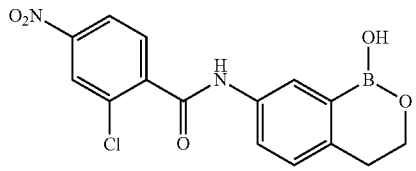 [SMILES: O=C(Nc1ccc2c(c1)B(O)OCC2)c1ccc([N+](=O)[O-])cc1Cl]

M34 was prepared using a procedure similar to that of M1 with 2-chloro-4-nitrobenzoyl chloride replacing 4-fluoro-2-trifluoromethyl-benzoyl chloride. Data for M34: LCMS (M/Z): 347 (M+H); $^1$H NMR (DMSO-$d_6$) δ: 10.61 (s, 1H), 8.42 (s, 1H), 8.38 (d, J=2.1 Hz, 1H), 8.25 (dd, J=8.4, 2.2 Hz, 1H), 7.91 (d, J=2.3 Hz, 1H), 7.85 (d, J=8.4 Hz, 1H), 7.66 (dd, J=8.2, 2.4 Hz, 1H), 7.18 (d, J=8.2 Hz, 1H), 4.04 (t, J=5.9 Hz, 2H), 2.81 (t, J=5.9 Hz, 2H).

M35. 2-Fluoro-N-(1-hydroxy-3,4-dihydro-1H-benzo[c][1,2]oxaborinin-7-yl)-3-trifluoromethyl-benzamide

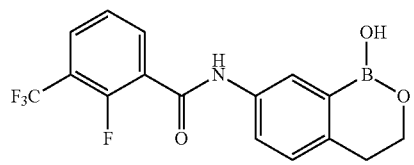 [SMILES: O=C(Nc1ccc2c(c1)B(O)OCC2)c1cccc(C(F)(F)F)c1F]

M35 was prepared using a procedure similar to that of M1 with 3-trifluoromethyl-2-fluorobenzoyl chloride replacing 4-fluoro-2-trifluoromethylbenzoyl chloride. Data for M35: LCMS (M/Z): 354 (M+H); $^1$H NMR (DMSO-$d_6$) δ: 10.50 (s, 1H), 8.41 (s, 1H), 7.87-7.97 (m, 3H), 7.68 (dd, J=8.2, 2.3 Hz, 1H), 7.50 (t, J=7.7 Hz, 1H), 7.17 (d, J=8.2 Hz, 1H), 4.03 (t, J=5.9 Hz, 2H), 2.80 (t, J=5.9 Hz, 2H).

M36. 2-Fluoro-N-(1-hydroxy-3,4-dihydro-1H-benzo[c][1,2]oxaborinin-7-yl)-4-trifluoromethyl-benzamide

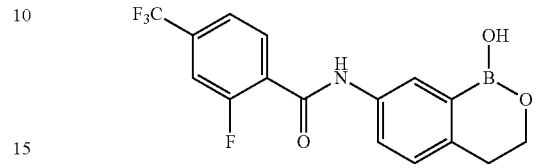

M36 was prepared using a procedure similar to that of M1 with 2-fluoro-4-trifluoromethylbenzoyl chloride replacing 4-fluoro-2-trifluoromethyl-benzoyl chloride. Data for M36: LCMS (M/Z): 354 (M+H); $^1$H NMR (DMSO-$d_6$) δ: 10.48 (s, 1H), 8.41 (s, 1H), 7.91 (d, J=2.2 Hz, 1H), 7.81-7.87 (m, 2H), 7.65-7.70 (m, 2H), 7.17 (d, J=8.2 Hz, 1H), 4.03 (t, J=5.9 Hz, 2H), 2.80 (t, J=5.8 Hz, 2H).

M37. 2-Fluoro-N-(1-hydroxy-3,4-dihydro-1H-benzo[c][1,2]oxaborinin-7-yl)-5-trifluoromethyl-benzamide

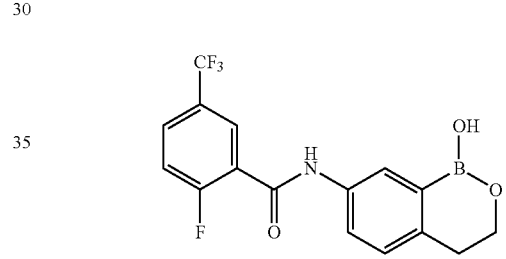

M37 was prepared using a procedure similar to that of M1 with 2-fluoro-5-trifluoromethylbenzoyl chloride replacing 4-fluoro-2-trifluoromethyl-benzoyl chloride. Data for M37: LCMS (M/Z): 354 (M+H); $^1$H NMR (DMSO-$d_6$) δ: 10.46 (s, 1H), 8.40 (s, 1H), 8.01 (dd, J=6.0, 2.1 Hz, 1H), 7.94 (dd, J=8.2, 4.5 Hz, 1H), 7.90 (d, J=2.2 Hz, 1H), 7.69 (dd, J=8.2, 2.3 Hz, 1H), 7.57 (t, J=9.2 Hz, 1H), 7.17 (d, J=8.2 Hz, 1H), 4.03 (t, J=5.9 Hz, 2H), 2.80 (t, J=5.8 Hz, 2H).

M38. N-(1-Hydroxy-3,4-dihydro-1H-benzo[c][1,2]oxaborinin-7-yl)-2,4-bis-trifluoromethyl-benzamide

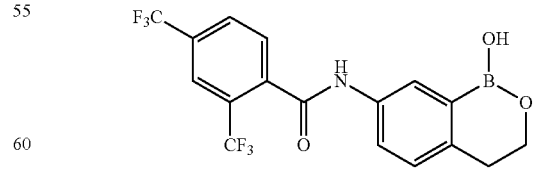

M38 was prepared using a procedure similar to that of M1 with 2,4 di(trifluoromethyl)benzoyl chloride replacing 4-fluoro-2-trifluoromethyl-benzoyl chloride. Data for M38: LCMS (M/Z): 336 (M+H); $^1$H NMR (DMSO-$d_6$) δ: 10.37 (s, 1H), 8.39 (s, 1H), 8.08-8.16 (m, J=8.1 Hz, 2H), 7.96 (d, J=2.2

Hz, 1H), 7.84-7.90 (m, J=8.2 Hz, 2H), 7.76 (dd, J=8.2, 2.3 Hz, 1H), 7.17 (d, J=8.2 Hz, 1H), 4.04 (t, J=5.9 Hz, 2H), 2.81 (t, J=5.8 Hz, 2H).

M39. N-(1-Hydroxy-3,4-dihydro-1H-benzo[c][1,2]oxaborinin-7-yl)-2,4-dimethoxybenzamide

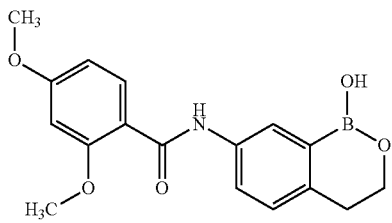 [SMILES: COc1ccc(C(=O)Nc2ccc3c(c2)B(O)OCC3)c(OC)c1]

M39 was prepared using a procedure similar to that of M1 with 2,4 dimethoxybenzoyl chloride replacing 4-fluoro-2-trifluoromethyl-benzoyl chloride. Data for M39: LCMS (M/Z): 328 (M+H); $^1$H NMR (DMSO-$d_6$) δ: 9.80 (s, 1H), 8.38 (s, 1H), 7.88 (d, J=2.2 Hz, 1H), 7.69-7.76 (m, 2H), 7.13 (d, J=8.2 Hz, 1H), 6.67 (d, J=2.2 Hz, 1H), 6.63 (dd, J=8.6, 2.3 Hz, 1H), 4.03 (t, J=5.9 Hz, 2H), 3.92 (s, 3H), 3.80 (s, 3H), 2.79 (t, J=5.9 Hz, 2H).

M40. N-(1-Hydroxy-3,4-dihydro-1H-benzo[c][1,2]oxaborinin-7-yl)-terephthalamic acid methyl ester

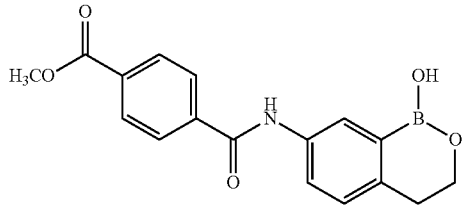 [SMILES: COC(=O)c1ccc(C(=O)Nc2ccc3c(c2)B(O)OCC3)cc1]

M40 was prepared using a procedure similar to that of M1 with 4-methoxycarbonylbenzoyl chloride replacing 4-fluoro-2-trifluoromethyl-benzoyl chloride. Data for M40: LCMS (M/Z): 326 (M+H); $^1$H NMR (DMSO-$d_6$) δ: 10.33 (s, 1H), 8.38 (s, 1H), 8.02-8.08 (m, 4H), 7.97 (d, J=2.2 Hz, 1H), 7.75 (dd, J=8.2, 2.3 Hz, 1H), 7.16 (d, J=8.2 Hz, 1H), 4.03 (t, J=5.9 Hz, 2H), 3.86 (s, 3H), 2.80 (t, J=5.9 Hz, 2H).

M41. N-(1-Hydroxy-3,4-dihydro-1H-benzo[c][1,2]oxaborinin-7-yl)-benzamide

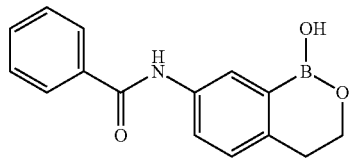 [SMILES: O=C(Nc1ccc2c(c1)B(O)OCC2)c1ccccc1]

M41 was prepared using a procedure similar to that of M1 with benzoyl chloride replacing 4-fluoro-2-trifluoromethyl-benzoyl chloride. Data for M41: LCMS (M/Z): 268 (M+H); $^1$H NMR (DMSO-$d_6$) δ: 10.15 (s, 1H), 8.38 (s, 1H), 7.97 (d, J=2.3 Hz, 1H), 7.91-7.95 (m, 2H), 7.76 (dd, J=8.2, 2.3 Hz, 1H), 7.46-7.59 (m, 4H), 7.15 (d, J=8.2 Hz, 1H), 4.04 (t, J=5.9 Hz, 2H), 2.80 (t, J=5.9 Hz, 2H).

M42. Naphthalene-1-carboxylic acid (1-hydroxy-3,4-dihydro-1H-benzo[c][1,2]oxaborinin-7-yl)-amide

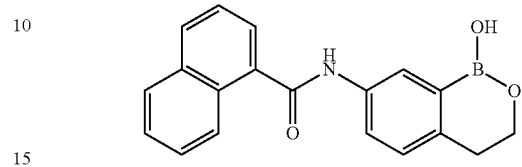

M42 was prepared using a procedure similar to that of M1. Data for M42: LCMS (M/Z): 318 (M+H); $^1$H NMR (DMSO-$d_6$) δ: 10.45 (s, 1H), 8.39 (s, 1H), 8.12-8.18 (m, 1H), 8.01-8.07 (m, 2H), 7.98 (dd, J=5.2, 1.7 Hz, 1H), 7.75 (dd, J=8.1, 2.2 Hz, 1H), 7.70 (d, J=6.3 Hz, 1H), 7.52-7.60 (m, 3H), 7.18 (d, J=8.2 Hz, 1H), 4.05 (t, J=5.9 Hz, 2H), 2.82 (t, J=5.8 Hz, 2H).

M43. 4-Chloro-N-(1-hydroxy-3,4-dihydro-1H-benzo[c][1,2]oxaborinin-7-yl)-benzenesulfonamide

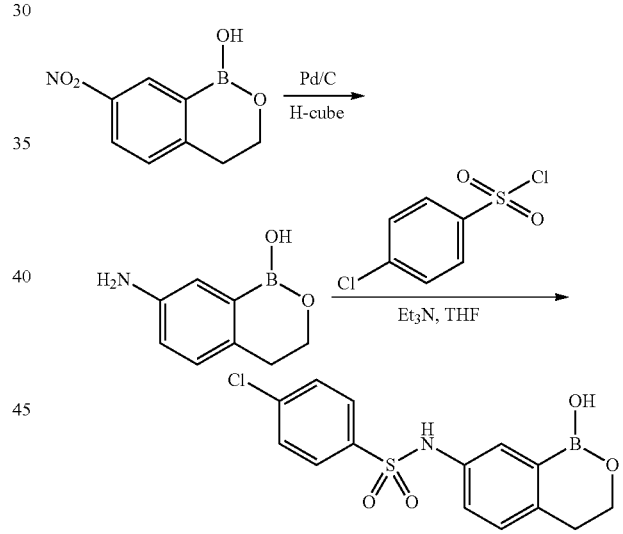

A solution of 7-nitro-3,4-dihydro-benzo[c][1,2]oxaborinin-1-ol (694.6 mg, 3.6 mmol) in THF (70 mL) was passed through H-cube equipped with a 10% Pd/C cartridge. The collected light yellow solution was treated with Et$_3$N (0.6 mL, 4.3 mmol, 1.2 eq.) and divided evenly into 12 portions. To a portion of the solution was added 4-chloro-benzenesulfonyl chloride (63.3 mg, 0.29 mmol). The resulting mixture was stirred at room temperature overnight. The reaction solution was diluted with EtOAc (20 mL), washed with 1N HCl (10 mL), H$_2$O (10 mL), brine (10 mL) and concentrated under reduced pressure. The residue was dissolved in minimal amount of THF and then titrated with heptanes to vive a white suspension. The precipitate was collected by filtration, washed with heptanes to give the title compound as a white solid. LCMS (M/Z): 338 (M+H); $^1$H NMR (DMSO-$d_6$) δ: 10.17 (s, 1H), 8.39 (s, 1H), 7.65-7.70 (m, 2H), 7.56-7.61 (m, 2H), 7.32 (d, J=1.8 Hz, 1H), 7.02-7.08 (m, 2H), 3.96 (t, J=5.9 Hz, 2H), 2.72 (t, J=5.9 Hz, 2H).

M44. N-(1-Hydroxy-3,4-dihydro-1H-benzo[c][1,2]oxaborinin-7-yl)-2-methylbenzenesulfonamide

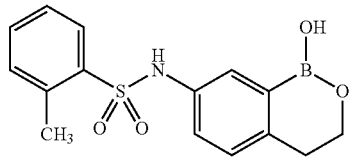 [SMILES: Cc1ccccc1S(=O)(=O)Nc1ccc2c(c1)B(O)OCC2]

M44 was prepared in a manner similar to that of M43 with 2-methylbenzenesulfonyl chloride replacing 4-chlorobenzenesulfonyl chloride. Data for M44: LCMS (m/e): 318 (M+H); $^1$H NMR (400 MHz, DMSO-d$_6$) δ ppm 2.58 (s, 3H) 2.73 (t, J=5.8 Hz, 2H) 3.98 (t, J=5.8 Hz, 2H) 7.01-7.06 (m, 1H) 7.09 (dd, 1H) 7.29-7.40 (m, 3H) 7.48 (t, J=7.4 Hz, 1H) 7.83 (d, J=7.5 Hz, 1H) 8.39 (br. s., 1H) 10.23 (s, 1H).

M45. N-(1-Hydroxy-3,4-dihydro-1H-benzo[c][1,2]oxaborinin-7-yl)-3-methylbenzenesulfonamide

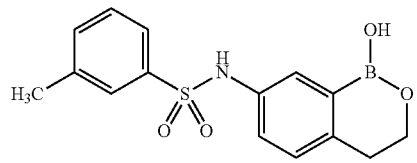 [SMILES: Cc1cccc(S(=O)(=O)Nc2ccc3c(c2)B(O)OCC3)c1]

M45 was prepared in a manner similar to that of M43 with 3-methylbenzenesulfonyl chloride replacing 4-chlorobenzenesulfonyl chloride. Data for M45: LCMS (m/e): 318 (M+H); $^1$H NMR (400 MHz, DMSO-d$_6$) δ ppm 2.33 (s, 3H) 2.75 (t, J=5.8 Hz, 2H) 3.99 (t, J=5.8 Hz, 2H) 7.03-7.08 (m, 1H) 7.08-7.14 (m, 1H) 7.37 (d, J=2.1 Hz, 1H) 7.41 (d, J=5.3 Hz, 2H) 7.52 (d, J=3.9 Hz, 1H) 7.57 (s, 1H) 8.40 (br. s., 1H) 10.08 (s, 1H).

M46. N-(1-Hydroxy-3,4-dihydro-1H-benzo[c][1,2]oxaborinin-7-yl)-4-methylbenzenesulfonamide

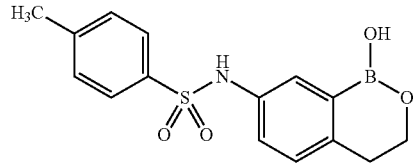 [SMILES: Cc1ccc(S(=O)(=O)Nc2ccc3c(c2)B(O)OCC3)cc1]

M46 was prepared in a manner similar to that of M43 with 4-methylbenzenesulfonyl chloride replacing 4-chlorobenzenesulfonyl chloride. Data for M46: LCMS (M/Z): 318 (M+H); $^1$H NMR (DMSO-d$_6$) δ: 10.02 (s, 1H), 8.37 (s, 1H), 7.55-7.60 (m, J=8.3 Hz, 2H), 7.32 (d, J=2.3 Hz, 1H), 7.27-7.31 (m, J=8.0 Hz, 2H), 7.06 (d, J=2.4 Hz, 1H), 6.99-7.03 (m, 1H), 3.95 (t, J=6.0 Hz, 2H), 2.70 (t, J=5.9 Hz, 2H), 2.29 (s, 3H).

M47. N-(1-Hydroxy-3,4-dihydro-1H-benzo[c][1,2]oxaborinin-7-yl)-4-isopropyl-benzenesulfonamide

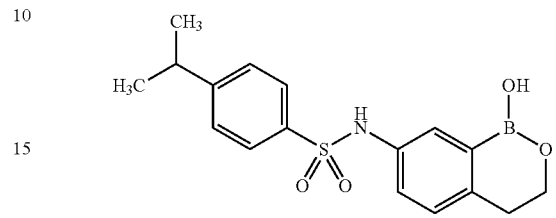

M47 was prepared in a manner similar to that of M43 with 4-isopropylbenzenesulfonyl chloride replacing 4-chlorobenzenesulfonyl chloride. Data for M47: LCMS (M/Z): 346 (M+H); $^1$H NMR (DMSO-d$_6$) δ: 10.06 (s, 1H), 8.37 (s, 1H), 7.60-7.65 (m, J=8.4 Hz, 2H), 7.35-7.39 (m, J=8.3 Hz, 2H), 7.34 (d, J=2.3 Hz, 1H), 7.08 (d, J=2.4 Hz, 1H), 7.00-7.04 (m, 1H), 3.95 (t, J=5.9 Hz, 2H), 2.88 (quin, J=6.9 Hz, 1H), 2.70 (t, J=5.9 Hz, 2H), 1.13 (d, J=6.9 Hz, 6H).

M48. N-(1-Hydroxy-3,4-dihydro-1H-benzo[c][1,2]oxaborinin-7-yl)-3-methoxybenzenesulfonamide

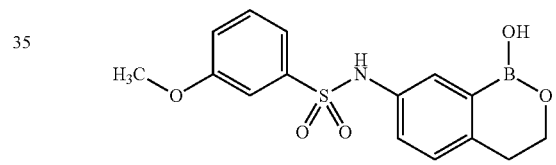

M48 was prepared in a manner similar to that of M43 with 3-methoxybenzenesulfonyl chloride replacing 4-chlorobenzenesulfonyl chloride. Data for M48: LCMS (m/e): 334 (M+H); $^1$H NMR (400 MHz, DMSO-d$_6$) d ppm 2.75 (t, J=5.8 Hz, 2H) 3.76 (s, 3H) 4.00 (t, J=5.8 Hz, 2H) 7.01-7.10 (m, 1H) 7.14 (dd, J=6.2, 2.2 Hz, 1H) 7.24 (d, J=2.0 Hz, 1H) 7.29 (d, J=7.8 Hz, 1H) 7.39 (d, J=2.1 Hz, 1H) 7.44 (t, J=8.0 Hz, 1H) 8.42 (br. s., 1H) 10.11 (s, 1H).

M49. N-(1-Hydroxy-3,4-dihydro-1H-benzo[c][1,2]oxaborinin-7-yl)-4-nitro-benzenesulfonamide

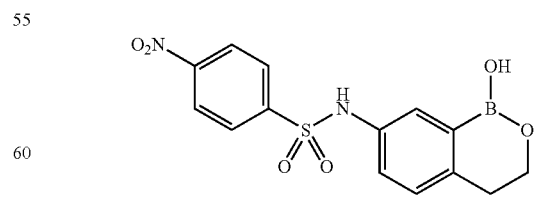

M49 was prepared in a manner similar to that of M43 with 4-nitrobenzenesulfonyl chloride replacing 4-chlorobenzenesulfonyl chloride. Data for M49: LCMS (M/Z): 349 (M+H); $^1$H NMR (DMSO-d$_6$) δ: 10.43 (s, 1H), 8.41 (s, 1H), 8.30-8.35

(m, 2H), 7.90-7.95 (m, 2H), 7.34 (d, J=2.1 Hz, 1H), 7.03-7.10 (m, 2H), 3.96 (t, J=5.9 Hz, 2H), 2.72 (t, J=5.9 Hz, 2H).

M50. 4-Fluoro-N-(1-hydroxy-4-methyl-3,4-dihydro-1H-benzo[c][1,2]oxaborinin-7-yl)-2-methyl-benzamide

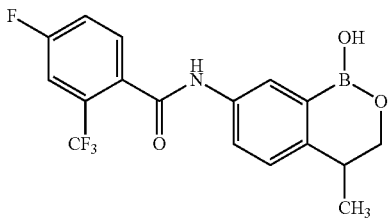 [SMILES: CC1COB(O)c2cc(NC(=O)c3ccc(F)cc3C(F)(F)F)ccc21]

(2-Bromophenyl)-acetic acid methyl ester

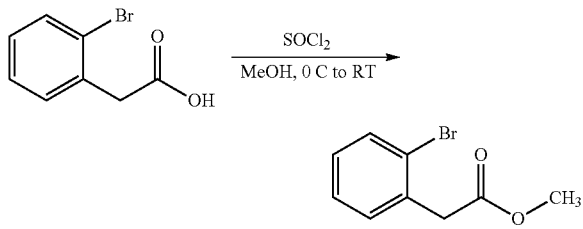

In a 250 mL round bottom flask, 5.0046 g (23.2729 mmol, 1.0 eq) of 2-(Bromophenyl)acetic acid was dissolved in 100 mL of clean, dry MeOH under $N_2$ atmosphere. This solution was cooled to 0° C. using a wet ice bath and stirred for five minutes. To the stirring solution was added 2.55 mL (34.9093 mmol, 1.5 eq) of thionyl chloride dropwise over a period of five minutes. The reaction was then allowed to stir overnight, gradually warming to room temperature. The following morning, the solvent was removed under reduced pressure. The resultant deep yellow oil was taken up in 50 mL of DCM. The solution was then washed with 50 mL of saturated $NaHCO_3$ (aq) solution. The organic layer immediately became colorless. The layers were separated and the organic layer was washed with brine (1×30 mL) and then dried over $Na_2SO_4$. The solution was decanted and then solvent was removed under reduced pressure. A clear oil was isolated. LCMS (m/e): 230 (M+H); $^1$H NMR (400 MHz, METHANOL-$d_4$) δ ppm 3.69 (s, 3H) 3.82 (s, 2H) 7.10-7.25 (m, 1H) 7.26-7.40 (m, 2H) 7.58 (d, J=7.91 Hz, 1H).

2-(2-Bromophenyl)-propionic acid methyl ester

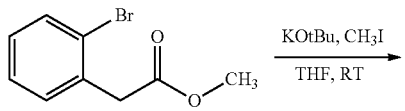

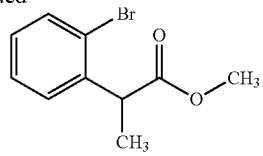

In a 500 mL round bottom flask, 5.1460 g (45.8603 mmol, 2.2 eq) of the potassium t-butoxide was suspended in 190 mL of clean, dry THF under $N_2$ atmosphere. To this was added 4.7751 g (20.8456 mmol, 1.0 eq) of the methyl ester dissolved in 10 mL of THF. The solution immediately became a cloudy yellow. The reaction solution was allowed to stir for thirty minutes at room temperature. To the stirred reaction was then added 2.86 mL (48.8603 mmol, 2.2 eq) of the methyl iodide in one portion. The reaction was allowed to stir overnight at room temperature. The following morning, the reaction was diluted with 200 mL of $H_2O$. The layers were separated and the aqueous solution was extracted with EtOAc (2×100 mL). The organic layers were combined, washed with brine (1×100 mL) and dried over $Na_2SO_4$. The solvent was removed under reduced pressure, yielding a deep yellow oil. The oil was taken up in EtOAc and concentrated onto Celite. The product was then purified using silica gel column chromatography, eluting a gradient of 100% heptane to 50% EtOAc in heptane. A colorless oil was isolated. LCMS (m/e): 244 (M+H); $^1$H NMR (400 MHz, acetone-$d_6$) δ ppm 1.44 (d, J=7.17 Hz, 3H) 3.50-3.72 (m, 3H) 4.20 (q, J=7.18 Hz, 1H) 7.11-7.26 (m, 1H) 7.37 (d, J=4.73 Hz, 2H) 7.56-7.66 (m, 1H).

2-(2-Bromo-phenyl)-propan-1-ol

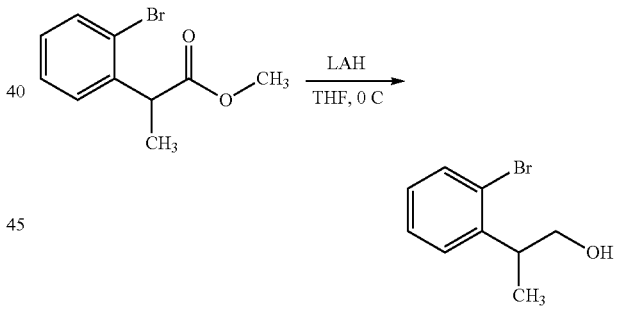

In a 250 mL round bottom flask, 3.2984 g (12.8278 mmol, 1.0 eq) of the ester was taken up in 100 mL of clean, dry THF under an atmosphere of $N_2$. The reaction solution was cooled to 0° C. in a wet ice bath. To this was slowly added 7.0 mL (14.1006 mmol, 1.1 eq) of the LAH solution (2.0 M in THF). The reaction was allowed to stir for 1 h. The wet ice bath was recharged with more ice and the reaction was then slowly and carefully quenched with 20 mL of 2 M HCl solution. Once the reaction was quenched, the mixture was poured into 50 mL of $H_2O$. To this was added 100 mL of EtOAc. The mixture was then stirred vigorously for five minutes. The layers were then separated. This was repeated two more times. The organic layers were combined, washed with brine (2×75 mL), and dried over $Na_2SO_4$. The solvent was removed under reduced pressure. Product was then purified using silica get column chromatography, eluting 100% heptane to 40 EtOAc in heptane. A colorless oil was isolated. LCMS (m/e): 230 (M+H);

$^1$H NMR (400 MHz, acetone) δ ppm 1.25 (s, 3H) 3.50-3.64 (m, 1H) 3.67-3.81 (m, 2H) 7.01-7.14 (m, 1H) 7.27-7.41 (m, 2H) 7.55 (d, J=7.86 Hz, 1H).

2-[2-(2-Bromophenyl)-propoxy]-tetrahydropyran

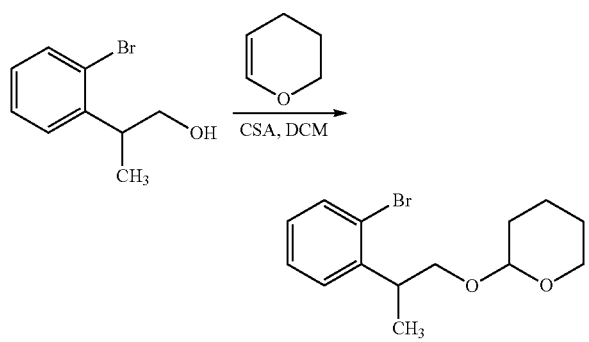

In a 250 mL round bottom flask, 1.1687 g (5.0310 mmol, 0.5 eq) of the CSA were taken up in 90 mL of clean, dry DCM under N$_2$ atmosphere. 2.3054 g (10.0620 mmol, 1.0 eq) of the alcohol was then dissolved in 3 mL of DCM and the alcohol solution was added to the stirring solution of CSA in DCM. The mixture was stirred for ten minutes until all of the CSA was completely dissolved. 1.82 mL (20.1240 mmol, 2.0 eq) of the DHP was added to the reaction mixture in one portion and the reaction was allowed to stir overnight. As the reaction progressed, the solution began to slowly change colors, becoming more violet as the reaction proceeded. The following morning, the reaction was quenched with 20 mL of saturated NaHCO$_3$ solution. The mixture was then poured into 50 mL of H$_2$O. The layers were separated and the aqueous layer was extracted with DCM (2×75 mL). The organic fractions were combined, washed with brine (1×100 ML) and dried over MgSO$_4$. The reaction was then filtered through filter paper and the solvent was removed under reduced pressure. A dark amber oil was then purified using silica gel column chromatography, eluting 100% heptane to 25% EtOAc in heptane. The product was isolated as a slightly yellow oil. LCMS (m/e): 314 (M+H); $^1$H NMR (400 MHz, acetone-d$_6$) δ ppm 1.21-1.39 (m, 18H) 3.29-3.48 (m, 2H) 3.48-3.60 (m, 1H) 3.63-3.77 (m, 2H) 4.48-4.68 (m, 1H) 7.14 (t, J=7.59 Hz, 1H) 7.30-7.38 (m, 1H) 7.43 (s, 1H) 7.58 (dd, J=7.96, 0.78 Hz, 1H).

4-Methyl-3,4-dihydro-benzo[c][1,2]oxaborinin-1-ol

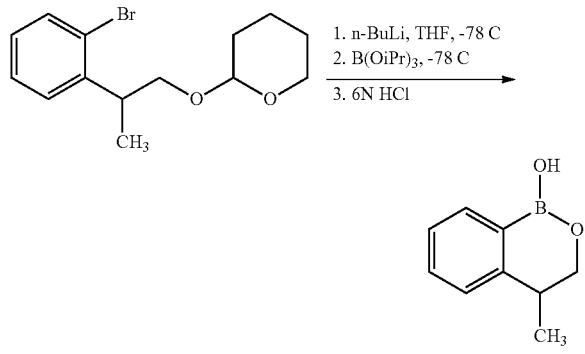

In a 250 mL round bottom flask, 3.2054 g (10.2330 mmol, 1.0 eq) of the protected alcohol was dissolved in 83 mL of reagent-grade THF under N$_2$ atmosphere. The solution was then cooled to −78° C. using a dry ice/acetone bath. 4.50 mL (11.2563 mmol, 1.1 eq) of the n-BuLi (2.5 M in hexanes) was added dropwise to the solution. The reaction was allowed to stir for 30 min while maintaining lowered temperature. 3.54 mL (15.3495 mmol, 1.5 eq) of the triisopropyl borate was added to the reaction slowly at −78° C. Upon complete addition of the triisopropyl borate, the reaction was allowed to gradually warm to room temperature overnight, maintaining inert atmosphere. The following morning, the reaction was quenched by the slow addition of 20 mL of 6M HCl (aq). The reaction was allowed to stir for 1 h. The reaction solution was then diluted with 50 mL of EtOAc and poured into 50 mL of H$_2$O. The layers were separated, and the aqueous layer was extracted with EtOAc (2×50 mL). The organic layers were combined, washed with brine, and dried over Na$_2$SO$_4$. The solution was decanted and the solvent was removed under reduced pressure. The oily material was then taken up in 25 mL of DCM and stirred together with 25 mL of 10% NaOH solution. The layers were separated and the aqueous layer was neutralized with 2N HCl. The aqueous layer was then re-extracted with EtOAc (3×30 mL) and the organic layer was washed with brine (1×50 mL) and dried over Na$_2$SO$_4$. The solvent was then removed under reduced pressure, yielding a colorless oil. LCMS (m/e): 177 (M+H); $^1$H NMR (400 MHz, acetone-d$_6$) δ ppm 1.22-1.28 (m, 3H) 3.82-3.92 (m, 1H) 4.14 (dd, J=10.84, 3.95 Hz, 1H) 7.15-7.31 (m, 2H) 7.35-7.48 (m, 1H) 7.75 (d, J=7.17 Hz, 1H).

4-Methyl-7-nitro-3,4-dihydro-benzo[c][1,2]oxaborinin-1-ol

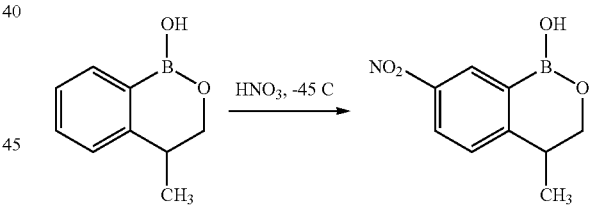

In a 100 ml round bottom flask, the fuming nitric acid was cooled to −45° C. using a dry ice/acetonitrile bath. 3.2054 g (10.2330 mmol, 1.0 eq) of the oxaborininol was dissolved in 2.5 mL of nitrobenzene. This solution was then added dropwise to the stirred and cooled nitric acid over a period of approximately 15 minutes. The reaction was allowed to stir for 45 minutes, recharging the acetonitrile and dry ice as needed. After 45 minutes, the reaction solution was poured over approximately 250 mL of wet ice. The mixture/suspension was allowed to warm to room temperature, stirring as it warmed (approximately 90 minutes). The aqueous mixture was then extracted with DCM (2×50 mL). The layers were separated and the organic layers were combined and washed with water to remove excess nitric acid (2×100 mL) until pH paper showed the water retained a neutral pH. The organic solution was then dried over MgSO$_4$, filtered under vacuum, and then the solvent was removed under reduced pressure.

The resultant yellow oil was then treated slowly with heptane, swirling as the solvent was added, until a yellow-white solid crashed out. The solid was then collected by filtration and washed with additional ice-cooled heptane. A yellow powder was isolated. ¹H NMR (400 MHz, DMSO-d₆) δ ppm 0.99-1.47 (m, 4H) 3.14 (dd, J=10.98, 5.86 Hz, 1H) 3.88 (dt, J=11.21, 5.79 Hz, 1H) 4.13 (dd, J=11.03, 4.00 Hz, 1H) 7.57 (d, J=8.44 Hz, 1H) 8.27 (dd, J=8.42, 2.56 Hz, 1H) 8.48 (d, J=2.49 Hz, 1H) 8.95 (s, 1H).

4-Fluoro-N-(1-hydroxy-4-methyl-3,4-dihydro-1H-benzo[c][1,2]oxaborinin-7-yl)-2-methyl-benzamide

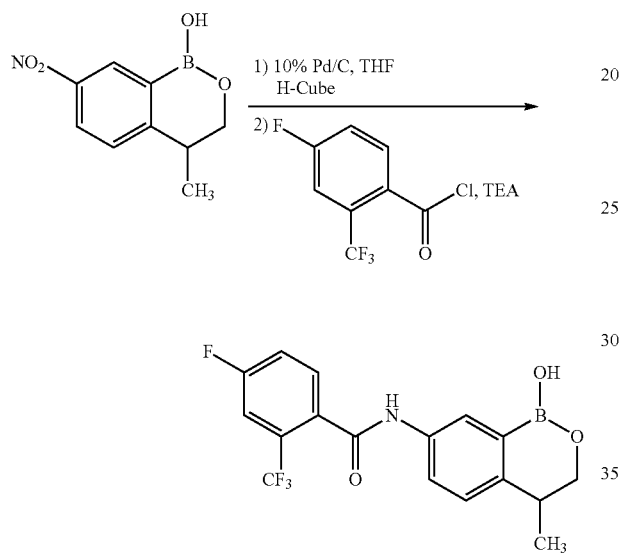

In a 40 mL scintillation vial, 91.8 mg of the oxaborininol (0.4435 mmol, 1.0 eq) was dissolved in 7 mL of clean, dry THF. This was then passed through the H-Cube hydrogenation device, using a 10% Pd/C CatCart catalyst cartridge, eluting at 1 mL/min, 25° C. and 1 atm of pressure. A yellowish solution was collected. 0.13 mL of the triethyl amine (0.9757 mmol, 2.2 eq) was then immediately added to the solution, followed by 0.07 mL of the benzoyl chloride (0.4335 mmol, 1.0 eq). The reaction was then allowed to stir overnight at room temperature under inert atmosphere. The following morning, the reaction was quenched with 2 mL of 2M HCl. The solution was poured into 10 mL of H₂O and was then extracted with EtOAc (3×15 mL). The layers were separated and the organic fractions were combined, washed with brine (1×50 mL), and dried over Na₂SO₄. The solution was decanted and the solvent was removed under reduced pressure. The product was then purified using silica gel column chromatography, eluting 100% DCM to 4.5% MeOH in DCM. The product was isolated as a white solid. LCMS (m/e): 368 (M+H); ¹H NMR (400 MHz, DMSO-d₆) δ ppm 1.19 (d, J=7.0 Hz, 3H) 2.86-3.04 (m, 1H) 3.81 (dd, J=10.9, 6.0 Hz, 1H) 4.08 (dd, J=10.8, 4.0 Hz, 1H) 7.24 (d, J=8.3 Hz, 1H) 7.57-7.73 (m, 2H) 7.79 (d, J=2.5 Hz, 1H) 7.93 (d, J=2.1 Hz, 1H) 8.44 (s, 1H) 10.48 (s, 1H).

M51. 4-Fluoro-N-(1-hydroxy-4,4-dimethyl-3,4-dihydro-1H-benzo[c][1,2]oxaborinin-7-yl)-2-methyl-benzamide

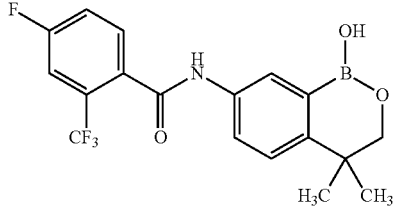 [SMILES: CC1(C)COB(O)c2cc(NC(=O)c3ccc(F)cc3C(F)(F)F)ccc21]

2-(2-Bromo-phenyl)-2-methyl-propionic acid methyl ester

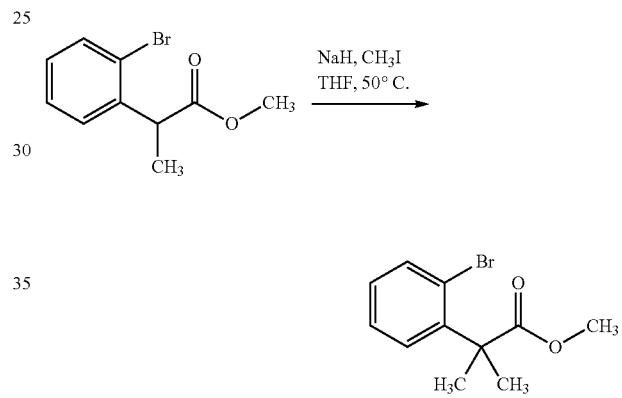

In a 500 mL round bottom flask, sodium hydride was suspended in 150 mL of clean, dry, reagent-grade THF under N₂ atmosphere. To this was added the ester dissolved in 50 mL of THF. The solution began to turn a pale yellow color. The reaction was then heated in an oil bath for 1 h at 50° C. After an hour, the iodomethane was added in one portion to the reaction, and the reaction mixture was heated and stirred at 50° C. for 24 hours. The following day, the reaction mixture was cooled to room temperature and carefully quenched with saturated NH₄Cl (aq) solution. The reaction stirred for 15 minutes and then was poured into 100 mL of H₂O. The product was then extracted with EtOAc (4×150 mL). The layers were separated and the organic fractions were combined, washed with brine (2×100 mL) and dried over Na₂SO₄. The solution was then decanted and the solvent was removed under reduced pressure. The product was purified using silica gel column chromatography, eluting with a gradient 100% heptane to 35% EtOAc in heptane. Product was isolated as a colorless oil. LCMS (m/e): 258 (M+H); ¹H NMR (400 MHz, acetone-d₆) δ ppm 1.60 (s, 7H) 3.53-3.66 (m, 3H) 7.19 (td, J=7.61, 1.56 Hz, 1H) 7.34-7.42 (m, 1H) 7.50-7.56 (m, 1H) 7.59 (dd, J=7.91, 1.07 Hz, 1H).

2-(2-Bromo-phenyl)-2-methylpropan-1-ol

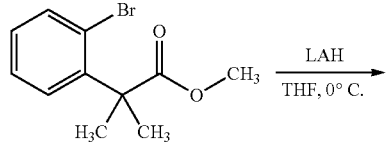

This compound was prepared in a manner similar to that of 2-(2-bromo-phenyl)-propan-1-ol. Data: LCMS (m/e): 230 (M+H); $^1$H NMR (400 MHz, acetone-d$_6$) δ ppm 1.48 (s, 6H) 3.94 (d, J=5.71 Hz, 2H) 7.04-7.15 (m, 1H) 7.26-7.35 (m, 1H) 7.50-7.65 (m, 2H).

2-[2-(2-Bromo-phenyl)-2-methyl-propoxy]-tetrahydropyran

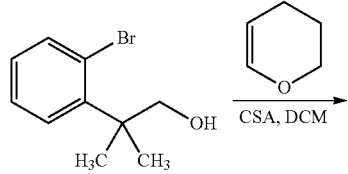

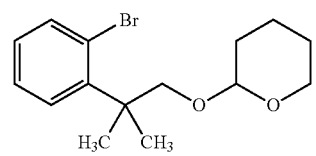

This compound was prepared in a manner similar to that of 2-[2-(2-Bromophenyl)-propoxy]-tetrahydropyran. Data: LCMS (m/e): 314 (M+H); $^1$H NMR (400 MHz, acetone-d$_3$) δ ppm 1.19-1.57 (m, 9H) 3.33-3.49 (m, 2H) 3.60-3.78 (m, 3H) 4.08 (d, J=9.62 Hz, 1H) 7.10 (td, J=7.55, 1.49 Hz, 1H) 7.24-7.36 (m, 1H) 7.47-7.55 (m, 1H) 7.58 (dd, J=7.86, 1.12 Hz, 1H).

4,4-Dimethyl-3,4-dihydro-benzo[c][1,2]oxaborinin-1-ol

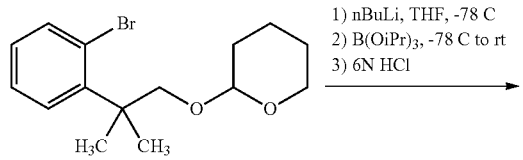

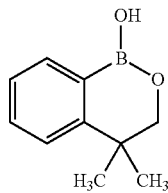

This compound was prepared in a manner similar to that of 4-methyl-3,4-dihydro-benzo[c][1,2]oxaborinin-1-ol. Data: $^1$H NMR (400 MHz, acetone-d$_6$) δ ppm 1.23-1.28 (m, 6H) 3.99-4.12 (m, 2H) 7.13-7.31 (m, 2H) 7.34-7.52 (m, 2H).

4,4-Dimethyl-7-nitro-3,4-dihydrobenzo[c][1,2]oxaborinin-1-ol

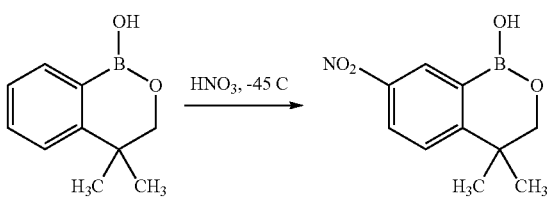 [SMILES: CC1(C)COB(O)c2ccccc21 ; CC1(C)COB(O)c2cc([N+](=O)[O-])ccc21]

This compound was prepared in a manner similar to that of 4-methyl-7-nitro-3,4-dihydro-benzo[c][1,2]oxaborinin-1-ol. Data: $^1$H NMR (400 MHz, DMSO-d$_6$) δ ppm 1.25 (s, 6H) 3.85 (s, 2H) 7.67 (d, J=8.59 Hz, 1H) 8.28 (dd, J=8.54, 2.59 Hz, 1H) 8.47 (d, J=2.54 Hz, 1H) 8.98 (s, 1H).

4-Fluoro-N-(1-hydroxy-4,4-dimethyl-3,4-dihydro-1H-benzo[c][1,2]oxaborinin-7-yl)-2-methyl-benzamide

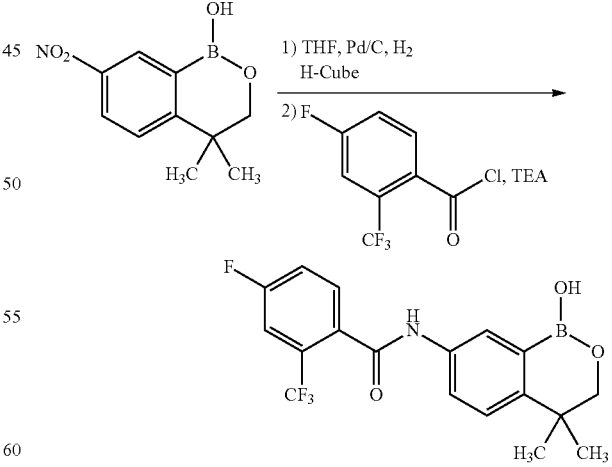

This compound was prepared in a manner similar to that of 4-Fluoro-N-(1-hydroxy-4-methyl-3,4-dihydro-1H-benzo[c][1,2]oxaborinin-7-yl)-2-methyl-benzamide. Data for MM: LCMS (m/e): 382 (M+H); $^1$H NMR (400 MHz, DMSO-d$_6$) δ ppm 1.20 (s, 6H) 3.78 (s, 2H) 7.34 (d, J=8.4 Hz, 1H) 7.69 (td, J=7.9, 2.3 Hz, 2H) 7.74-7.84 (m, 2H) 7.92 (d, J=2.2 Hz, 1H) 8.47 (br. s., 1H) 10.48 (s, 1H).

M52. 4-Fluoro-N-(1-hydroxy-3,3-dimethyl-3,4-dihydro-1H-benzo[c][1,2]oxaborinin-7-yl)-2-trifluoromethyl-benzamide

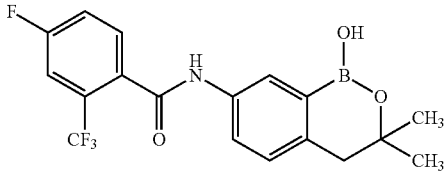 [SMILES: CC1(C)Cc2ccc(NC(=O)c3ccc(F)cc3C(F)(F)F)cc2B(O)O1]

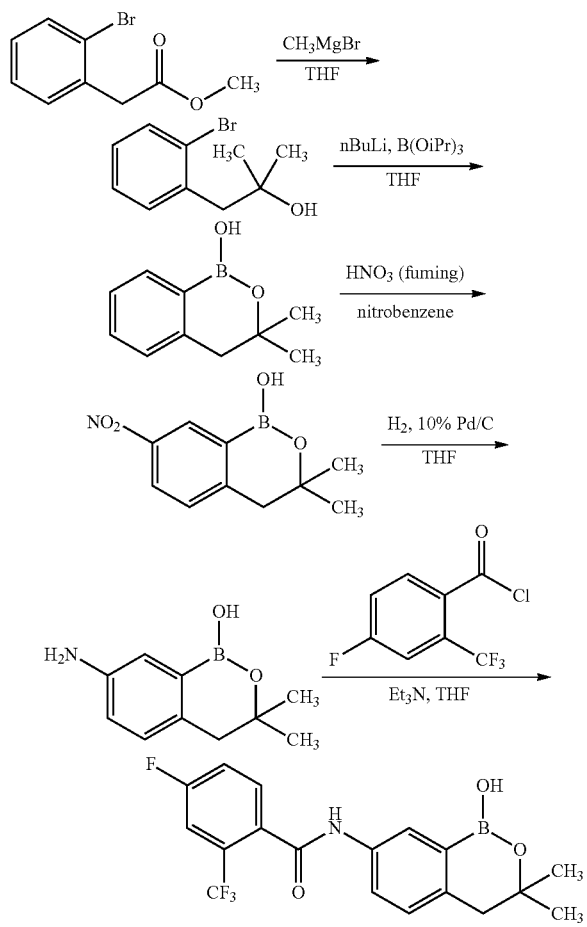

To a solution of (2-bromophenyl)acetic acid methyl ester (4.98 g, 22 mmol) in THF (100 mL) at 0° C., was added methyl magnesium bromide (21.7 mL, 3M in Et$_2$O) in a dropwise fashion. The reaction was stirred for 16 hours, gradually warming to room temperature. The solution was then cooled to 0° C., and saturated aqueous ammonium chloride (1 mL) was added. After 10 minutes, the solution mixture was concentrated by rotary evaporation, and the crude material was purified by silica gel chromatography to yield 1-(2-Bromophenyl)-2-methylpropan-2-ol as a colorless oil. $^1$H NMR (400 MHz, CHLOROFORM-d) δ ppm 1.30 (s, 6H) 3.03 (s, 2H) 7.07-7.13 (m, 1H) 7.24-7.29 (m, 1H) 7.34-7.39 (m, 1H) 7.56-7.61 (m, 1H). Amount obtained: 3.48 g, 70% yield.

To a solution of 1-(2-bromophenyl)-2-methylpropan-2-ol (3.48 g, 15 mmol) in THF (100 mL) cooled to –78° C. was added n-butyllithium (15.2 mL, 2.5M in hexanes) in a dropwise fashion. The reaction was permitted to stir for 10 minutes, prior to the addition of triisopropylborate (10.5 mL, 45 mmol). The reaction was permitted to stir for 16 hours, gradually warming to room temperature. Aqueous hydrochloric acid (10 mL, 6M) was added, and the mixture stirred for 1 hour. The reaction was diluted with EtOAc (250 mL) and water (50 mL). The organic portion was washed with brine, dried over sodium sulfate, and evaporated. The resultant crude material was purified by silica gel chromatography to yield 3,3-Dimethyl-3,4-dihydro-benzo[c][1,2]oxaborinin-1-ol as a white semisolid product. $^1$H NMR (400 MHz, acetone) δ ppm 1.13 (s, 6H) 2.76 (s, 2H) 6.99-7.04 (m, 1H) 7.05-7.14 (m, 1H) 7.21-7.27 (m, 1H) 7.58-7.64 (m, 1H). Amount obtained: 830 mg, 31% yield.

A solution of 3,3-dimethyl-3,4-dihydro-benzo[c][1,2]oxaborinin-1-ol (0.82 g, 4.7 mmol) in nitrobenzene (2.5 mL) was added dropwise to fuming nitric acid (10 mL) maintained at –45° C. The reaction was stirred for 45 minutes at this temperature, and then poured onto wet ice (400 mL). This mixture was allowed to stand for 90 minutes, gradually warming to room temperature. The resultant aqueous suspension was extracted with dichloromethane (3×50 mL). The combined organic portions were washed with water (2×50 mL) until the aqueous portion showed a pH of 7. The dichloromethane solution was then dried over sodium sulfate and concentrated to dryness. The resulting oil was triturated with heptane to produce 3,3-Dimethyl-7-nitro-3,4-dihydro-benzo[c][1,2]oxaborinin-1-ol as a white solid. $^1$H NMR (400 MHz, DMSO-d$_6$) δ ppm 1.25 (s, 6H) 3.02 (s, 2H) 7.47 (d, J=8.4 Hz, 1H) 8.25 (dd, J=8.3, 2.6 Hz, 1H) 8.47 (d, J=2.5 Hz, 1H) 8.85 (s, 1H). Amount obtained: 468 mg, 45% yield.

A solution of 3,3-dimethyl-7-nitro-3,4-dihydro-benzo[c][1,2]oxaborinin-1-ol (80 mg, 0.36 mmol) in dry THF (8 mL) was passed through a Thales Nano H-Cube hydrogenator (10% Pd/C catalyst, 1 mL/min flow rate, 1 atm, 30° C.), flushing with an additional 2 mL of THF. To the reaction solution was then added an excess of triethylamine (0.3 mL) and 4-fluoro-2-trifluoromethylbenzoyl chloride (100 mg, 0.44 mmol). The reaction was stirred at room temperature for 16 hours, and then diluted with aqueous hydrochloric acid (10 mL, 1 M). After vigorous mixing, the mixture was extracted with EtOAc (3×5 mL). The combined organic portions were dried over magnesium sulfate and concentrated to dryness. The crude product was purified by silica gel chromatography to produce the title compound as a white solid. LCMS (M/Z): 382 (M+H); $^1$H NMR (400 MHz, DMSO-d6) δ ppm 1.25 (s, 6H) 2.83 (s, 2H) 7.14 (d, J=8.4 Hz, 1H) 7.55-7.73 (m, 2H) 7.71-7.86 (m, 2H) 7.90 (d, J=2.3 Hz, 1H) 8.35 (s, 1H) 10.47 (s, 1H).

Example 2

*Trypanosoma brucei brucei* High-Throughput Screening Assay Procedure

All experiments were conducted with the bloodstream-form trypanosome *T. brucei* brucei 427 strain. Parasites were cultured in T-25 vented cap flasks and kept in humidified incubators at 37° C. and 5% CO$_2$. The parasite culture media was complete HMI-9 medium (c.f. Hirumi, Journal of Parasitology 1989, Volume 75, page 985 et seq) containing 10%

FBS, 10% Serum Plus medium and penicillin/streptomycin. To ensure log growth phase, trypanosomes were sub-cultured at appropriate dilutions every 2-3 days.

In Vitro Drug Sensitivity Assays

Log phase cultures were diluted 1:10 in HMI-9 and 10 uL was counted using hemocytometer to determine parasite concentration. Parasites were diluted to 2×105/mL in HMI-9 to generate a 2-fold working concentration for assay. Compounds to be tested were serially diluted in DMSO and 0.5 uL added to 49.5 uL HMI-9 in triplicate 96-well plates using a Biomek NX liquid handler. Parasites from the diluted stock were added to each well (50 uL) using a Multidrop 384 dispenser to give a final concentration of 1.0×105/ml parasites in 0.4% for DMSO. Trypanosomes were incubated with compounds for 72 hrs at 37° C. with 5% $CO_2$. Resazurin (20 uL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Biological data for exemplary compounds of the invention is provided in FIG. 1.

Example 3

L929 Cells and Cultivation

For evaluation of compound effects on mammalian cells, L929 mouse fibroblast cells were used. Cells were maintained as adherent cultures in T-25 vented cap flasks in a humidified incubator at 37° C. in the presence of 5% $CO_2$. Culture media was D-MEM supplemented with 10% fetal bovine serum and 1% penicillin/streptomycin. L929 cells were maintained below confluent levels by sub-culturing at 1:10 dilution twice weekly using 0.05% trypsin for detachment.

Cytotoxicity Evaluation

Sub-confluent L929 cells were trypsinized, resuspended in fresh media and 10 uL was counted using hemocytometer to determine cell concentration. Cells were diluted to $1\times10^4$/mL in DMEM, dispensed (100 uL) into 96-well plates using a Multidrop 384 dispenser and allowed to attach overnight. Spent media was replaced with 99.5 uL fresh D-MEM and compounds to be tested were serially diluted in DMSO and 0.5 uL added using a Biomek NX liquid handler. Plates were incubated with compounds for 72 hrs at 37° C. with 5% $CO_2$. Resazurin (20 uL of 12.5 mg/ml stock) from Sigma-Aldrich was added to each well and plates were incubated for an additional 3-4 hrs. Assay plates were read using an EnVision plate reader at an excitation wavelength of 544 nm and emission of 590 nm. Single data points were used to generate sigmoidal dose response curves and determine $IC_{50}$ values using XLfit curve fitting software from IDBS (Guildford, UK).

Biological data for exemplary compounds of the invention is provided in FIG. 1.

Example 4

Liver S9 Metabolism Assay Conditions

Liver S9 fractions from male CD1 mice were purchased from XenoTech LLC (Lenexa, Kans.) and stored at −70° C. until use. The activity profile of the major metabolic enzymes, as provided by the vendor for each lot, was stored with the raw data.

Preparation of Test Compound Solutions:

A stock solution of each compound tested was prepared in DMSO at a concentration of 10 mg/mL. Stock solutions were further diluted in DMSO to a concentration of 100 μM for use in the assay. The final assay concentration of each compound tested in each incubation mixture was 1 μM and the final concentration of DMSO was 1%.

Incubation Conditions:

Incubations of a compound with CD1 mouse liver S9 fractions were carried out in duplicate at a final concentration of 1 μM. The incubation mixtures included 100 mM potassium phosphate buffer (pH 7.4) with the following cofactors: 1.14 mM β-NADPH, 1.43 mM glucose-6-phosphate, 1.43 mM uridine 5'-diphosphoglucuronic acid (UDPGA), 9.42 mM potassium chloride, and 2.28 mM magnesium chloride (final assay concentration). The reactions were initiated by the addition of the cofactors to the incubation mixtures. The total incubation contained an S9 protein concentration of 2.5 mg/mL. Incubations were performed at 37° C. in an oxygen and humidity enriched atmosphere with shaking (200 rpm), for time periods of 0, 15, 30, and 60 minutes. At the end of each time period, an aliquot was taken and transferred to a clean 96-well plate containing three volumes of ice cold methanol. Samples were centrifuged at 4200×g for 20 minutes at 15° C. and the supernatants were transferred to new plates. Samples were analyzed by means of reversed-phase LC-MS/MS using the conditions summarized below. Peak areas were measured to calculate the percent of parent compound remaining and the half life.

Liquid Chromatography Settings

Column: Phenomenex Luna C8(2), 3μ, 100 A, 50×2 mm, P/N 00B-4248-B0 with C8 guard cartridge, P/N AJO-4289

Mobile Phase:
Aqueous (A): 10 mM ammonium acetate in $H_2O$
Organic (B): 10 mM ammonium acetate in methanol Flow: 600 μL/minute Gradient Conditions:

| Time (Min) | % A | % B |
|---|---|---|
| 0.00 | 65 | 35 |
| 0.25 | 65 | 35 |
| 1.50 | 5 | 95 |
| 2.00 | 5 | 95 |
| 2.01 | 65 | 35 |
| 3.00 | 65 | 35 |

Total Run Time: 3.0 minutes

Autosampler Settings:
Injection Volume: 10 μL (20 μL, injected on a 10 μL, sample loop)
Wash 1: ACN/$H_2O$ (80:20, v/v)
Wash 2: MeOH Typical Mass Spectrometer Settings:

| | |
|---|---|
| Mass spectrometer: | Applied Biosystems API 4000 QTRAP |
| Mode: | Multiple Reaction Monitoring |
| Interface: | Heated Nebulizer[a] |
| Polarity: | Negative[a] |
| Nebulizer Current: | −3[a] |
| Resolution: | Low/Low[a] |
| Temperature: | 500° C.[a] |
| CUR: | 10[a] |
| CAD: | High[a] |

| | |
|---|---|
| GS1: | 40[a] |
| GS2: | 60[a] |

[a]Typical conditions are given. Actual settings used may differ to provide optimal conditions for individual compounds.

Biological data for exemplary compounds of the invention is provided in FIG. 1.

Example 5

Method for Estimation of Kinetic Solubility of Compounds of the Invention

The kinetic solubilities of compounds were estimated using a nephelometric (light scattering) method. Briefly, compounds were serially diluted in DMSO, followed by dilution in PBS pH 7.4. After incubation, the amount of light scattered by a compound at each concentration was measured. Clear solutions of soluble compounds do not scatter a light beam passed through the sample well and produce no signal. At concentrations above the solubility limit, the compound precipitates and the precipitant in the well scatters the light, generating a signal. Higher levels of precipitant in a well scatter more light and produce a stronger signal.

A stock solution of compound (25 mM in DMSO) was prepared, and was serially diluted in DMSO in two-fold increments in a row of a 96 well plate to a lowest concentration of 24 μM. A duplicate plate was prepared by transfer of half of the volume of each well to a new plate. Each well containing DMSO solution of the test compound was then diluted further (1:100) with phosphate buffered saline (pH 7.4) to provide aqueous solutions of compound at the following final concentrations: 250, 125, 62.5, 31.3, 15.6, 7.8, 3.9, 2.0, 1.0, 0.5 and 0.2 μM. All liquid handling stages were performed on a Beckman Coulter Biomek NX Laboratory Automation Workstation. Each compound was diluted and tested in duplicate, providing four separate wells at each test concentration.

The test solutions of compound were incubated at room temperature for 90 minutes and then analyzed using a Thermoskan Ascent nephelometric plate reader. The nephelometer protocol included two steps: first, the plate was shaken for 60 seconds at 1200 rpm, then each well of the plate was read in succession with an 800 ms settling delay between measurements. The total measurement time for a single plate was less than 4 minutes.

The four values (in nephelometric units) obtained for each compound at each concentration were averaged and plotted on a log scale versus concentration. The concentration at which the nephelometric signal is >110% of the value obtained for a DMSO/PBS blank is reported as the limit of solubility.

Biological data for exemplary compounds of the invention is provided in FIG. 1.

Example 6

Acute Murine Model A [Murine Stage 1 HAT]

Female Swiss Webster mice were inoculated with 250,000 parasites of the LAB 110 Eatro strain of *T. b. brucei*. 24 hrs post-infection, treatment was initiated by administration of a compound of the invention BID for 4 days with 20 mg/kg/dose (40 mg/kg/day) intraperitoneally (IP) or orally (PO), 5 mg/kg BID or 10 mg/kg BID orally (PO). 3 mice per group were treated with a particular compound of the invention. Mice were checked for parasitemia weekly by microscopic examination of smears prepared from tail vein blood. Animals remaining parasite free for more than 30 days beyond the end of the treatment period were considered cured. Control untreated animals typically succumbed to the infection within 4-5 days following i.p. inoculation with parasites. Mice were monitored for 30 days for survival. Pentamidine at 2 mg/kg IP was used as the positive control. After 10 days, 0% of the untreated mice were parasite free. After 10 days, 67% of mice treated PO with 10 mg/kg BID of N-(1-Hydroxy-3,4-dihydro-1H-benzo[c][1,2]oxaborinin-7-yl)-4-methoxy-benzamide (M19) were parasite free. After 30 days, 100% of mice treated PO with 10 mg/kg BID of 4-fluoro-N-(1-hydroxy-3,4-dihydro-1H-benzo[c][1,2]oxaborinin-7-yl)-2-trifluoromethyl-benzamide (M1) were parasite free. These results indicate that N-(1-Hydroxy-3,4-dihydro-1H-benzo[c][1,2]oxaborinin-7-yl)-4-methoxy-benzamide can prevent the development of diseases associated with *T. b. brucei*. These results indicate that 4-fluoro-N-(1-hydroxy-3,4-dihydro-1H-benzo[c][1,2]oxaborinin-7-yl)-2-trifluoromethyl-benzamide has potential for development to treat early-stage HAT.

TABLE

In vivo data for selected Examples in Acute Murine Model A.

| Compound # | Dose (mg/kg) | Mean Survival Days |
|---|---|---|
| Vehicle Control | | 4.5 |
| M1 | 10 | 30 |
| M5 | 10 | 7 |
| M8 | 10 | 5.6 |
| M12 | 10 | 8 |
| M14 | 10 | 3.6 |
| M15 | 10 | >30 |
| M19 | 10 | 9 |
| M27 | 10 | >30 |
| M29 | 10 | >30 |
| M40 | 10 | 4 |
| M46 | 10 | 5 |
| M47 | 10 | 9 |
| M51 | 10 | 3.6 |

Note:
All compounds were dosed for 4 days, BID, orally.

Example 7

Chronic CNS Model [Murine Stage 2 HAT]

Mice were infected with 10,000 parasites of the TREU 667 strain of *T. b. brucei*. Twenty one days post-infection mice were treated with a dose of between 6 and 100 mg/kg of a compound of the invention, either BID or QD for 7 days intraperitoneally (IP) or orally (PO). Positive control mice were treated with Diminazene (10 mg/kg, IP) on Day 4 post-infection. Negative control mice were treated with Diminazene (10 mg/kg, PO) on Day 21. Since Diminazene is not able to penetrate the CNS, mice treated at Day 21 are not able to cure the infection. Starting 1 week after treatment, mice were checked for parasitemia by microscopic examination of smears prepared from tail vein blood. Parasite positive animals were immediately removed from the cages and euthanized. Animals were considered to be cured of a CNS infection if they were aparasitemic for at least 180 days after the end of the treatment period.

For example, treatment with 50 mg/kg, PO, of 4-fluoro-N-(1-hydroxy-3,4-dihydro-1H-benzo[c][1,2]oxaborinin-7-yl)-2-trifluoromethyl-benzamide (M1) BID for 7 days, starting at Day 21 post-infection, resulted in absence of blood parasites through Day 180 in 100% of the mice. In contrast, all animals treated on Day 21 with the non-CNS penetrant drug Diminazene relapsed to exhibit blood parasitemia by Day 56. These results indicate that 4-fluoro-N-(1-hydroxy-3,4-dihydro-1H-benzo[c][1,2]oxaborinin-7-yl)-2-trifluoromethyl-benzamide has potential for development to treat late-stage HAT.

Example 8

Pharmacokinetic Studies in Mice

Male CD-1 mice weighing approximately 20 to 30 g received the test article M1 by either intravenous (IV) or oral gavage (OG) routes. Animals in the IV group (11 animals, 1 per time point) received a single bolus injection at a nominal dose level of 2 mg/kg of the test article. Animals receiving oral doses were administered the test article as a single OG dose (10 animals per dose level, 1 per time point) at nominal dose levels of 25 and 50 mg/kg.

IV doses were administered as a solution in 5% (w/v) dextrose in sterile water for injection. OG doses at 25 and 50 mg/kg were administered as suspensions in 5% (w/v) dextrose in sterile water for injection and as in situ sodium salts in 5% (m/v) dextrose: 2% (v/v) ethanol in DWI, respectively. All dose solutions were delivered at 4 mL/kg. Animals receiving the IV dose at 2 mg/kg or the OG dose at 25 mg/kg were not fasted. Animals receiving the OG dose at 50 mg/kg were fasted for 4 hours before dosing and for 1 hour after dosing.

Blood and brain tissue were collected from 1 animal/timepoint/group at 0.17, 0.5, 1, 2, 3, 4, 6, 8, 12, 18 and 24 hr after IV dosing, and at 0.5, 1, 2, 3, 4, 6, 8, 12, 18 and 24 hr after OG dosing. Whole blood samples were processed completely to plasma following collection. Plasma and brain tissue were submitted to bioanalysis to determine pharmacokinetic parameters and test article CNS disposition. Plasma and brain tissue from non-dosed animals were collected to serve as surrogate pre-dose samples.

Bioanalysis for test article in plasma and brain tissue was performed by HPLC with tandem mass spectrometry (LC-MSMS). Plasma samples were treated with 4 volumes of 0.5% formic acid in methanol to precipitate plasma proteins. Treated samples were centrifuged and supernatants removed for analysis. Brain tissues were massed and homogenized mechanically in the presence of 1 volume of phosphate-buffered saline (PBS). The resulting tissue homogenates were then diluted with a further volume of PBS, and then treated in the same manner as plasma.

Extracted samples were assayed for test article by means of LC-MSMS employing reversed-phase chromatography coupled to a triple quadrupole mass spectrometer employing electrospray ionization in the positive ion mode. The analytical column was a Phenomenex Luna 3µ C8 50×2 mm, with an online sample purification step performed on a Phenomenex Synergi 4µ Polar RP 50×2 mm column.

Test articles were eluted using a binary mobile phase gradient comprising 5 mM Ammonium Acetate: 0.1% formic acid in either MeOH or $H_2O$.

Non-compartmental analysis of plasma test article concentration versus time was performed in Microsoft Excel to generate pharmacokinetic parameters including: area under the curve (AUC), clearance (as Cl or Cl/F), volume of distribution (Vdss), half-life (t½), and bioavailability (F).

Results:
CNS Disposition:

With an oral dose of 25 mg/kg, the brain:plasma ratio of M1 is greater than unity for a period of approximately 4 hours following dosing. Brain concentrations of test article are maintained above the MIC following OG dosing at 25 and 50 mg/kg for periods of approximately 5 and 10 hours, respectively. The rate of elimination from the brain is similar to clearance from plasma.

Dose Proportionality:

M1 demonstrates a superproportional increase in plasma exposure relative to dose following oral delivery to mice. Brain exposure also increases with dose, although in an approximately proportional manner.

Results for M1 are presented in the tables below.

Summary plasma and brain pharmacokinetic parameters after oral administration of M1 to male CD-1 mice. Data normalized to 25 mg/kg or 50 mg/kg following nominal 25 mg/kg or 50 mg/kg doses.

|  | Plasma | | Brain | |
| --- | --- | --- | --- | --- |
|  | 25 mg/kg | 50 mg/kg | 25 mg/kg | 50 mg/kg |
| Cmax (µg/ml) | 2.23 | 13.43 | 5.84 | 4.21 |
| Exposure/ trapezoid $AUC_{0-last}$ (hr * µg/ml)† | 6.39 | 81.38 | 14.33 | 22.88 |
| Exposure/ trapezoid $AUC_{0-inf}$ (hr * µg/ml) | 6.46 | 83.41 | 14.37 | 24.70 |
| t½ (hr) | 5.29 | Elimination Phase not Defined | Elimination Phase not Defined | Elimination Phase not Defined |
| F (% of IV) | 43.2 | NA | NA | NA |
| Oral Clearance Cl/F (L/kg/hr) | 3.87 | 0.614 | 1.75 | 2.19 |

†Last = 24 hours for plasma and 12 hours for brain

Summary plasma and brain pharmacokinetic parameters after IV administration of M1 to male CD-1 mice. Data normalized to 2 mg/kg following nominal 2 mg/kg dose.

|  | Plasma 2 mg/kg | Brain 2 mg/kg |
| --- | --- | --- |
| Exposure/ trapezoid $AUC_{0-last}$ (hr * µg/ml)† | 1.58 | 0.70 |
| Exposure/ trapezoid $AUC_{0-inf}$ (hr * µg/ml) | 1.61 | 0.89 |
| t½ (hr) | 6.88 | Elimination Phase not Defined |
| Vdss (L/kg) | 5.00 | 17.09 |
| Clearance Cl (L/kg/hr) | 1.67 | 2.54 |

†Last = 24 hours for plasma and 12 hours for brain

Example 9

*Leishmania donovani* Strain and Cultivation

Experimental Procedures for In Vivo Screening Against *L. donovoni* in Golden Hamsters Maintenance of *L. donovani*—Golden Hamster Model:

Animals:

Golden hamsters (Inbred strain) reared at the animal facilities at CDRI are routinely used for the assay protocols. Naive 8-10 week-old hamsters, (weighing 40-45 g) of either sex were used for in vivo maintenance of the parasites. Throughout the study, the animals were housed in animal quarters with controlled climate (23±2° C.; RH: 60%) and photoperiodicity (12 hr light-dark cycles). Animals were fed with standard rodent pellets supplemented with gram and ad libitum access to drinking water was provided. Studies were conducted in compliance with the institutional animal ethics Committee guidelines on handling of animals.

Parasite:

*Leishmania donovani* (strain $Dd_b$) parasites are maintained via intra cardiac inoculation of $1\times10^7$ amastigote stage parasites per animal and development of infection was monitored by splenic biopsy. The infection is well adapted to the hamster model and establishes itself in 15-20 days. Meanwhile, hamsters gain weight (85-95 g) and can be subjected to repeated spleen biopsies.

Protocol for Antileishmanial Screening:

The method as proposed by Beveridge, (Chemotherapy of leishmaniasis. In: Schnitzer, R. J., Hawking, F (Eds.), Experimental Chemotherapy. Academic Press, New York, London, 1963, Vol. 1. pp. 257-280) and modified by Bhatnagar et al, (*I.J.M.R.*, 1989, 8, 439) was used for in-vivo screening.

Golden hamsters (of either sex) weighing 40-45 g are infected intracardially with $1\times10^7$ amastigotes per animal. Pre-treatment spleen biopsy was performed after 14-16 days in all the animals to assess the degree of infection. The animals with +1 infection (5-15 amastigotes/100 spleen cell nuclei) were included in the chemotherapeutic trials. Four to five animals were used for each test dose/sample. Drug treatment by oral or ip route was initiated after 2 days of biopsy and continued for 5 consecutive days. Post-treatment biopsies were performed on day 7 and 28 post treatment and amastigote counts were assessed by Giemsa staining. Intensity of infection in treated and untreated animals was compared with the initial parasite counts for the respective hamsters and the efficacy was expressed in terms of percentage inhibition.

$$\text{Percent Inhibition } (P.I.) \ 100 - \left(\frac{AT \times 100}{IT \times FI}\right) =$$

PI is percent inhibition of amastigote multiplication; AT is actual number of amastigotes in treated animals; IT is initial number of amastigotes in treated animals; and FI is fold increase of parasites in untreated control animals.

Example 10

MDCK-MDR1 Permeability Assay Conditions

Test System:

MDCK-MDR1 cells (Madin-Darby canine kidney cells transfected with the human MDR1 gene) (Dr. Piet Borst, NKI-AVL, Amsterdam, The Netherlands) were seeded at 300,000 cells per well onto microporous, polycarbonate membranes in 12 well Costar Transwell® plates (Corning, Corning, N.Y.). The medium was removed and replaced with fresh cell culture medium approximately 24 hours after plating. Cells attained confluency and were ready for use in the transport assay after 72 hours of incubation.

Preparation of Test Compound Solutions:

A stock solution of each compound was prepared in DMSO at a concentration of 10 mg/mL. Stock solutions were further diluted in DMSO to a concentration of 1 mM for use in the assay. The final assay concentration of test compound in each incubation mixture was 3 µM and the final concentration of DMSO was 0.3%.

Incubation Conditions:

Cell cultures were pre-incubated with Transport Medium (TM), consisting of Hanks Balanced Salt Solution (HBSS), 25 mM glucose, and 25 mM HEPES, with and without the known P-gp inhibitor GF120918 (2 µM final assay concentration), for 30-60 minutes prior to the addition of test and control compounds. Following the pre-incubation period, transepithelial electrical resistance (TEER) measurements were taken on each insert to insure the integrity of the monolayer. The range for TEER values was 45-85Ω·cm². Transport medium was removed. Fresh transport media (1.5 mL) with or without GF120918 was added to the basolateral chambers. Solutions of the test compound were diluted into TM and added to the appropriate wells in triplicate (400 µL/well) at a final concentration of 3 µM with and without GF120918. The final concentration of DMSO was 0.3%. Control compounds were tested in triplicate at a final concentration of 3 µM. Cell monolayers were incubated with shaking (160 rpm) at 37° C. with 5% $CO_2$ in a humidified incubator for one hour. Following the incubation, all plates were removed from the incubator. Inserts were removed from the plates and TEER measurements were again taken on each insert prior to removing samples for analysis to ensure no degradation of the tight junctions during the assay. An aliquot was taken from each receiver and diluted 1:3 with organic solvent (methanol) to assess transport of each compound across the monolayer. An aliquot was taken from each donor and diluted 1:2 with organic solvent (methanol) and then again 1:50 with matrix (50% methanol/50% TM) to assess mass balance within the study. All samples were assayed for test compound concentrations by LC-MS/MS using electrospray ionization.

MDCK-MDR1 Permeability information for compounds of the invention are provided in the table below.

TABLE

In vivo data for selected Examples in Acute Murine Model A.

| Compound # | MDCK-MCR1 Papp +918 (nm/sec) | MDCK-MCR1 AQ | MDCK-MCR1 Papp (nm/sec) |
|---|---|---|---|
| M1  | 545.8 | −0.02 | 556.9 |
| M5  | 776   | 0.1   | 707   |
| M12 | 770.8 | −0.04 | 803.2 |
| M27 | 828.7 | −0.03 | 851.4 |
| M29 | 776.4 | −0.04 | 803.7 |
| M43 | 680.1 | 0.05  | 648.6 |
| M46 | 810.2 | 0.05  | 770.8 |
| M47 | 672   | 0.04  | 648   |

Note:
All compounds were dosed for 4 days, BID, orally.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the following formula:

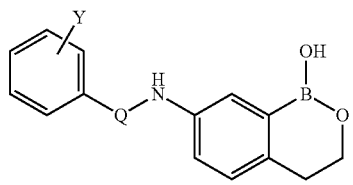

wherein Q is SO$_2$ or C=O, Y is selected from the group consisting of halogen, halo-substituted C$_1$-C$_6$ alkyl and unsubstituted C$_1$-C$_6$ alkyl, or a salt thereof;

or the following formula:

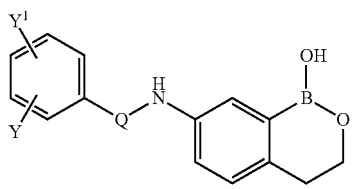

wherein Q is SO$_2$ or C=O, Y$^1$ is a halogen, Y is halosubstituted alkyl, or a salt thereof.

2. The compound of claim 1, or a salt thereof, wherein Q is C=O.

3. The compound of claim 1, or a salt thereof, having a structure according to the following formula:

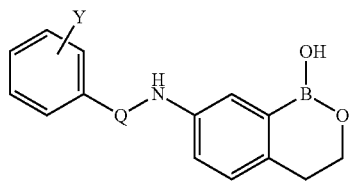

wherein Q is SO$_2$ or C=O, Y is selected from the group consisting of halogen, halo-substituted C$_1$-C$_6$ alkyl and unsubstituted C$_1$-C$_6$ alkyl.

4. The compound of claim 3, or a salt thereof, wherein Y is halo-substituted C$_1$-C$_6$ alkyl.

5. The compound of claim 3, or a salt thereof, wherein Y is C$_1$-C$_6$ alkyl, substituted with three halogens.

6. The compound of claim 3, or a salt thereof, wherein Y is CF$_3$.

7. The compound of claim 3, or a salt thereof, wherein the compound is

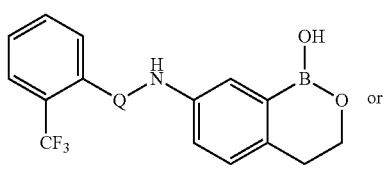

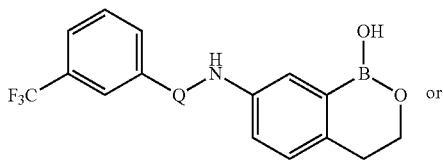

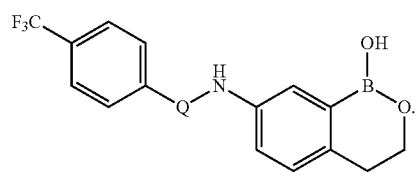

8. The compound of claim 3, or a salt thereof, wherein the compound is

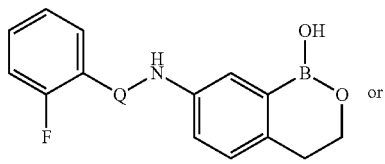

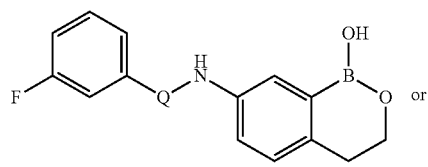

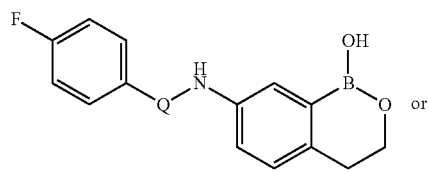

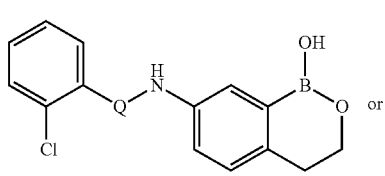

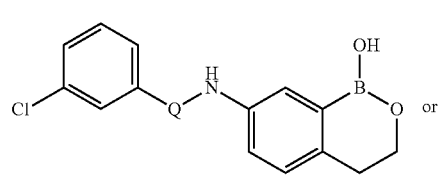

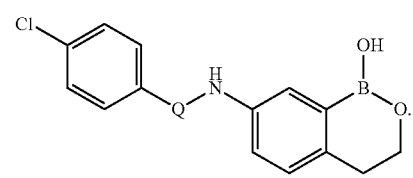

9. The compound of claim 1, or a salt thereof, having a structure according to the following formula:

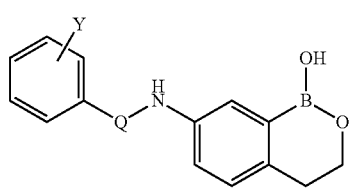

wherein Q is SO$_2$ or C=O, Y is unsubstituted C$_1$-C$_6$ alkyl.

10. The compound of claim 1, or a salt thereof, having a structure according to the following formula:

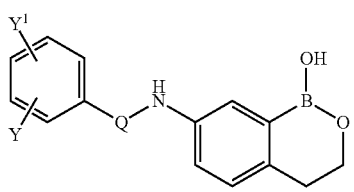

wherein Q is SO$_2$ or C=O, Y$^1$ is a halogen, Y is halosubstituted alkyl.

11. The compound of claim 10, or a salt thereof, wherein Y$^1$ is fluoro or chloro.

12. The compound of claim 10, or a salt thereof, wherein Y is trifluoromethyl.

13. The compound of claim 10, or a salt thereof, which is:

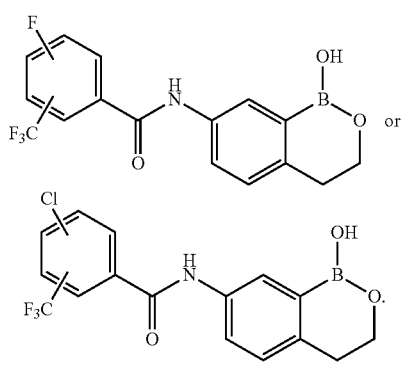

14. The compound of claim 10, or a salt thereof, which is:

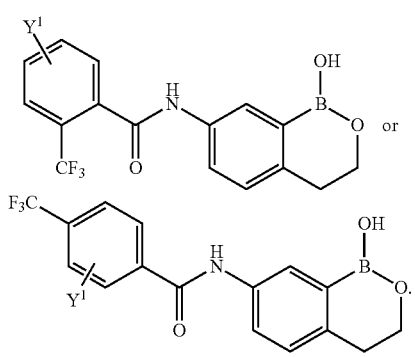

15. The compound of claim 10, or a salt thereof, which is:

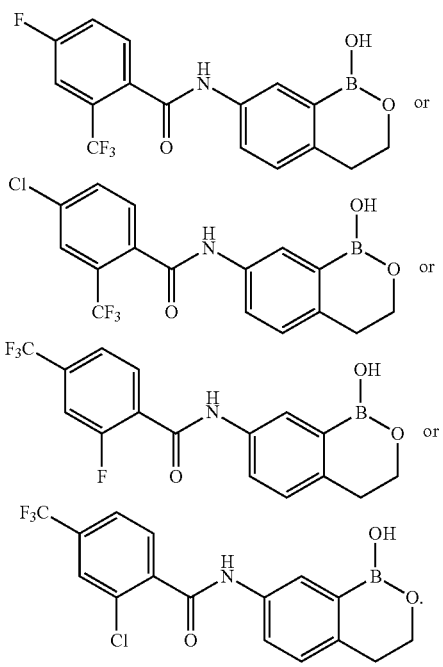

16. A combination comprising the compound of claim 1, or a salt thereof, together with at least one other therapeutically active agent.

17. A pharmaceutical formulation comprising:
a) the compound of claim 1, or a salt thereof; and
b) a pharmaceutically acceptable excipient.

18. The pharmaceutical formulation of claim 17, wherein the pharmaceutical formulation is a unit dosage form.

19. The pharmaceutical formulation of claim 17, wherein the salt of said compound is a pharmaceutically acceptable salt.

20. A method of killing and/or inhibiting the growth of a protozoa, comprising: contacting the protozoa with an effective amount of the compound of claim 1, or a salt thereof, thereby killing and/or inhibiting the growth of the protozoa.

21. The method of claim 20, wherein the protozoa is *Trypanosoma*.

22. The method of claim 20, wherein the protozoa is *Trypanosoma brucei*.

23. The method of claim 22, wherein the *Trypanosoma brucei* is a member selected from *Trypanosoma brucei brucei*, *Trypanosoma brucei gambiense* and *Trypanosoma brucei rhodesiense*.

24. A method of treating a trypanosomiasis in an animal, comprising: administering to the animal a therapeutically effective amount of the compound of claim 1, or a salt thereof, thereby treating the trypanosomiasis.

25. The method of claim 24, wherein the trypanosomiasis is sleeping sickness.

26. The method of claim 24, wherein the animal is a human.

27. The method of claim 24, wherein the trypanosomiasis is nagana.

28. The method of claim 24, wherein the animal is cattle.

* * * * *